United States Patent
LaVoie et al.

(10) Patent No.: US 9,475,783 B2
(45) Date of Patent: Oct. 25, 2016

(54) ANTIMICROBIAL AGENTS

(71) Applicant: Rutgers, the State University of New Jersey, New Brunswick, NJ (US)

(72) Inventors: Edmond J. LaVoie, New Brunswick, NJ (US); Ajit Parhi, New Brunswick, NJ (US); Yongzheng Zhang, New Brunswick, NJ (US); Daniel S. Pilch, New Brunswick, NJ (US); Malvika Kaul, New Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 14/386,718

(22) PCT Filed: Mar. 21, 2013

(86) PCT No.: PCT/US2013/033343
§ 371 (c)(1),
(2) Date: Sep. 19, 2014

(87) PCT Pub. No.: WO2013/142712
PCT Pub. Date: Sep. 26, 2013

(65) Prior Publication Data
US 2015/0031694 A1    Jan. 29, 2015

Related U.S. Application Data

(60) Provisional application No. 61/613,903, filed on Mar. 21, 2012.

(51) Int. Cl.
| | | |
|---|---|---|
| *C07D 263/32* | (2006.01) | |
| *C07D 277/30* | (2006.01) | |
| *C07D 417/04* | (2006.01) | |
| *C07D 277/64* | (2006.01) | |
| *C07D 417/12* | (2006.01) | |
| *C07D 263/56* | (2006.01) | |
| *C07D 513/04* | (2006.01) | |
| *C07D 263/34* | (2006.01) | |
| *C07D 277/24* | (2006.01) | |

(52) U.S. Cl.
CPC ........... *C07D 277/64* (2013.01); *C07D 263/32* (2013.01); *C07D 263/34* (2013.01); *C07D 263/56* (2013.01); *C07D 277/24* (2013.01); *C07D 277/30* (2013.01); *C07D 417/04* (2013.01); *C07D 417/12* (2013.01); *C07D 513/04* (2013.01)

(58) Field of Classification Search
CPC  C07D 513/04; C07D 277/30; C07D 263/56; C07D 263/32; C07D 417/04; C07D 263/34; C07D 417/12; C07D 277/64; C07D 277/24
USPC ....... 514/234.2, 301, 367, 253.04, 374, 375, 514/365, 321, 233.8; 544/362, 127; 546/198, 209, 114; 548/236, 217, 205, 548/180
See application file for complete search history.

(56) References Cited

U.S. PATENT DOCUMENTS

| | | |
|---|---|---|
| 4,309,539 A | 1/1982 | Boller et al. |
| 4,782,058 A | 11/1988 | Griffith |
| 4,826,990 A | 5/1989 | Musser et al. |
| 5,077,142 A | 12/1991 | Sakon et al. |
| 5,177,067 A | 1/1993 | Guerry et al. |
| 5,177,075 A | 1/1993 | Suto et al. |
| 8,088,791 B2 | 1/2012 | Brown et al. |
| 8,415,383 B2 | 4/2013 | Haydon et al. |
| 8,492,414 B2 | 7/2013 | Haydon et al. |
| 8,865,736 B2 | 10/2014 | Brown et al. |
| 8,933,096 B2 | 1/2015 | LaVoie et al. |
| 2002/0035090 A1 | 3/2002 | Zeldis et al. |
| 2002/0040147 A1 | 4/2002 | Hammond et al. |

(Continued)

FOREIGN PATENT DOCUMENTS

| | | |
|---|---|---|
| DE | 4327748 A1 | 2/1995 |
| EP | 0719764 A1 | 7/1996 |

(Continued)

OTHER PUBLICATIONS

Dorwald; "Side Reactions in Organic Synthesis: A Guide to Successful Synthesis Design" 2005 Wiley-VCH Verlag GmbH & Co. KGaA, Wienheim.*
Czaplewski; Bioorganic and Medicinal Chemistry Letters, 2009, 19, 524-527.*
Kaul; Antimicrob. Agents Chemother., 2013, 57, 5860-5869.*
Chemical Abstracts STN Registry Database Record for RN 338394-05-1, Entered on May 25, 2001.*
Schonenberger; Archiv der Pharmazie, 1976, 309, 289-301.*

(Continued)

Primary Examiner — Noble Jarrell
Assistant Examiner — Daniel Carcanague
(74) Attorney, Agent, or Firm — Viksnins Harris & Padys PLLP

(57) ABSTRACT

The invention provides compounds of formula (I):

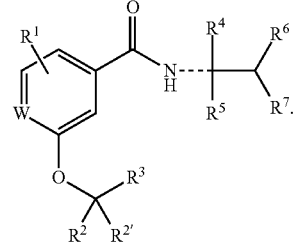

wherein $R^1$-$R^7$ and W have any of the values defined in the specification, and salts thereof. The compounds have good solubility and are useful for treating bacterial infections.

41 Claims, No Drawings

(56) References Cited

U.S. PATENT DOCUMENTS

| | | |
|---|---|---|
| 2002/0055516 A1 | 5/2002 | Miyazaki et al. |
| 2002/0077333 A1 | 6/2002 | Dey et al. |
| 2003/0181519 A1 | 9/2003 | Mewshaw et al. |
| 2005/0043300 A1 | 2/2005 | Middleton et al. |
| 2006/0183943 A1 | 8/2006 | Hu |
| 2008/0027028 A1 | 1/2008 | Chichak |
| 2008/0300239 A1 | 12/2008 | Adams et al. |
| 2009/0076074 A1 | 3/2009 | Jung et al. |
| 2009/0312319 A1 | 12/2009 | Ren et al. |
| 2010/0120810 A1 | 5/2010 | Leblond et al. |
| 2012/0022061 A1 | 1/2012 | LaVoie |
| 2013/0109713 A1 | 5/2013 | LaVoie et al. |
| 2013/0116278 A1 | 5/2013 | LaVoie |
| 2014/0135332 A1 | 5/2014 | Haydon et al. |
| 2014/0350024 A1 | 11/2014 | LaVoie et al. |
| 2015/0011559 A1 | 1/2015 | LaVoie et al. |
| 2015/0133465 A1 | 5/2015 | LaVoie et al. |
| 2015/0307517 A1* | 10/2015 | LaVoie .............. C07D 413/12 514/253.04 |

FOREIGN PATENT DOCUMENTS

| | | |
|---|---|---|
| EP | 1078920 A1 | 2/2001 |
| EP | 1724262 A1 | 11/2006 |
| WO | WO 92/19242 A1 | 11/1992 |
| WO | WO 03/018017 A1 | 3/2003 |
| WO | WO 03/078397 A1 | 9/2003 |
| WO | WO 03/099274 A1 | 12/2003 |
| WO | WO 2004/000814 A1 | 12/2003 |
| WO | WO 2004/005472 A2 | 1/2004 |
| WO | WO 2004/018414 A2 | 3/2004 |
| WO | WO 2004/041210 A2 | 5/2004 |
| WO | WO 2004/073709 A1 | 9/2004 |
| WO | WO 2004/087145 A2 | 10/2004 |
| WO | WO 2005/075428 A1 | 8/2005 |
| WO | WO 2005/097100 A2 | 10/2005 |
| WO | WO 2006/067048 A1 | 6/2006 |
| WO | WO 2006/105289 A1 | 10/2006 |
| WO | WO 2007/107758 A1 | 9/2007 |
| WO | WO 2007/148093 A1 | 12/2007 |
| WO | WO 2008/016596 A2 | 2/2008 |
| WO | WO 2009/037485 A1 | 3/2009 |
| WO | WO 2009/040507 A1 | 4/2009 |
| WO | WO 2009/074810 A1 | 6/2009 |
| WO | WO 2009/074812 A1 | 6/2009 |
| WO | WO 2010/127307 A1 | 11/2010 |
| WO | WO 2011/112435 A1 | 9/2011 |
| WO | WO 2011/156626 A1 | 12/2011 |
| WO | WO 2012/142671 A1 | 10/2012 |

OTHER PUBLICATIONS

Akiba et al., "Preparation of 13-Substituted 8H-Dibenzo[a,g]quinolizin-8-onces by Intramolecular Wittig-Horner Reaction of Dialkyl 2-(o-Acyl-benzoyl)-1,2-dihydro-1-isoquinolylphosphonates", *Bull. Chem. Soc. Japan*, 57 (8), 2188-2192 (1984).

Augstein et al., "Synthesis of 11-Hydroxy-2,3,9,10-tetramethoxy-5,6,13,13a-tetrahydro-8H-dibenzo[α,δ]quinolizine. A Contribution to the Structure of Stepharotine", Stepharotine, vol. 34, no. 5, 1349-1352 (1969).

Bayer et al., "Pyridyl-substituierte Tetralonderivate: Eine neue Klasse nichtsteroidaler Aromatase-Inhibitoren", Arch. Pharm. 324, 815-820 (1991). [English Abstract].

Bedi et al., "Synthesis and biological activity of novel antibacterial quinazolines", *Bioorganic & Medicinal Chemistry Letters* 14, 5211-5213 (2004).

Beilstein, Database Beilstein Institute for Organic Chemistry, XP002591901, Database Accession No. 3834367 (BRN) abstract (1918).

Beilstein, Database Beilstein Institute for Organic Chemistry, XP002591900, Database Accession No. 3837583(BNR) abstract (1930).

Beuria, T.K. et al., "Sanguinarine Blocks Cytokinesis in Bacteria by Inhibiting FtsZ Assembly and Bundling", *Biochemistry*, 44, 16584-16593 (2005).

Bild et al., "Discovery of Inhibitors of MCF-7 Tumor Cell Adhesion to Endothelial Cells and Investigation on their Mode of Action", *Arch. Pharm. Pharm. Med. Chem.*, 337, 687-694 (2004).

Chen et al., "Synthesis and Antibacterial Evaluation of Certain Quinolone Derivatives", *J. Med. Chem.*, 44, 2374-2377 (2001).

Cole et al., "Potential Tumor-Selective Nitroimidazolylmethyluracil Prodrug Derivatives: Inhibitors of the Angiogenic Enzyme Thymidine Phosphorylase", *J. Med. Chem.*, 46, 207-209 (2003).

Database Registry [Online], Chemical Abstracts Service, XP002570845, Database accession No. 1043562-34-0/RN, abstract (2008).

Denes et al., "The chemistry of sanguinarine", XP002570844, Chemical Abstracts Service, Database accession No. 1960:91836, abstract, *Magyar Kemiai Folyoirat*, 64, 125-130 (1958).

Dyke et al., "The Chemistry of Cryptopine—I The Epicryptopines", *Tetrahedr0n*, vol. 24, No. 3, 1455-1465 (1968).

Dyke et al., "The Chemistry of Cryptopine—II Pseudocryptopine Chloride", *Tetrahedron*, vol. 25, 5375-5381 (1969).

Dykhuizen, "Santa Rosalia revisited: Why are there so many species of bacteria?", *Antonie van Leeuwenhock*, 73, 25-33 (1998).

Foroumadi et al., "Synthesis and in vitro antibacterial evaluation of N-[5-(5-nitro-2-thienyl)-1,3,4-thiadiazole-2-yl] piperazinyl quinolones", European Journal of Medicinal Chemistry, 38, 851-854 (2003).

Gopinath et al., "Dehydrogenation cyclization of 2-aryl-1-tetralone oxime acetates", XP002570843, Chemical Abstracts Service, Database accession No. 1960:23123, abstract, *Current Science*, 28, 241-242 (1959).

Huecas et al., "Protein Structure and Folding: The Interactions of Cell Division Protein FtsZ with Guanine Nucleotides", *J. Biol. Chem.*,282, 37515-37528 (2007).

Huttunen et al., "Prodrugs—An Efficient Way to Breach Delivery and Targeting Barriers", *Current Topics in Medicinal Chemistry* 11, 2265-2287 (2011).

Ishii et al., "Studies on the Chemical Constituents of Rutaceous Plants. LV.1 The Development of a Versatile Mehtod for the Synthesis of Antitumor-Active Benzo[c]phenanthridine Alkaloids. (5).1 A New Method for Quaternization of the Benzo[c]phenanthridine Nucleus", *Chem. Pharm. Bull.*, 32(8), 2984-2994 (1984).

Ito et al., "A medium-term rat liver bioassay for rapid in vivo detection of carcinogenic potential of chemicals", *Cancer Sci*, vol. 94 (1), 3-8 (2003).

Jackson et al., "Non-Steroidal Aromatase Inhibitors Based on a Biphenyl Scaffold: Synthesis, in vitro SAR, and Molecular Moedelling", *Chem Med Chem* 3, 603-618 (2008).

Jaiswal et al., "Totarol inhibits bacterial cytokinesis by perturbing the assembly dynamics of FtsZ", *Biochemistry*, vol. 46(14), 4211-4220 (2007).

Kaul et al., "A Bactericidal Guanidinomethyl Biaryl That Alters the Dynamics of Bacterial FtsZ Polymerization", *Journal of Medicinal Chemistry*, 55, 10160-10176 (2012).

Leroux et al., "N-(4-Biphenylmethyl)imidazoles as Potential Therapeutics for the Treatment of Prostate Cancer: Metabolic Robustness Due to Fluorine Substitution?", *Helvetica Chimica Acta*, vol. 86, 2671-2686 (2003).

Musser et al., "N-[(Arylmethoxy)phenyl] Carboxylic Acids, Hydroxamic Acids, Tetrazoles, and Sulfonyl Carboxamides. Potent Orally Active Leukotriene D4 Antagonists of Novel Structure", *J. Med. Chem.* 33, 24-245 (1990).

Nicolson et al., "Potentiation of methicillin activity against methicillin-resistant *Staphylococcus aureus* by diterpenes", *FEMS Microbiology Letters* 179, 233-239 (1999).

Okudaira et al., "A Study of the Intestinal Absorption of an Ester-Type Prodrug, ME3229, in Rats: Active Efflux Transport as a Cause of Poor Bioavailability of the Active Drug", *Journal of Pharmacology and Experimental Therapeutics*, vol. 294 (2), 580-587 (2000).

(56) References Cited

OTHER PUBLICATIONS

Patent Cooperation Treaty, International Searching Authority, Search Report and Written Opinion for PCT/US2013/033343, 12 pages, Jun. 13, 2013.
Roesch et al., "Synthesis of isoquinolines and pyridines by the palladium-catalyzed iminoannulation of internal alkynes", *J. Org. Chem.* 66, 8042-8051 (2001).
Sanders et al., "Selective Cytotoxicity of Topoisomerase-Directed Protoberberines against Glioblastoma Cells", *Biochemical Pharmacology*, vol. 56, 1157-1166 (1998).
Sethi, "Enzyme Inhibition VIII: Mode of Inhibition of Reverse Transcriptase Activity by Analogues, Isomers, and Related Alkaloids of Coralyne", *Journal of Pharmaceutical Sciences*, vol. 74 (8), 889-891 (1985).
Singh et al., "Structure—Activity Relationship Studies Leading to the Identification of (2E)-3-[I-[(2,4-Dichlorophenyl)methyl]-5-fluoro-3-methyl-1H-indol-7-yl]-N-[(4,5-dichloro-2-thienyl)sulfonyl]-2-propenamide (DG-041), a Potent and Selective Prostanoid EP3 Receptor Antagonist, as a Novel Antiplatelet gent that Does not Prolong Bleeding", *J. Med. Chem.* 53, 18-36 (2010).
Wachall et al., "Imidazole Substituted Biphenyls: A New Class of Highly Potent and In Vivo Active Inhibitors of P450 17 as Potential Therapeutics for Treatment of Prostate Cancer", *Bioorganic & Medicinal Chemistry* 7, 1913-1924 (1999).
Wigbers et al., "Synthesis, Structures, and Aggregation Properties of N-Acylamidines", *Eur. J. Org. Chem.*, 861-877 (2011).
Wu et al., "Regulatory perspectives of Type II prodrug development and time-dependent toxicity management: Nonclinical Pharm/Tox analysis and the role of comparative toxicology", *Toxicology* 236, 1-6 (2007).

Yaeko et al., "Studies on the constituents of Bocconia Cordata. IV. Transformation of sanguinarine into bocconine", XP002570841, Chemical Abstracts Service, Database accession No. 1992:129332, abstract, *Journal of Heterocyclic Chemistry*, 28(8), 1841-1843 (1991).
Yamaguchi et al., "Utilization of Protopine and Related Alkaloids. XIV. Oxidation of the Photo-adduct of 1-Oxoanhydromethylberberine with Nitrosobenzene, and Synthesis of Ring C-Substituted Benzo[c]phenanthridines", *Chem. Pharm. Bull.*, 31(5), 1601-1611 (1983).
Chemical Abstracts Database, "RN 1375188-04-7 for N-(Methylsulfonyl)-3-[(2-methyl-4-thiazolyl)methoxy]-Benzamide", 1 page, (2012).
Elsen, et al., "Mechanism of Action of the Cell-Division Inhibitor PC190723: Modulation of FtsZ Assembly Cooperativity", Journal of American Chemical Society 134, 12342-12345 (2012).
Kaul, et al., "Enterococcal and streptococcal resistance to PC190723 and related coumpounds: Molecular insights from a FtsZ mutational analysis", Biochimie 95, 1880-1887 (2013).
Kaul, et al., "Pharmacokinetics and in vivo antistaphylococcal efficacy of TXY 541, a 1-methylpiperidine-4-carboxamide prodrug of PC190723", Biochemical Pharmacology 86, 1699-1707 (2013).
Online:, "http://web.archive.org/web/20070630171813/http://www.enamine.net/index.php?option=com_content&task=view&id=22&menuid=51&PHPSESSID=64a4f248f69d671a413f487bb62c4d90", dated Jun. 30, 2007, 1 page, accessed Apr. 1, 2015.
Pitt, et al., "Heteroaromatic Rings of the Future", J. Med. Chem. 52, 2952-2963 (2009).
Pozharskii, et al., "Heterocycles in Life and Society. An Introduction to Heterocyclic Chemistry and Biochemistry and the Role of Heterocycles in Science, Technology, Medicine and Agriculture", Wiley, pp. 1-6 (1997).

\* cited by examiner

ANTIMICROBIAL AGENTS

RELATED APPLICATIONS

This application is a 371 national stage application of PCT/US2013/033343 filed 21 Mar. 2013, which claims priority to U.S. Provisional Application No. 61/613,903 filed on 21 Mar. 2012, all of which are incorporated by reference in their entirety.

PRIORITY OF INVENTION

This application claims priority to U.S. Provisional Application No. 61/613,903, filed 21 Mar. 2012. The entire content of this provisional application is hereby incorporated by reference herein.

BACKGROUND OF THE INVENTION

The emergence of Multidrug Resistant (MDR) bacterial pathogens (e.g. methicillin-resistant *Staphylococcus aureus* (MRSA), *Acinetobacter baumannii-calcoaceticus* complex (ABC), etc.) has increased concerns as to the adequacy of current antimicrobials and pathogen treatment methods. The lethality of such pathogens, particularly MRSA, has often led to treatment methods that are experimental or would otherwise normally be avoided in standard clinical practice. For example, the antibiotic colistin was traditionally considered too nephrotoxic and neurotoxic for clinical use, but is nevertheless used to treat many MDR bacterial infections due to a paucity of available active drugs. The growing threat from MDR pathogens highlights a critical need for additional antimicrobials. In this connection, there is a pressing need for new antibiotics that exhibit novel mechanisms of action or that are able to circumvent known resistance pathways.

Elements of the bacterial cell division machinery present appealing targets for antimicrobial compounds because (i) they are essential for bacterial viability, (ii) they are widely conserved among bacterial pathogens, and (iii) they often have markedly different structures than their eukaryotic homologs. One such protein that has been identified as a potential target is the FtsZ protein. During the division process, FtsZ, along with approximately 15 other proteins, assemble at mid-cell into a large cell division complex (termed the divisome), ultimately facilitating cell cytokinesis. More importantly, FtsZ is widely conserved among many bacterial strains.

International Patent Application Publication Number WO 2007/107758 discusses certain compounds of the following formula:

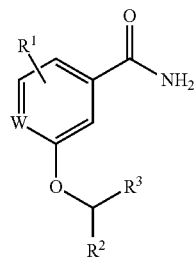

wherein W, $R^1$, $R^2$, and $R^3$ have the values defined in the application; the compounds are reported to have antibiotic activity. Unfortunately, certain of the compounds discussed in this publication have solubility properties that may severely limit their use as pharmaceutical agents. Accordingly, there remains a need for antibacterial compounds that have physical properties (e.g. solubility) that make them useful as pharmaceutical agents.

SUMMARY OF THE INVENTION

Applicant has identified a series of antibiotic compounds that are highly soluable and that can be formulated for administration as antibiotic agents. Accordingly, in one embodiment the invention provides a compound of the invention which is a compound of formula (I):

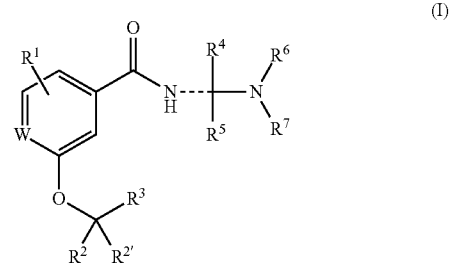

wherein:

$R^1$ is hydrogen or 1, 2 or 3 optional substituents;

W is $CR^a$, or N;

$R^a$ is absent (e.g. when W is N), hydrogen, or an optional substituent, $R^2$ is hydrogen, methyl, or fluoro, and $R^{2'}$ is hydrogen, $(C_1-C_6)$alkyl, $(C_2-C_6)$alkenyl, $(C_2-C_6)$alkynyl, $(C_3-C_8)$cycloalkyl, aryl, or 5-6 membered heterocyclyl, wherein each alkyl, alkenyl, alkynyl, cycloalkyl, aryl, or heterocyclyl may be optionally substituted with one or more $R^b$;

or $R^a$ and $R^2$ taken together are —$CH_2$—, —$CH_2$—$CH_2$—, —O—, —O—$CH_2$—, —$CH_2$O—, —O—$CH_2$—$CH_2$—, or —$CH_2$—$CH_2$—O—;

or $R^a$ is absent (e.g. when W is N), hydrogen, or an optional substituent, and $R^{2'}$ taken together with $R^2$ is cyclopropyl, cyclobutyl, azetidine, or =CH—N$(R^c)_2$; wherein the cyclopropyl, cyclobutyl, and azetidine can optionally be substituted with $(C_1-C_6)$alkyl;

$R^3$ is -(Alk$^1$)$_m$-(Z)$_p$-(Alk$^2$)$_n$-Q;

Z is —O—, —S—, —S(O)—, —$SO_2$—, —NH—, —N(CH$_3$)—, —N(CH$_2$CH$_3$)—, —C(=O)—, —OC(=O)—, —C(=O)O—, or an optionally substituted divalent monocyclic carbocycle or heterocyclic radical having 3 to 6 ring atoms, or an optionally substituted divalent bicyclic heterocyclic radical having 5 to 10 ring atoms;

Alk$^1$ is optionally substituted $(C_1-C_6)$alkylene, $(C_2-C_6)$alkenylene, or $(C_1-C_6)$alkynylene radical, which may optionally terminate with or be interrupted by —O—, —S—, —S(O)—, —$SO_2$—, —NH—, —N(CH$_3$)—, —N(CH$_2$CH$_3$)—;

Alk$^2$ is optionally substituted $(C_1-C_6)$alkylene, $(C_2-C_6)$alkenylene, or $(C_1-C_6)$alkynylene radical, which may optionally terminate with or be interrupted by —O—, —S—, —S(O)—, —$SO_2$—, —NH—, —N(CH$_3$)—, —N(CH$_2$CH$_3$)—;

Q is hydrogen, halo, cyano, or hydroxyl, or an optionally substituted monocyclic carbocyclic or heterocyclic radical having 3 to 7 ring atoms, or an optionally substituted divalent bicyclic heterocyclic radical having 5 to 10 ring atoms;

the bond represented by ---- is a double bond, $R^4$ is hydrogen or methyl, and $R^5$ is absent; or the bond represented by ---- is a single double bond, $R^4$ is H, optionally substituted divalent monocyclic carbocycle, or heterocyclic radical having 3 to 6 ring atoms, and $R^5$ is hydrogen; wherein each optionally substituted divalent monocyclic carbocycle, or heterocyclic radical having 3 to 6 ring atoms of $R^4$ is optionally substitutes with one or more (e.g. 1, 2, or 3) substituents independently selected from $(C_1-C_6)$alkoxy, halo, hydroxy, cyano, nitro, amino, methylamino, dimethylamino, carboxy, $(C_1-C_6)$alkoxycarbonyl, aminocarbonyl, $(C_1-C_6)$alkanoylamino, or tetrazole;

$R^6$ and $R^7$ are each independently hydrogen, $(C_1-C_6)$alkyl, $(C_2-C_6)$alkenyl, $(C_2-C_6)$alkynyl, or a heterocyclic radical having 3 to 6 ring atoms, or $R^6$ and $R^7$ together with the nitrogen to which they are attached form a 5 or 6 membered heterocyclic ring (e.g. a aziridino, azetidino, morpholino, thiomorpholino, piperazino, pyrrolidino imidazoyl, or piperidino ring), which ring is optionally substituted with one or more groups independently selected from $(C_1-C_6)$alkyl; wherein any $(C_1-C_6)$alkyl of $R^6$ and $R^7$ is optionally substituted with one or more (e.g. 1, 2, or 3) substituents independently selected from $(C_1-C_6)$alkoxy, halo, hydroxy, cyano, nitro, amino, methylamino, dimethylamino, oxo (=O), carboxy, $(C_1-C_6)$alkoxycarbonyl, aminocarbonyl, $(C_1-C_6)$alkanoylamino, aryl, or tetrazole; and wherein any aryl or heterocyclic radical having 3 to 6 ring atoms of $R^6$ and $R^7$ is optionally substituted with one or more (e.g. 1, 2, or 3) substituents independently selected from $(C_1-C_6)$alkyl, $(C_1-C_6)$alkoxy, halo, trifluoromethyl, trifluoromethoxy, hydroxy, cyano, nitro, tetrazole, carboxy, $(C_1-C_6)$alkoxycarbonyl, or a $(C_1-C_4)$alkyl that is optionally substituted with one or more (e.g. 1, 2, or 3) substituents independently selected from $(C_1-C_6)$alkoxy, halo, hydroxy, cyano, nitro, tetrazole, carboxy, $(C_1-C_6)$alkoxycarbonyl, amino, methylamino, dimethylamino, or oxo (=O);

each $R^b$ is independently $R^f$, $OR^e$, —C(=O)$R^e$, —OC(=O)$R^e$, —C(=O)O$R^e$, —N($R^e$)$_2$, —N$R^e$C(=O)$R^d$, —C(=O)N($R^e$)$_2$, —N$R^e$C(=O)O$R^d$, —OC(=O)N($R^e$)$_2$, —C(=O)N($R^e$)—N($R^e$)C(=O)$R^d$, —NHC(=O)NH$R^d$, —NHS(O)$_{0-2}R^d$, —S(O)$_{0-2}R^d$, —OS(O)$_{0-2}R^d$, —OP(=O)(O$R^e$)$_2$, or —P(=O)(O$R^e$)$_2$;

each $R^c$ is independently H or $(C_1-C_6)$alkyl;

each $R^d$ is optionally substituted and is independently selected from $(C_1-C_6)$alkyl, $(C_2-C_6)$alkenyl, $(C_2-C_6)$alkynyl, aryl, aryl$(C_1-C_6)$alkyl, 4-10 membered heterocyclyl and heterocyclyl$(C_1-C_6)$alkyl;

each $R^e$ is independently selected from H, $(C_1-C_6)$alkyl, $(C_2-C_6)$alkenyl, $(C_2-C_6)$alkynyl, aryl, aryl$(C_1-C_6)$alkyl, 4-10 membered heterocyclyl and heterocyclyl$(C_1-C_6)$alkyl, wherein each $(C_1-C_6)$alkyl, $(C_2-C_6)$alkenyl, $(C_2-C_6)$alkynyl, aryl, aryl$(C_1-C_6)$alkyl, 4-10 membered heterocyclyl and heterocyclyl$(C_1-C_6)$alkyl is optionally substituted;

each $R^f$ is optionally substituted and is independently selected from aryl and 4-10 membered heterocyclyl; and m, p, and n are each independently 0 or 1, provided that at least one of m, p, and n is 1; or a salt thereof. It is understood that when the bond represented by ---- is a double bond, the hydrogen on the attached nitrogen in formula (I) is absent.

The invention also provides a method for treating a bacterial infection in a mammal comprising administering to the mammal an effective amount of a compound of formula I or a pharmaceutically acceptable salt thereof.

The invention also provides a composition comprising a compound of formula I, or a pharmaceutically acceptable salt thereof, and a pharmaceutically acceptable vehicle.

The invention also provides a compound of formula I or a pharmaceutically acceptable salt thereof for the prophylactic or therapeutic treatment of a bacterial infection.

The invention also provides a compound of formula I or a pharmaceutically acceptable salt thereof for use in medical treatment.

The invention also provides the use of a compound of formula I or a pharmaceutically acceptable salt thereof for the preparation of a medicament for treating a bacterial infection in a mammal.

The invention also provides processes and intermediates disclosed herein that are useful for preparing compounds of formula I or salts thereof.

DETAILED DESCRIPTION

The following definitions are used, unless otherwise described: halo is fluoro, chloro, bromo, or iodo. Alkyl and alkoxy, etc. denote both straight and branched groups but reference to an individual radical such as propyl embraces only the straight chain radical (a branched chain isomer such as isopropyl being specifically referred to.

As used herein, the term "$(C_a-C_b)$alkyl" wherein a and b are integers refers to a straight or branched chain alkyl radical having from a to b carbon atoms. Thus when a is 1 and b is 6, for example, the term includes methyl, ethyl, n-propyl, isopropyl, n-butyl, isobutyl, sec-butyl, t-butyl, n-pentyl and n-hexyl.

As used herein the term "divalent $(C_a-C_b)$alkylene radical" wherein a and b are integers refers to a saturated hydrocarbon chain having from a to b carbon atoms and two unsatisfied valences. The term includes, for example, methylene, ethylene, n-propylene and n-butylene.

As used herein the term "$(C_a-C_b)$alkenyl" wherein a and b are integers refers to a straight or branched chain alkenyl moiety having from a to b carbon atoms having at least one double bond of either E or Z stereochemistry where applicable. The term includes, for example, vinyl, allyl, 1- and 2-butenyl and 2-methyl-2-propenyl.

As used herein the term "divalent $(C_a-C_b)$alkenylene radical" means a hydrocarbon chain having from a to b carbon atoms, at least one double bond, and two unsatisfied valences. The term includes, for example, —CH=CH— (vinylene), —CH=CH—CH$_2$—, —CH$_2$—CH=CH—, —CH=CH—CH$_2$—CH$_2$—, —CH=CH—CH$_2$—CH$_2$—CH$_2$—, —CH=CH—CH=CH—, —CH=CH—CH=CH—CH$_2$—, —CH=CH—CH=CH—CH$_2$—CH$_2$—, —CH=CH—CH$_2$—CH=CH—, and —CH=CH—CH$_2$—CH$_2$—CH=CH—.

As used herein the term "$(C_a-C_b)$alkynyl" wherein a and b are integers refers to straight chain or branched chain hydrocarbon groups having from a to b carbon atoms and having in addition at least one triple bond. This term would include for example, ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl.

As used herein the term "divalent $(C_a-C_b)$alkynylene radical" wherein a and b are integers refers to a divalent hydrocarbon chain having from a to b carbon atoms, and at least one triple bond. The term includes, for example, —C≡C—, —C≡C=CH$_2$—, and —CH$_2$—C≡C—.

As used herein the term "carbocycle" includes both aryl and cycloalkyl.

As used herein the unqualified term "aryl" refers to a mono- or bi-cyclic carbocyclic aromatic radical. Illustrative of such radicals are phenyl and naphthyl.

As used herein the term "cycloalkyl" refers to a monocyclic or bridged monocyclic saturated carbocyclic radical having from 3-8 carbon atoms and includes, for example, cyclopropyl, cyclobutyl, cyclopentyl, cyclohexyl, cycloheptyl, cyclooctyl and bicyclo[2.2.1]hept-1-yl.

As used herein the unqualified term "aryl" refers to a mono- or bi-cyclic carbocyclic aromatic radical. Illustrative of such radicals are phenyl and naphthyl.

As used herein the unqualified term "heteroaryl" refers to a mono-, or bi-cyclic aromatic radical containing one or more heteroatoms selected from S, N and O, and includes radicals having two such monocyclic rings, or one such monocyclic ring and one monocyclic aryl ring, which are fused or directly linked by a covalent bond. Illustrative of such radicals are thienyl, benzthienyl, furyl, benzfuryl, pyrrolyl, imidazolyl, benzimidazolyl, thiazolyl, benzthiazolyl, thiazolopyridinyl, isothiazolyl, benzisothiazolyl, pyrazolyl, oxazolyl, benzoxazolyl, isoxazolyl, benzisoxazolyl, isothiazolyl, triazolyl, benztriazolyl, thiadiazolyl, oxadiazolyl, pyridinyl, pyridazinyl, pyrimidinyl, pyridazinyl, triazinyl, indolyl and indazolyl.

As used herein the unqualified term "heterocyclyl" or "heterocyclic" includes "heteroaryl" as defined above, and in addition means a mono-, or bi-cyclic non-aromatic radical containing one or more heteroatoms selected from S, N and O. Illustrative of such radicals are pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyrimidinyl, morpholinyl, piperazinyl, indolyl, morpholinyl, benzfuranyl, pyranyl, isoxazolyl, benzimidazolyl, methylenedioxyphenyl, ethylenedioxyphenyl, maleimido and succinimido groups.

Unless otherwise specified in the context in which it occurs, the term "substituted" as applied to any moiety herein, means substituted with up to four compatible "optional substituents," each of which independently may be, for example, $(C_1-C_6)$alkyl, $(C_2-C_6)$alkenyl, $(C_2-C_6)$alkynyl, $(C_1-C_6)$alkoxy, hydroxyl, hydroxy$(C_1-C_6)$alkyl, mercapto, mercapto$(C_1-C_6)$alkyl, $(C_1-C_6)$alkylthio, halo, fully or partially fluorinated $(C_1-C_3)$alkyl, fully or partially fluorinated $(C_1-C_3)$alkoxy, fully or partially fluorinated $(C_1-C_3)$ alkylthio, nitro, cyano, oxo, phenyl, phenoxy, monocyclic heteroaryl or heteroaryloxy with 5 or 6 ring atoms, —COOR$^A$—, —COR$^A$—, —OCOR$^A$—, —SO$_2$R$^A$—, —CONR$^A$R$^B$—, —SO$_2$NR$^A$R$^B$—, —NR$^A$R$^B$—, —OCON-R$^A$R$^B$—, —NR$^B$COR$^A$—, —NR$^B$COOR$^A$—, —NR$^B$—SO$_2$OR$^A$—, or —NR$^A$CONR$^A$R$^B$—, wherein R$^A$ and R$^B$ are independently hydrogen or a $(C_1-C_6)$alkyl group or, in the case where R$^A$ and R$^B$ are linked to the same N atom, R$^A$ and R$^B$ taken together with that nitrogen may form a cyclic amino ring. Where the substituent is phenyl, phenoxy or monocyclic heteroaryl or heteroaryloxy with 5 or 6 ring atoms, the phenyl or heteroaryl ring thereof may itself be substituted by any of the above substituents except phenyl phenoxy, heteroaryl or heteroaryloxy. An "optional substituent" or "substituent" may be one of the foregoing specified groups.

As used herein the term "salt" includes base addition, acid addition and quaternary salts. Compounds of the invention which are acidic can form salts, including pharmaceutically acceptable salts, with bases such as alkali metal hydroxides, e.g. sodium and potassium hydroxides; alkaline earth metal hydroxides e.g. calcium, barium and magnesium hydroxides; with organic bases e.g. N-methyl-D-glucamine, choline tris(hydroxymethyl)amino-methane, L-arginine, L-lysine, N-ethyl piperidine, dibenzylamine and the like. Those compounds (I) which are basic can form salts, including pharmaceutically acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic, p-toluenesulphonic, benzoic, benzenesulfonic, glutamic, lactic, and mandelic acids and the like. For a review on suitable salts, see Handbook of Pharmaceutical Salts Properties, Selection, and Use by Stahl and Wermuth (Wiley-VCH, Weinheim, Germany, 2002).

The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

In one embodiment of the invention the compound of formula (I) is a compound of formula (Ia):

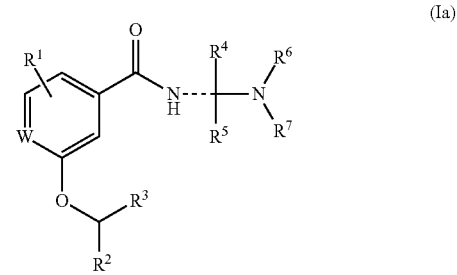

(Ia)

wherein:
$R^1$ is hydrogen or 1, 2 or 3 optional substituents;
W is CR$^a$, or N;
$R^a$ is hydrogen or 1, 2 or 3 optional substituents, and $R^2$ is hydrogen, methyl, or fluoro; or $R^a$ and $R^2$ taken together are —CH$_2$—, —CH$_2$—CH$_2$—, —O—, —O—CH$_2$—, —CH$_2$O—, —O—CH$_2$—CH$_2$—, or —CH$_2$—CH$_2$—O—;
$R^3$ is -(Alk$^1$)$_m$-(Z)$_p$-(Alk$^2$)$_n$-Q;
Z is —O—, —S—, —S(O)—, —SO$_2$—, —NH—, —N(CH$_3$)—, —N(CH$_2$CH$_3$)—, —C(=O)—, —OC(=O)—, —C(=O)O—, or an optionally substituted divalent monocyclic carbocycle or heterocyclic radical having 3 to 6 ring atoms, or an optionally substituted divalent bicyclic heterocyclic radical having 5 to 10 ring atoms;
Alk$^1$ is optionally substituted $(C_1-C_6)$alkylene, $(C_2-C_6)$alkenylene, or $(C_1-C_6)$alkynylene radical, which may optionally terminate with or be interrupted by —O—, —S—, —S(O)—, —SO$_2$—, —NH—, —N(CH$_3$)—, —N(CH$_2$CH$_3$)—;
Alk$^2$ is optionally substituted $(C_1-C_6)$alkylene, $(C_2-C_6)$alkenylene, or $(C_1-C_6)$alkynylene radical, which may optionally terminate with or be interrupted by —O—, —S—, —S(O)—, —SO$_2$—, —NH—, —N(CH$_3$)—, —N(CH$_2$CH$_3$)—;
Q is hydrogen, halo, cyano, or hydroxyl, or an optionally substituted monocyclic carbocyclic or heterocyclic radical having 3 to 7 ring atoms, or an optionally substituted divalent bicyclic heterocyclic radical having 5 to 10 ring atoms;
the bond represented by ---- is a double bond, $R^4$ is hydrogen, and $R^5$ is absent; or the bond represented by ---- is a single double bond and $R^4$ and $R^5$ are each hydrogen;
$R^6$ and $R^7$ are each independently hydrogen, $(C_1-C_6)$alkyl, or benzyl, or $R^6$ and $R^7$ together with the nitrogen to which they are attached form a aziridino, azetidino, morpholino, thiomorpholino, piperazino, pyrrolidino or piperidino ring, which ring is optionally substituted with one or more groups independently selected from $(C_1-C_6)$alkyl; wherein any $(C_1-C_6)$alkyl of $R^6$ and $R^7$ is optionally substituted with one or more (e.g. 1, 2, or 3) substituents independently selected from $(C_1-C_6)$alkoxy, halo, hydroxy, cyano, nitro, amino, methylamino, dimethylamino, oxo (=O), carboxy, $(C_1-C_6)$alkoxycarbonyl, aminocarbonyl, $(C_1-C_6)$alkanoylamino, or tetrazole; and wherein any benzyl of $R^6$ and $R^7$ is optionally substituted with one or more (e.g. 1, 2, or 3) substituents independently selected from $(C_1-C_6)$alkyl, $(C_1-C_6)$alkoxy, halo, trifluoromethyl, trifluoromethoxy, hydroxy, cyano, nitro, tetrazole, carboxy, $(C_1-C_6)$alkoxycarbonyl, or a $(C_1-C_4)$alkyl that is optionally substituted with one or more (e.g. 1, 2, or 3) substituents independently selected from $(C_1-C_6)$alkoxy, halo, hydroxy, cyano, nitro, tetrazole, carboxy, $(C_1-C_6)$alkoxycarbonyl, amino, methylamino, dimethylamino, or oxo (=O); and m, p, and n are each independently 0 or 1, provided that at least one of m, p, and n is 1;

or a salt thereof.

In one embodiment of the invention the compound of formula (I) is a compound of formula (Ib):

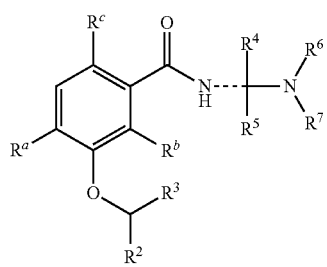

(Ib)

wherein:
$R^b$ and $R^c$ are independently fluoro or chloro, or one of $R^b$ and $R^c$ is hydrogen while the other is fluoro or chloro; or a salt thereof.

In one embodiment of the invention the compound of formula (I) is a compound of formula (Ic):

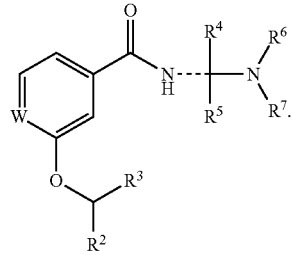

(Ic)

In one embodiment of the invention $R^a$ and $R^2$ are hydrogen.

In one embodiment of the invention $R^a$ is hydrogen or an optional substituent, $R^{2'}$ is hydrogen, methyl, or fluoro, and $R^2$ is $(C_1-C_6)$alkyl, $(C_2-C_6)$alkenyl, $(C_2-C_6)$alkynyl, $(C_3-C_8)$cycloalkyl, aryl, or 5-6 membered heterocyclyl, wherein each alkyl, alkenyl, alkynyl, cycloalkyl, aryl, or heterocyclyl may be optionally substituted with one or more $R^b$.

In one embodiment of the invention $R^a$ is hydrogen, $R^{2'}$ is hydrogen, methyl, or fluoro, and $R^2$ is $(C_1-C_6)$alkyl, $(C_2-C_6)$alkenyl, $(C_2-C_6)$alkynyl, $(C_3-C_8)$cycloalkyl, aryl, or 5-6 membered heterocyclyl, wherein each alkyl, alkenyl, alkynyl, cycloalkyl, aryl, or heterocyclyl may be optionally substituted with one or more $R^b$.

In one embodiment of the invention $R^a$ and $R^2$ taken together are —CH$_2$—, —CH$_2$—CH$_2$—, —O—, —O—CH$_2$—, —CH$_2$O—, —O—CH$_2$—CH$_2$—, or —CH$_2$—CH$_2$—O—.

In one embodiment of the invention $R^a$ is hydrogen or an optional substituent, and $R^{2'}$ taken together with $R^2$ is cyclopropyl, cyclobutyl, or =CH—N(R$^c$)$_2$.

In one embodiment of the invention $R^a$ is hydrogen, and $R^{2'}$ taken together with $R^2$ is cyclopropyl, cyclobutyl, or =CH—N(R$^c$)$_2$.

In one embodiment of the invention $R^a$ is hydrogen or an optional substituent, and $R^{2'}$ taken together with $R^2$ is =CH—N(R$^c$)$_2$.

In one embodiment of the invention $R^a$ is hydrogen, and $R^{2'}$ taken together with $R^2$ is =CH—N(R$^c$)$_2$.

In the radical $R^3$ p may be 0, and m and/or n may be 1. Alternatively, p may be 1, and Z may be an optionally substituted carbocyclic or heteroaryl radical having 3 to 6 ring atoms or an optionally substituted bicyclic carbocyclic or heteroaryl radical having 5 to 10 ring atoms, which is linked to the -(Alk$^1$)$_m$- part of $R^3$ and to the -(Alk$^2$)$_n$-Q part of $R^3$ via ring carbon or nitrogen atoms.

Examples of divalent radicals Z in this embodiment include those selected from the following, in either orientation:

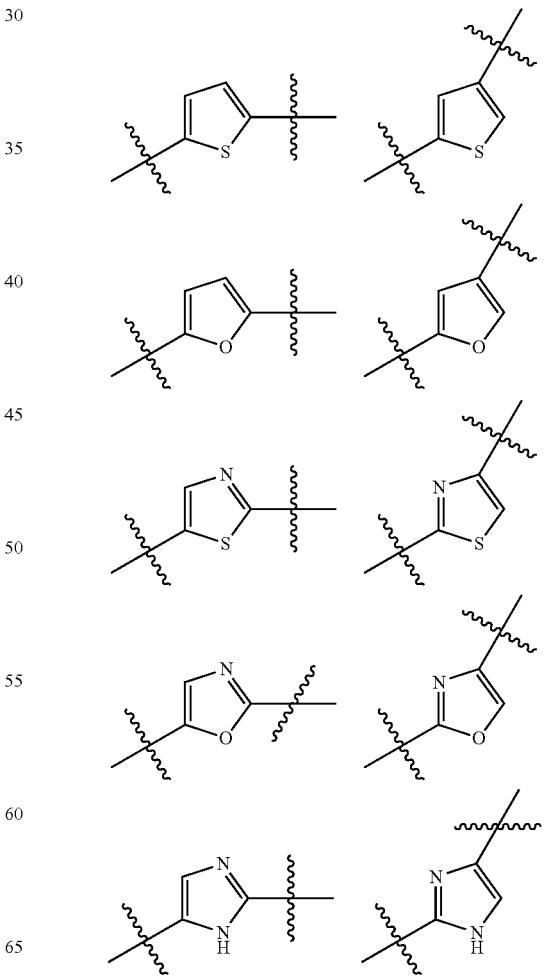

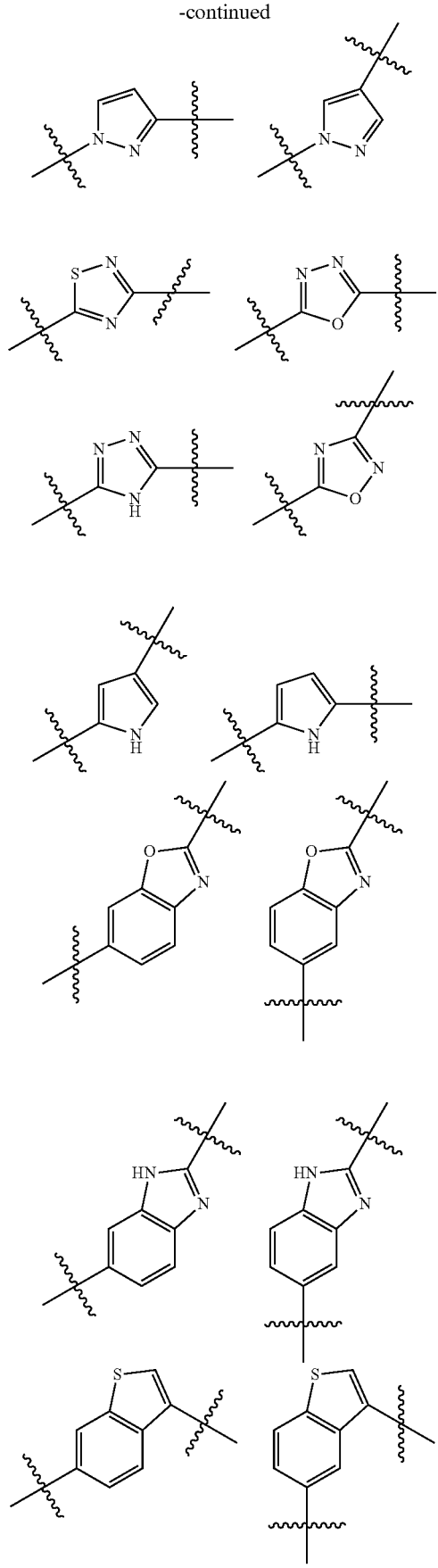
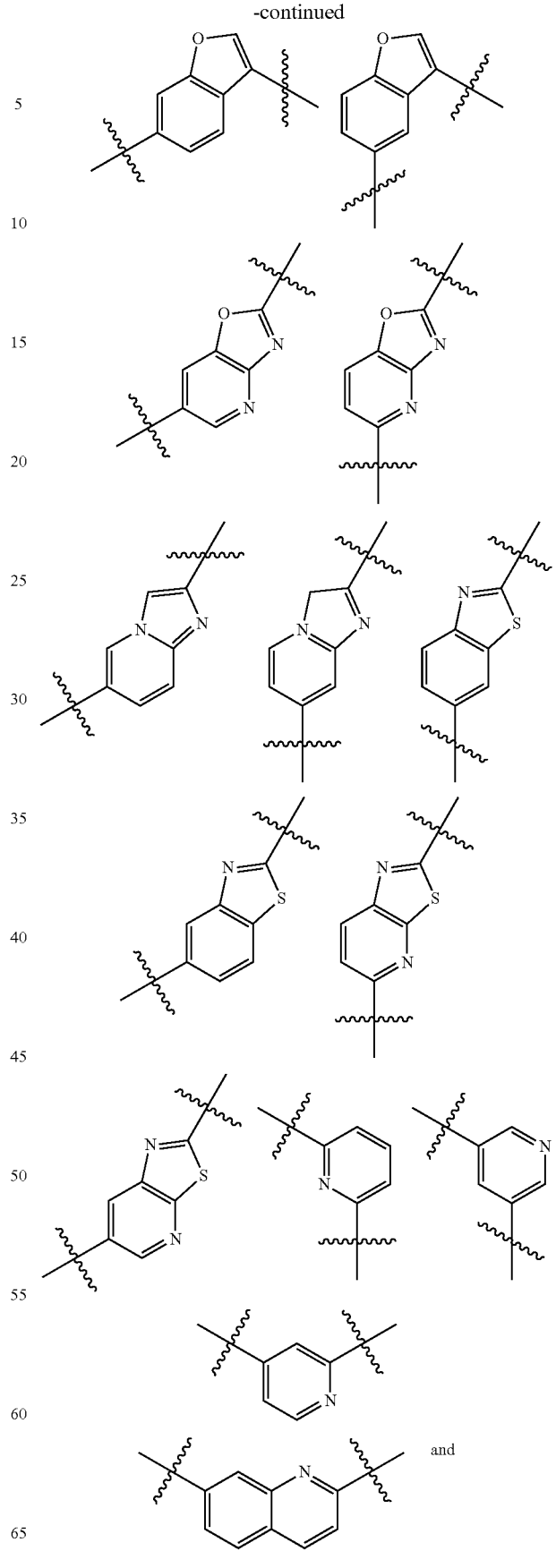

-continued

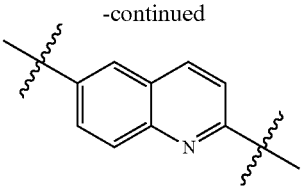

In another alternative embodiment p is 1, and Z is an optionally substituted monocyclic non-aromatic carbocyclic or heterocyclic radical having 3 to 6 ring atoms or an optionally substituted bicyclic non-aromatic carbocyclic or heterocyclic having 5 to 10 ring atoms, which is linked to the -(Alk$^1$)$_m$- part of R$_3$ and to the -(Alk$^2$)$_n$-Q part of R$_3$ via ring carbon or nitrogen atoms. Examples of Z radicals, which are optionally substituted, in this embodiment include those selected from the following, in either orientation:

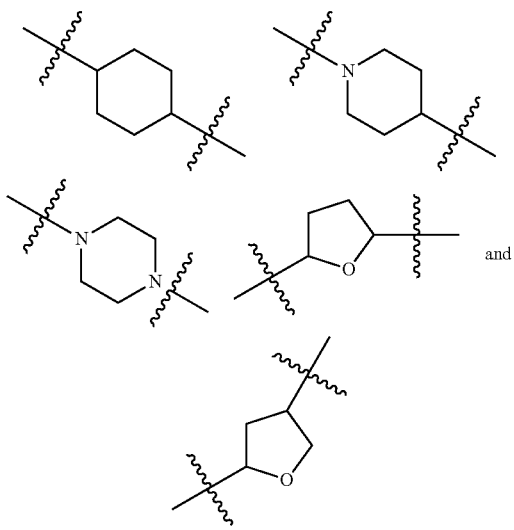

In the compounds with which the invention is concerned, and in any of the subclasses or embodiments of such compounds discussed above, Q may be hydrogen. However Q may also be a radical selected from any of the divalent Z radicals specifically identified above but with one of the unsatisfied valencies thereof satisfied with hydrogen or an optional substituent.

In the compounds with which the invention is concerned, and in any of the subclasses or embodiments of such compounds discussed above n and/or m may be 0. In all compounds and classes of compounds with which the invention is concerned, it is typical that the radical R$_3$, when fully extended, does not exceed the length of an unbranched saturated hydrocarbon chain of 14 carbon atoms, ie does not exceed about 16 Angstroms. For example, that length may be equivalent to that of an unbranched saturated hydrocarbon chain of from 6 to 12, or 9 to 12 carbon atoms, ie from about 6 to about 14, and from about 10 to about 14 Angstroms respectively.

In the compounds with which the invention is concerned, Alk$^1$ and Alk$^2$ when present, may be, for example, optionally substituted straight chain (C$_1$-C$_6$)alkylene, (C$_2$-C$_6$)alkenylene, or (C$_2$-C$_6$)alkynylene radicals, each of which may optionally terminate or be interrupted by —O—, —S—, —S(O)—, —SO$_2$—, —NH—, —N(CH$_3$)—, —N(CH$_2$CH$_3$)—, —C(=O)—, —OC(=O)—, or —C(=O)O—.

Any additional optional substituents R$^1$ and any optional substituents present in Alk$^1$, Alk$^2$, Z, and Q may be selected from, for example, methyl, —OCH$_3$, —CF$_3$, —OCF$_3$—, ethyl, cyclopropyl, oxo, hydroxyl, fluoro, chloro, bromo, cyano, acetyl, amino, methylamino, dimethylamino, acetylamino, carbamate, —CONH$_2$, —COOH, and —CH$_2$OH—.

Compounds of formula (Id) per se, and salts, hydrates or solvates thereof constitute a distinct aspect of the invention:

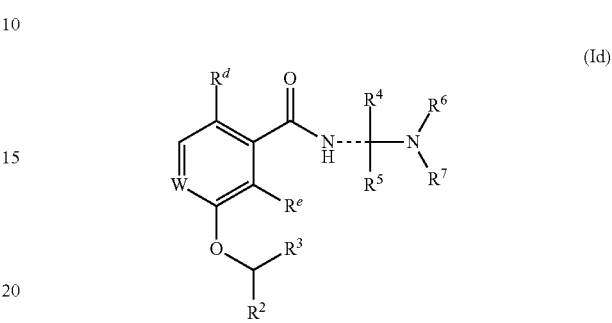

(Id)

wherein:

W is CR$^a$, or N;

R$^a$ is hydrogen or 1, 2 or 3 optional substituents, and R$^2$ is hydrogen, methyl, or fluoro; or R$^a$ and R$^2$ taken together are —CH$_2$—, —CH$_2$—CH$_2$—, —O—, —O—CH$_2$—, —CH$_2$O—, —O—CH$_2$—CH$_2$—, or —CH$_2$—CH$_2$—O—;

R$^d$ and R$^e$ are independently fluoro or chloro, or one of R$^d$ and R$^e$ is hydrogen while the other is fluoro or chloro;

R$^3$ is a radical selected from:

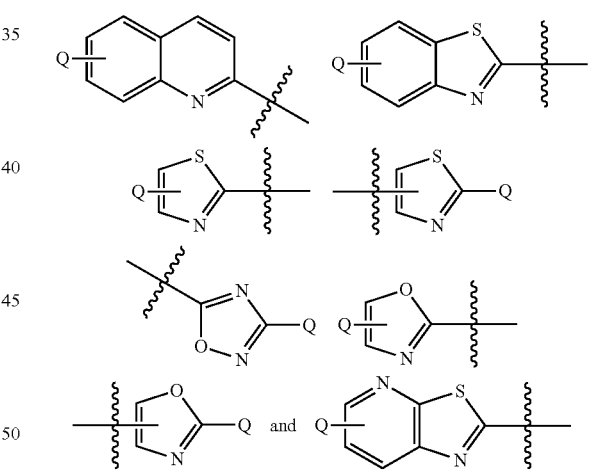

in which any vacant ring position is optionally substituted; and

Q has any of the values defined herein, wherein any unsubstituted ring carbon is optionally substituted;

or a salt thereof.

In compounds (Ie) it is currently preferred that W be =CH— and R$_2$ be hydrogen.

In compounds (Ie) Q in radical R$_3$ may be hydrogen or optionally substituted phenyl.

In a particular subset of compounds (Ie), R$_3$ is optionally substituted quinolin-2-yl, benzothiazol-2-yl, thiazol-2-yl, thiazol-4-yl, thiazol-5-yl, oxadiazol-3-yl, oxadiazol-5-yl, oxazol-2-yl, oxazol-4-yl, oxazol-5-yl or thiazolopyridin-2-yl.

Optional substituents which may be present in $R_3$ in the compound per se aspect of the invention include methyl, —$OCH_3$, —$CF_3$, —$OCF_3$, ethyl, cyclopropyl, oxo, hydroxyl, fluoro, chloro, bromo, cyano, acetyl, amino, methylamino, dimethylamino, acetylamino, carbamate, —$CONH_2$, nitro, —COOH and —$CH_2OH$.

In one embodiment of the invention the compound of formula (I) is a compound of formula (Ie):

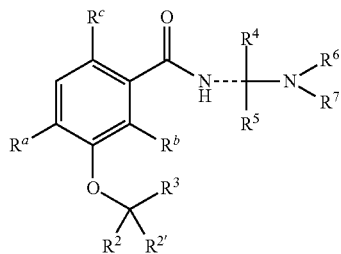

(Ie)

wherein:

$R^b$ and $R^c$ are independently fluoro or chloro, or one of $R^b$ and $R^c$ is hydrogen while the other is fluoro or chloro; or a salt thereof.

In one embodiment of the invention the compound of formula (I) is a compound of formula (If):

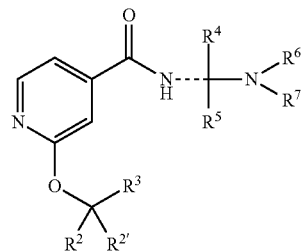

(If)

or a salt thereof.

In one embodiment of the invention the compound of formula (I) is a compound of formula (Ig):

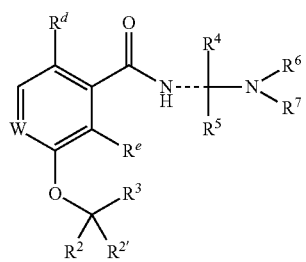

(Ig)

wherein:

$R^d$ and $R^e$ are independently fluoro or chloro, or one of $R^d$ and $R^e$ is hydrogen while the other is fluoro or chloro; and $R^3$ is a radical selected from:

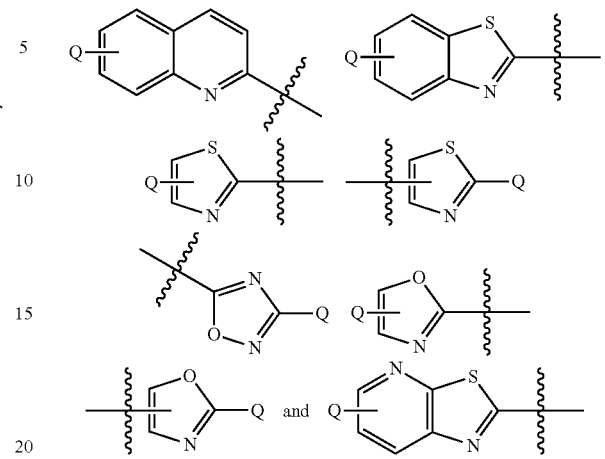

in which any vacant ring position is optionally substituted; or a salt thereof.

In one embodiment of the invention $R^2$ is hydrogen, methyl, or fluoro, and $R^{2'}$ is $(C_1-C_6)$alkyl, $(C_2-C_6)$alkenyl, $(C_2-C_6)$alkynyl, $(C_3-C_8)$cycloalkyl, aryl, or 5-6 membered heterocyclyl, wherein each alkyl, alkenyl, alkynyl, cycloalkyl, aryl, or heterocyclyl may be optionally substituted with one or more $R^b$.

In one embodiment of the invention $R^a$ and $R^2$ taken together are —$CH_2$—, —$CH_2$—$CH_2$—, —O—, —O—$CH_2$—, —$CH_2O$—, —O—$CH_2$—$CH_2$—, or —$CH_2$—$CH_2$—O—.

In one embodiment of the invention $R^{2'}$ taken together with $R^2$ is cyclopropyl, cyclobutyl, azetidine, or =CH—N$(R^c)_2$; wherein the cyclopropyl, cyclobutyl, and azetidine can optionally be substituted with $(C_1-C_6)$alkyl.

In one embodiment of the invention $R^6$ and $R^7$ are each independently hydrogen or methyl, or $R^6$ and $R^7$ together with the nitrogen to which they are attached form a aziridino, azetidino, morpholino, piperazino, pyrrolidino or piperidino ring, which ring is optionally substituted with one or more groups independently selected from $(C_1-C_6)$alkyl.

In one embodiment of the invention:

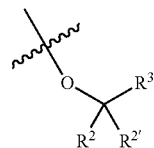

is selected from:

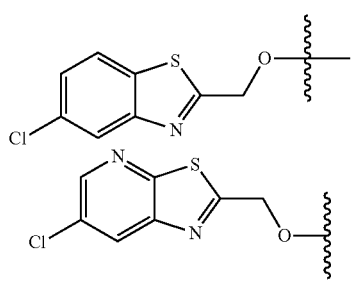

-continued
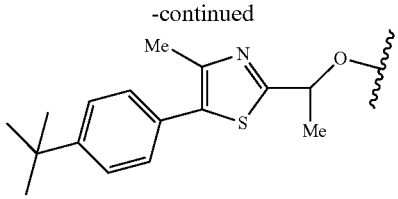
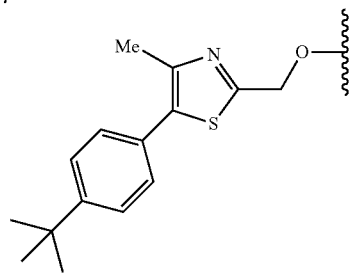
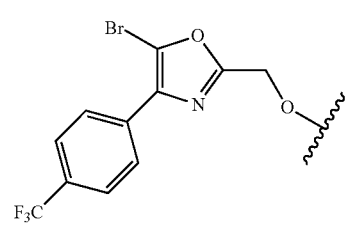
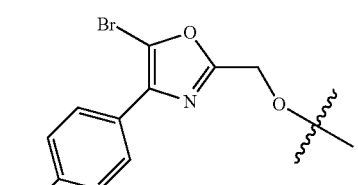
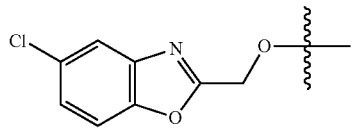
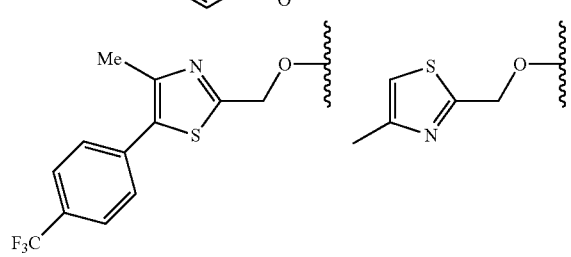
In one embodiment of the invention:
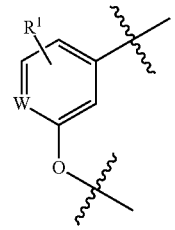
is selected from:
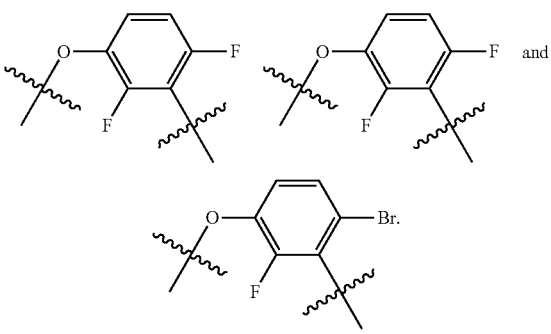
In one embodiment of the invention:
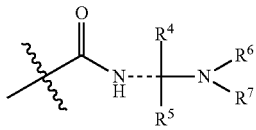
is selected from:
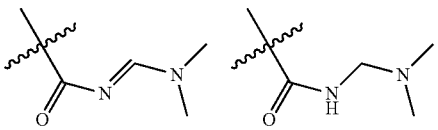
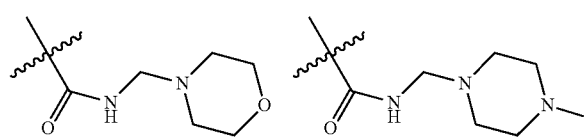
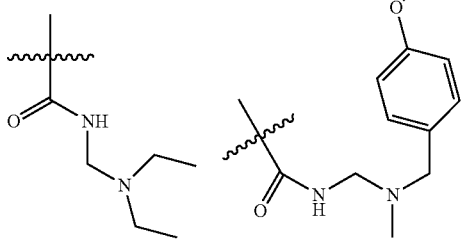

-continued

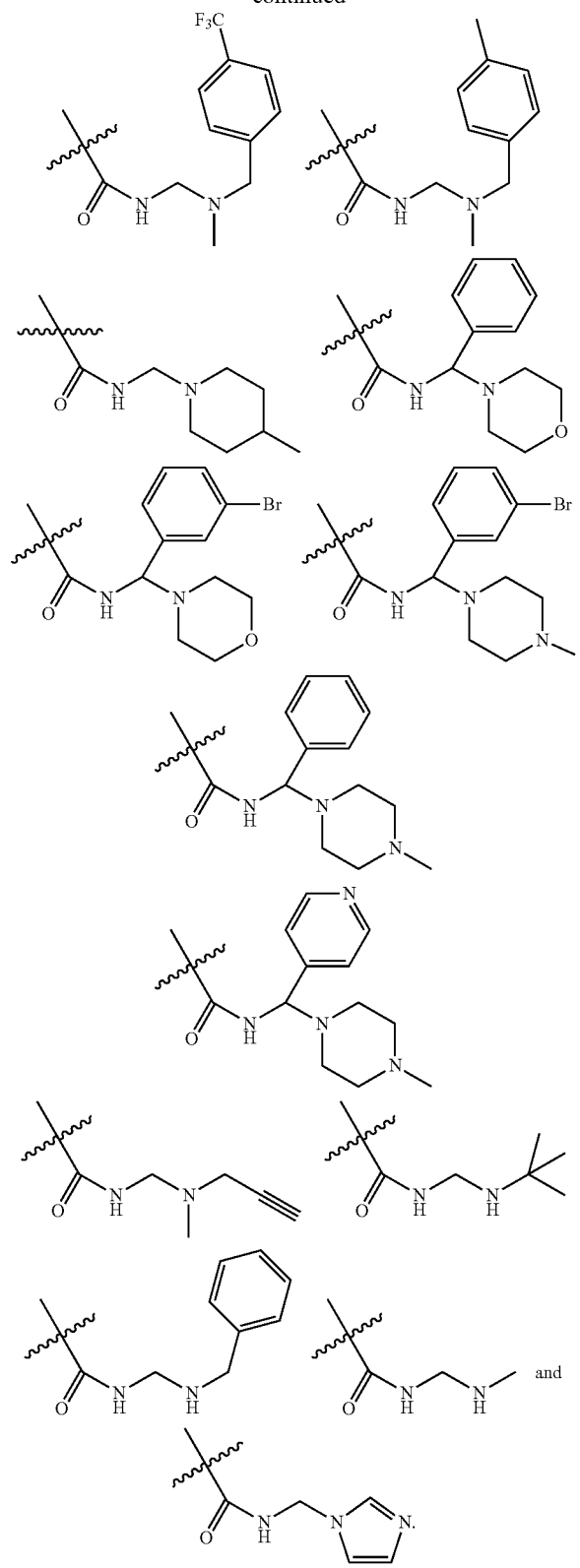

In one embodiment of the invention the compound of formula (I) is selected from:

and salts thereof.

In one embodiment of the invention the compound of formula (I) is selected from:

and salts thereof.

In one embodiment of the invention the compound of formula (I) is selected from:

and salts thereof.

In one embodiment of the invention, when a group is optionally substituted it can be substituted with one or more (e.g. 1, 2, 3, or 4) substituents, each independently selected from $(C_1-C_6)$alkyl, $(C_2-C_6)$alkenyl, $(C_2-C_6)$alkynyl, $(C_1-C_6)$ alkoxy, hydroxyl, hydroxy($C_1$-$C_6$)alkyl, ($C_1$-$C_6$)alkylthio, halo, trifluoromethyl, trifluoromethoxy, nitro, cyano, oxo, phenyl, phenoxy, —COOR$^A$, —COR$^A$, —OCOR$^A$, —SO$_2$R$^A$, —CONR$^A$R$^B$, —SO$_2$NR$^A$R$^B$— NR$^A$R$^B$, —OCONR$^A$R$^B$, —NR$^B$COR$^A$, —NR$^B$COOR$^A$, —NR$^B$—SO$_2$OR$^A$, and —NR$^A$CONR$^A$R$^B$, wherein R$^A$ and R$^B$ are independently hydrogen or a ($C_1$-$C_6$)alkyl group or, in the case where R$^A$ and R$^B$ are linked to the same N atom, R$^A$ and R$^B$ taken together with that nitrogen may form a aziridino, azetidino, morpholino, piperazino, pyrrolidino or piperidino ring; and further wherein any phenyl or phenoxy is optionally substituted with one or more groups independently selected from ($C_1$-$C_6$)alkyl, ($C_2$-$C_6$)alkenyl, ($C_2$-$C_6$)alkynyl, ($C_1$-$C_6$)alkoxy, hydroxyl, hydroxy($C_1$-$C_6$)alkyl, ($C_1$-$C_6$)alkylthio, halo, trifluoromethyl, trifluoromethoxy, nitro, cyano, phenyl, phenoxy, —COOR$^A$, —COR$^A$, —OCOR$^A$, —SO$_2$R$^A$, —CONR$^A$R$^B$, —SO$_2$NR$^A$R$^B$—, —NR$^A$R$^B$, —OCONR$^A$R$^B$, —NR$^B$COR$^A$, —NR$^B$COOR$^A$, —NR$^B$—SO$_2$OR$^A$, and —NR$^A$CONR$^A$R$^B$. It is to be understood that an oxo substituent may only be present when the valency of the substituted group allows.

In one embodiment of the invention, when a group is optionally substituted it can be substituted with one or more (e.g. 1, 2, 3, or 4) substituents, each independently selected from ($C_1$-$C_6$)alkyl, ($C_2$-$C_6$)alkenyl, ($C_2$-$C_6$)alkynyl, ($C_1$-$C_6$) alkoxy, hydroxyl, halo, trifluoromethyl, trifluoromethoxy, nitro, cyano, —COOR$^A$, —COR$^A$, —OCOR$^A$, —CONR$^A$R$^B$, —NR$^A$R$^B$, and —NR$^B$COR$^A$, wherein R$^A$ and R$^B$ are independently hydrogen or a ($C_1$-$C_6$)alkyl group or, in the case where R$^A$ and R$^B$ are linked to the same N atom, R$^A$ and R$^B$ taken together with that nitrogen may form a aziridino, azetidino, morpholino, piperazino, pyrrolidino or piperidino ring.

Specific examples of compounds with which the invention is concerned include those of the Examples herein.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, stereoisomeric, or polymorphic form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

Specific values listed below for radicals, substituents, and ranges, are for illustration only; they do not exclude other defined values or other values within defined ranges for the radicals and substituents.

Specifically, ($C_1$-$C_6$)alkyl can be methyl, ethyl, propyl, isopropyl, butyl, iso-butyl, sec-butyl, pentyl, 3-pentyl, or hexyl; ($C_3$-$C_6$)cycloalkyl can be cyclopropyl, cyclobutyl, cyclopentyl, or cyclohexyl; ($C_1$-$C_6$)alkoxy can be methoxy, ethoxy, propoxy, isopropoxy, butoxy, iso-butoxy, sec-butoxy, pentoxy, 3-pentoxy, or hexyloxy; ($C_1$-$C_6$)alkoxycarbonyl can be methoxycarbonyl, ethoxycarbonyl, propoxycarbonyl, isopropoxycarbonyl, butoxycarbonyl, pentoxycarbonyl, or hexyloxycarbonyl; aryl can be phenyl, indenyl, or naphthoyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, benzimidazole, isoquinolyl (or its N-oxide) or quinolyl (or its N-oxide).

In one embodiment the invention provides a compound selected from compounds of formula I and salts thereof having a minimal inhibitory concentration against MSSA of less than about 8 µg/ml (see Test C below).

In one embodiment the invention provides a compound selected from compounds of formula I and salts thereof having a minimal inhibitory concentration against MSSA of less than about 4 µg/ml.

In one embodiment the invention provides a compound selected from compounds of formula I and salts thereof having a minimal inhibitory concentration against MSSA of less than about 2 µg/ml.

In one embodiment the invention provides a compound selected from compounds of formula I and salts thereof having a minimal inhibitory concentration against MSSA of less than about 1 µg/ml.

In one embodiment the invention provides a compound selected from compounds of formula I and salts thereof having a minimal inhibitory concentration against MSSA of less than about 0.5 µg/ml.

Generally, compounds of I as well as synthetic intermediates that can be used for preparing compounds of formula I, can be prepared as illustrated in the following Schemes. It is understood that variable groups shown in the Schemes below (e.g. $R^1$, $R^2$, and $R^3$) can represent the final corresponding groups present in a compound of formula I or that these groups can represent groups that can be converted to the final corresponding groups present in a compound of formula I at a convenient point in a synthetic sequence. For example, in the Schemes below, the variable groups can contain one or more protecting groups that can be removed at a convenient point in a synthetic sequence to provide the final corresponding groups in the compound of formula I.

The preparation of the various N-substituted 2-ethylidenebenzamides can be accomplished by reaction of a primary benzamide with the dimethyl acetal of the appropriate N-substituted formamide as outlined in Scheme 1. Heating is generally required. The desired products were formed in yields that ranged from 85-90%.

Scheme 1. General method and specific approach used to prepare Examples 1 and 2

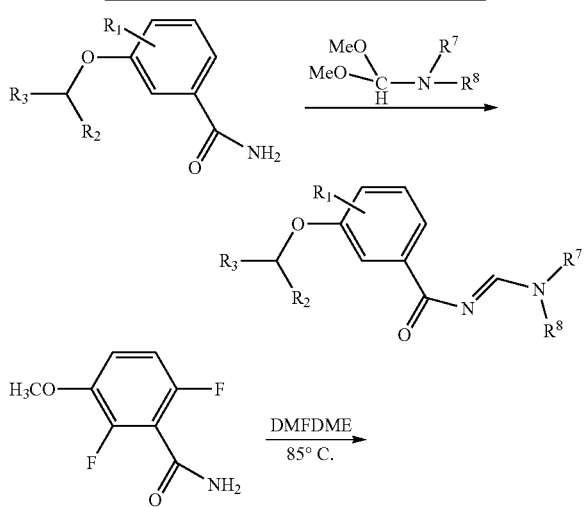

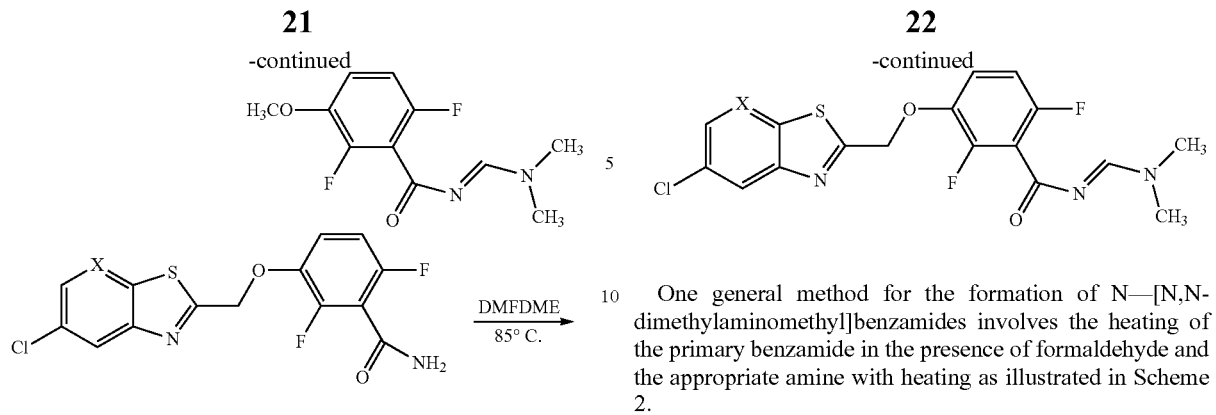

One general method for the formation of N—[N,N-dimethylaminomethyl]benzamides involves the heating of the primary benzamide in the presence of formaldehyde and the appropriate amine with heating as illustrated in Scheme 2.

Scheme 2. General method and approach used to prepare Examples 3, 4, 5 and 6

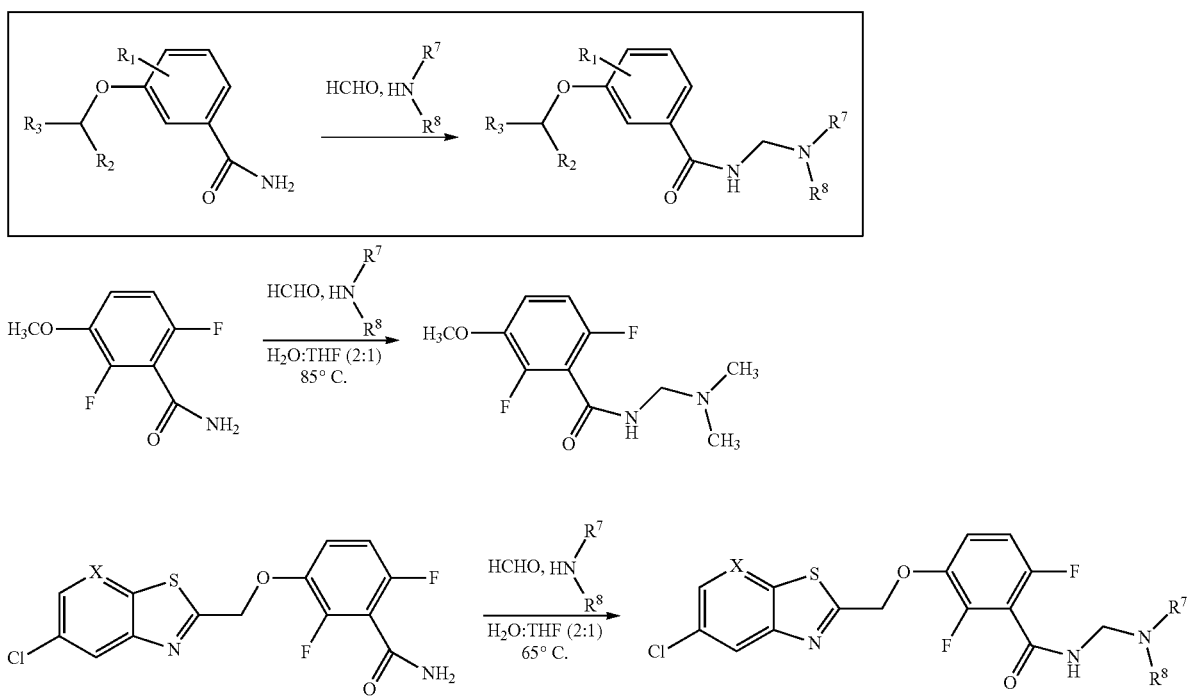

An alternative method for the preparation of N—[N,N-dimethylaminomethyl]benzamides is outlined in Scheme 3. The N-substituted 2-ethylidenebenzamides that can be formed as outlined in Scheme 1 can be reduced to dihydro derivatives. This was found to work in very high yield for the preparation of Example 5.

Scheme 3. An alternative general method and specific methods that have been used to prepare the N-[N,N-dimethylaminomethyl]benzamides Examples 5 and 6.

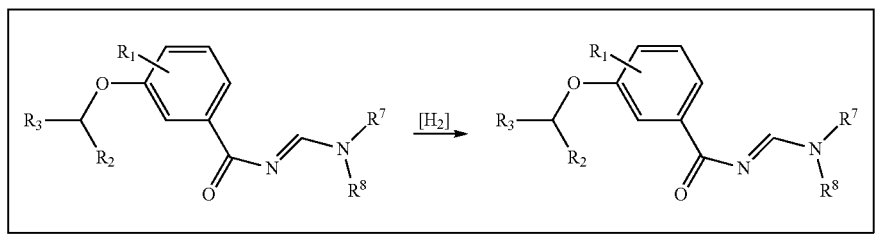

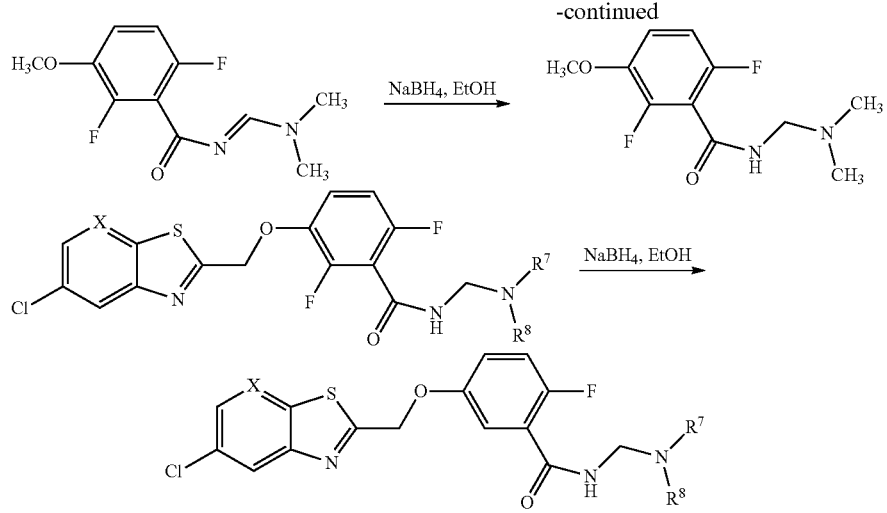

By binding to FtsZ, the compounds of the present invention inhibit the ability of the protein to hydrolyze GTP. This inhibition of FtsZ GTPase activity, in turn, inhibits the ability of the protein to polymerize into Z-rings, as Z-ring formation requires GTP hydrolysis as an energy source for driving the reaction. Since the Z-ring serves as the scaffold for recruitment of all other proteins that comprise the divisome complex, inhibition of Z-ring formation by the compounds of the present invention also results in a corresponding inhibition of divisome protein recruitment.

The compounds of the invention are useful to treat bacterial infections including infections by Gram-negative bacterial strains, Gram-positive bacterial strains and multiple drug-resistant bacterial strains In one embodiment compounds of the present invention may be administered as a composition used to treat and/or prevent a bacterial infection wherein the bacterial cell uses polymerized FtsZ protein, or a homolog thereof, to facilitate cytokinesis. To this end, compounds of the present invention may be administered to treat Staph Infections, Tuberculosis, Urinary Tract Infections, Meningitis, Enteric Infections, Wound Infections, Acne, Encephalitis, Skin Ulcers, Bed Sores, Gastric and Duodenal Ulcers, Eczema, Periodontal disease, Gingivitis, Halitosis, Anthrax, Tularemia, Endocarditis, Prostatitis, Osteomyelitis, Lyme Disease, Pneumonia, or the like.

The compositions can, if desired, also contain other active therapeutic agents, such as a narcotic, a non-steroid anti-inflammatory drug (NSAID), an analgesic, an anesthetic, a sedative, a local anesthetic, a neuromuscular blocker, an anti-cancer, other antimicrobial (for example, an aminoglycoside, an antifungal, an antiparasitic, an antiviral, a carbapenem, a cephalosporin, a fluororquinolone, a macrolide, a penicillin, a sulfonamide, a tetracycline, another antimicrobial), an anti-psoriatic, a corticosteriod, an anabolic steroid, a diabetes-related agent, a mineral, a nutritional, a thyroid agent, a vitamin, a calcium-related hormone, an antidiarrheal, an anti-tussive, an anti-emetic, an anti-ulcer, a laxative, an anticoagulant, an erythropieitin (for example, epoetin alpha), a filgrastim (for example, G-CSF, Neupogen), a sargramostim (GM-CSF, Leukine), an immunization, an immunoglobulin, an immunosuppressive (for example, basiliximab, cyclosporine, daclizumab), a growth hormone, a hormone replacement drug, an estrogen receptor modulator, a mydriatic, a cycloplegic, an alkylating agent, an anti-metabolite, a mitotic inhibitor, a radiopharmaceutical, an anti-depressant, an anti-manic agent, an anti-psychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog thereof, dornase alpha (Pulmozyme), a cytokine, or any combination thereof.

The term "prodrug" as used herein refers to any compound that when administered to a biological system (e.g. a mammal such as a human) generates the drug substance, i.e. active ingredient, as a result of spontaneous chemical reaction(s), enzyme catalyzed chemical reaction(s), photolysis, and/or metabolic chemical reaction(s) or by some other process. A prodrug is thus a modified (e.g. covalently modified) analog or latent form of a therapeutically-active compound. A prodrug may also be an active metabolite or therapeutically-active compound itself. The invention also provides prodrugs of compounds of formula (I).

By way of example a prodrug may generate the active inhibitory compound during metabolism, systemically, inside a cell, by hydrolysis, enzymatic cleavage, or by some other process (Bundgaard, Hans, "Design and Application of Prodrugs" in *A Textbook of Drug Design and Development* (1991), P. Krogsgaard-Larsen and H. Bundgaard, Eds. Harwood Academic Publishers, pp. 113-191; Tranoyl-Opalinski, I., Fernandes, A., Thomas, M., Gesson, J.-P., and Papot, S., Anti-Cancer Agents in Med. Chem., 8 (2008) 618-637). Enzymes which are capable of an enzymatic activation mechanism with the prodrug compounds of the invention include, but are not limited to nitroreductase, proteases (e.g. serine proteases such as prostate specific antigen (PSA), amidases, esterases, microbial enzymes, phospholipases, cholinesterases, and phosphases).

Processes for preparing compounds of formula I are provided as further embodiments of the invention.

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartrate, succinate, fumarate, benzoate, ascorbate, α-ketoglutarate, and α-glycerophosphate. Suitable inorganic salts may also be formed, including hydrochloride, sulfate, nitrate, bicarbonate, and carbonate salts. Salts may be obtained using standard procedures well known in the art, for example by reacting a sufficiently basic compound such as an amine with a suitable acid affording the corresponding anion. Alkali metal (for example, sodium, potassium or lithium) or alkaline earth metal (for example calcium) salts of carboxylic acids can also be made.

Pharmaceutically suitable counterions include pharmaceutically suitable cations and pharmaceutically suitable anions that are well known in the art. Examples of pharmaceutically suitable anions include, but are not limited to those described above (e.g. physiologically acceptable anions) including $Cl^-$, $Br^-$, $I^-$, $CH_3SO_3^-$, $H_2PO_4^-$, $CF_3SO_3^-$, $p\text{-}CH_3C_6H_4SO_3^-$, citrate, tartrate, phosphate, malate, fumarate, formate, or acetate.

It will be appreciated by those skilled in the art that a compound of the invention comprising a counterion can be converted to a compound of the invention comprising a different counterion. Such a conversion can be accomplished using a variety of well known techniques and materials including but not limited to ion exchange resins, ion exchange chromatography and selective crystallization.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes. For oral administration the compounds can be formulated as a solid dosage form with or without an enteric coating.

Thus, the present compounds may be systemically administered, e.g., orally, in combination with a pharmaceutically acceptable vehicle such as an inert diluent, excipient or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 90% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations, particles, and devices.

The active compound may also be administered intravenously or intramuscularly by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina, nanoparticles, and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.1 to about 500 mg/kg, e.g., from about 0.5 to about 400 mg/kg of body weight per day, such as 1 to about 250 mg per kilogram body weight of the recipient per day.

The compound is conveniently formulated in unit dosage form; for example, containing 0.5 to 500 mg, 1 to 400 mg, or 0.5 to 100 mg of active ingredient per unit dosage form.

In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The antibacterial activity of a compound of the invention can be determined using a method like Test A described below.

Test A. Antibacterial Assay.

Antibacterial activity can be determined as per Clinical and Laboratory Standards Institute (CLSI) guidelines using a broth microdilution assay in which log-phase bacteria are grown at 37° C. in appropriate medium containing two-fold serial dilutions of a compound to yield final concentrations ranging from 256 to 0.06 μg/mL. For determination of minimal inhibitory concentration (MIC) values, bacterial growth is monitored after 24 to 48 hours by measuring optical density at 600 nm. MIC values reflect the minimal compound concentrations at which bacterial growth is completely inhibited. Data for representative compounds of the invention are shown in Table 1.

TABLE 1

Minimal Inhibitory Concentrations against MSSA for representative compounds of the Invention

| Example | Structure | MIC (μg/ml) |
|---|---|---|
| 1 | [structure] | >64 |
| 2 | [structure] | >64 |
| 3 | [structure] | <0.125 |
| 4 | [structure] | 0.125 |

TABLE 1-continued

Minimal Inhibitory Concentrations against MSSA for representative compounds of the Invention

| Example | Structure | MIC (µg/ml) |
|---------|-----------|-------------|
| 5 | (6-chlorothiazolo[5,4-b]pyridin-2-yl)methoxy-2,6-difluoro-N-((dimethylamino)methylene)benzamide | 0.25 |
| 6 | (6-chlorothiazolo[5,4-b]pyridin-2-yl)methoxy-2,6-difluoro-N-((dimethylamino)methyl)benzamide | 0.25 |
| 7 | (6-chlorothiazolo[5,4-b]pyridin-2-yl)methoxy-2,6-difluoro-N-(morpholinomethyl)benzamide | 0.5 |
| 8 | (6-chlorothiazolo[5,4-b]pyridin-2-yl)methoxy-2,6-difluoro-N-((4-methylpiperazin-1-yl)methyl)benzamide | 2.0 |
| 9 | (5-chlorobenzo[d]thiazol-2-yl)methoxy-2,6-difluoro-N-((diethylamino)methyl)benzamide | 0.125 |
| 10 | (5-chlorobenzo[d]thiazol-2-yl)methoxy-2,6-difluoro-N-(((4-methoxybenzyl)(methyl)amino)methyl)benzamide | 0.25 |

TABLE 1-continued

Minimal Inhibitory Concentrations against MSSA for representative compounds of the Invention

| Example | Structure | MIC (μg/ml) |
|---------|-----------|-------------|
| 11 | 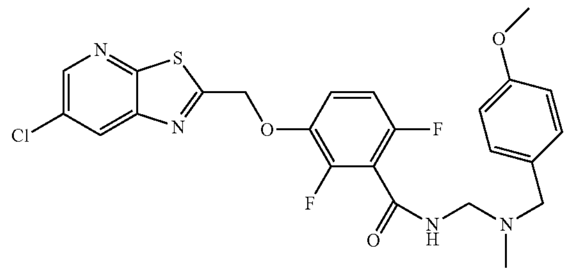 [SMILES: COc1ccc(CN(C)CNC(=O)c2c(F)ccc(OCc3nc4cc(Cl)cnc4s3)c2F)cc1] | 1.0 |
| 12 | 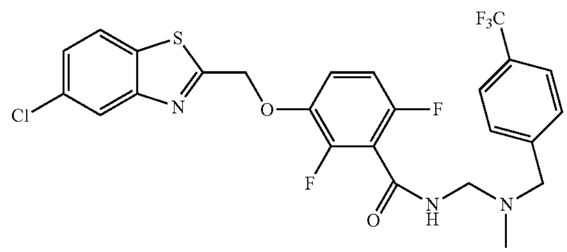 [SMILES: CN(CNC(=O)c1c(F)ccc(OCc2nc3cc(Cl)ccc3s2)c1F)Cc1ccc(C(F)(F)F)cc1] | 0.5 |
| 13 | 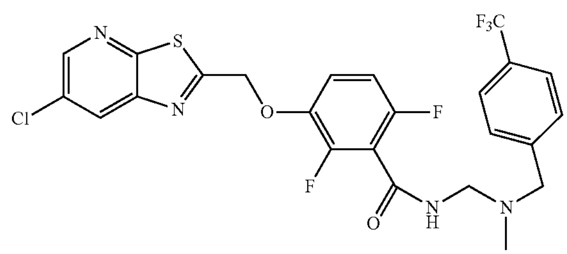 [SMILES: CN(CNC(=O)c1c(F)ccc(OCc2nc3cc(Cl)cnc3s2)c1F)Cc1ccc(C(F)(F)F)cc1] | 1.0 |
| 14 | 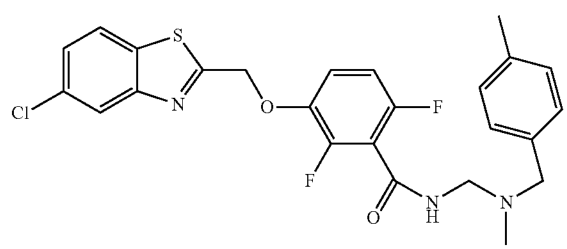 | 0.25 |
| 15 | 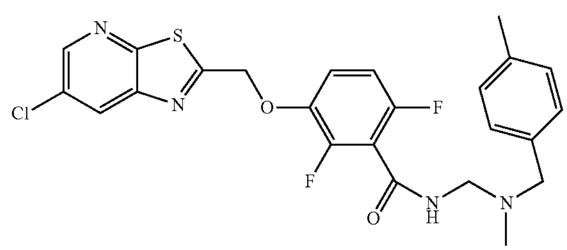 | 0.5 |
| 16 | 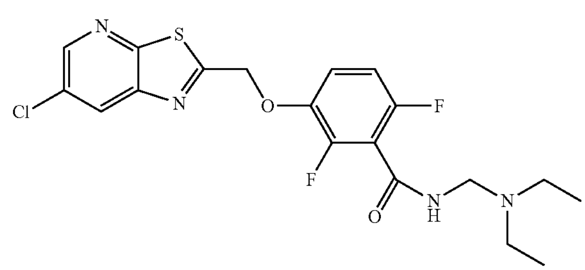 [SMILES: CCN(CC)CNC(=O)c1c(F)ccc(OCc2nc3cc(Cl)cnc3s2)c1F] | 0.5 |

TABLE 1-continued

Minimal Inhibitory Concentrations against MSSA for representative compounds of the Invention

| Example | Structure | MIC (µg/ml) |
|---|---|---|
| 17 | 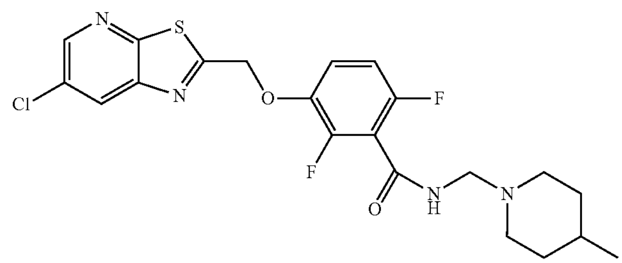 [SMILES: CC1CCN(CNC(=O)c2c(F)ccc(OCc3nc4cc(Cl)cnc4s3)c2F)CC1] | 0.5 |
| 18 | 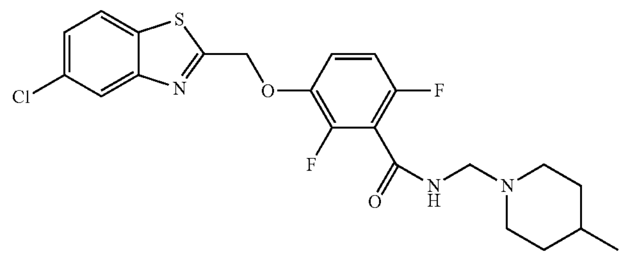 [SMILES: CC1CCN(CNC(=O)c2c(F)ccc(OCc3nc4cc(Cl)ccc4s3)c2F)CC1] | 0.25 |
| 19 | 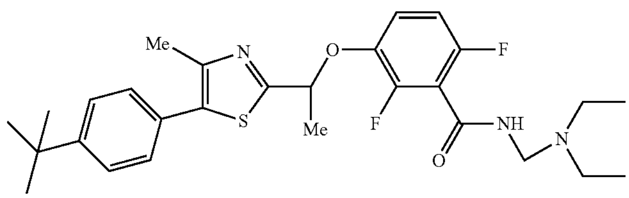 [SMILES: CCN(CC)CNC(=O)c1c(F)ccc(OC(C)c2nc(C)c(-c3ccc(C(C)(C)C)cc3)s2)c1F] | 1.0 |
| 20 | 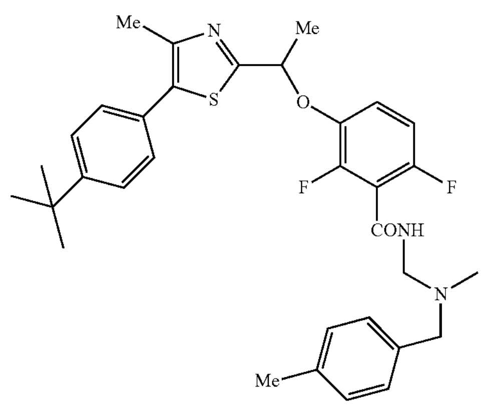 | 1.0 |
| 21 | 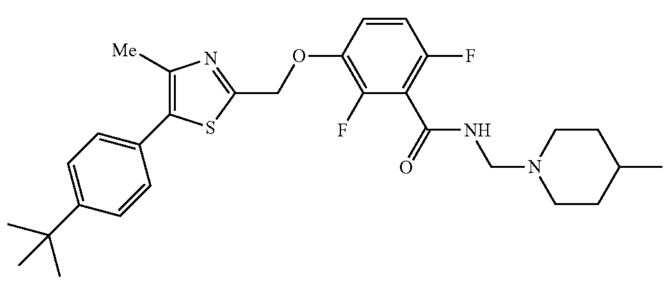 [SMILES: Cc1nc(COc2ccc(F)c(C(=O)NCN3CCC(C)CC3)c2F)sc1-c1ccc(C(C)(C)C)cc1] | 0.5 |

TABLE 1-continued
Minimal Inhibitory Concentrations against MSSA for representative compounds of the Invention
| Example | Structure | MIC (µg/ml) |
|---|---|---|
| 22 | 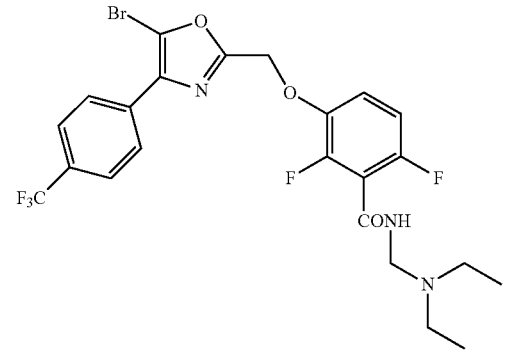 | 0.125 |
| 23 | 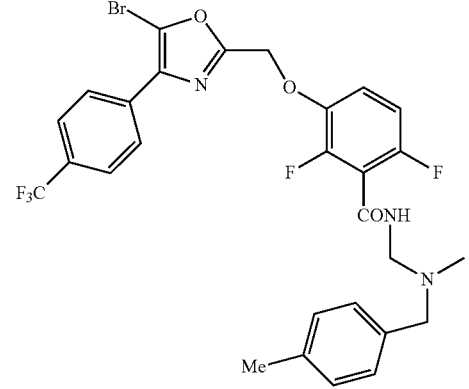 | 0.25 |
| 24 | 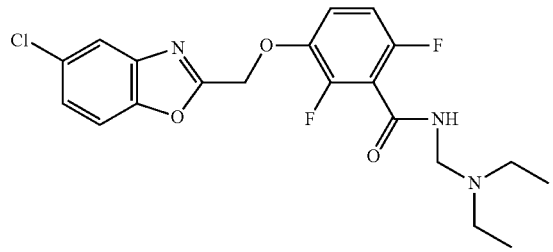 [SMILES: CCN(CC)CNC(=O)c1c(F)ccc(OCc2nc3cc(Cl)ccc3o2)c1F] | 8.0 |
| 25 | 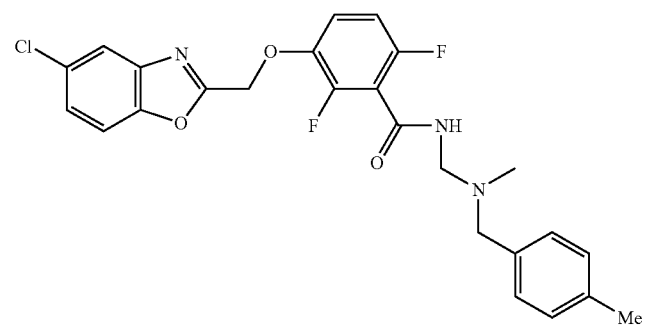 [SMILES: Cc1ccc(CN(C)CNC(=O)c2c(F)ccc(OCc3nc4cc(Cl)ccc4o3)c2F)cc1] | 16 |

TABLE 1-continued
Minimal Inhibitory Concentrations against MSSA for representative compounds of the Invention
| Example | Structure | MIC (µg/ml) |
|---|---|---|
| 26 | 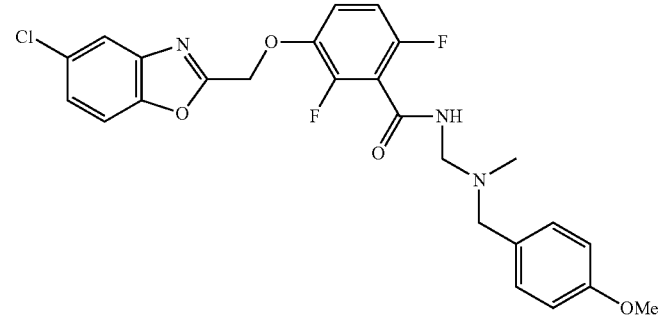 [SMILES: COc1ccc(CN(C)CNC(=O)c2c(F)ccc(OCc3nc4cc(Cl)ccc4o3)c2F)cc1] | 16 |
| 27 | 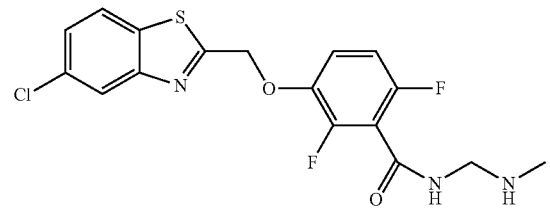 [SMILES: CNCNC(=O)c1c(F)ccc(OCc2nc3cc(Cl)ccc3s2)c1F] | 0.125 |
| 28 | 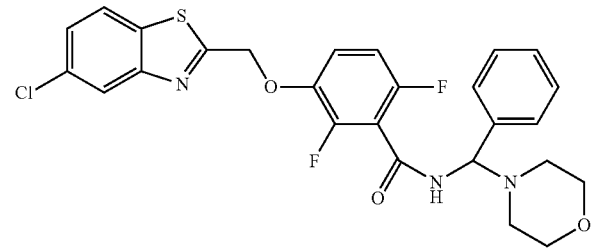 [SMILES: O=C(NC(c1ccccc1)N1CCOCC1)c1c(F)ccc(OCc2nc3cc(Cl)ccc3s2)c1F] | 0.25 |
| 29 | 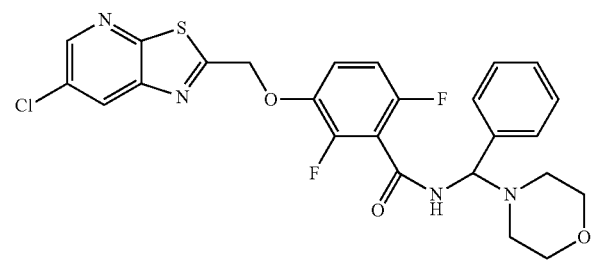 [SMILES: O=C(NC(c1ccccc1)N1CCOCC1)c1c(F)ccc(OCc2nc3cc(Cl)cnc3s2)c1F] | 1.0 |
| 30 | 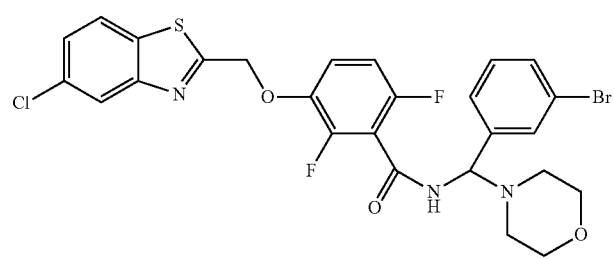 [SMILES: O=C(NC(c1cccc(Br)c1)N1CCOCC1)c1c(F)ccc(OCc2nc3cc(Cl)ccc3s2)c1F] | 0.5 |

TABLE 1-continued
Minimal Inhibitory Concentrations against MSSA for representative compounds of the Invention
| Example | Structure | MIC (μg/ml) |
|---|---|---|
| 31 | 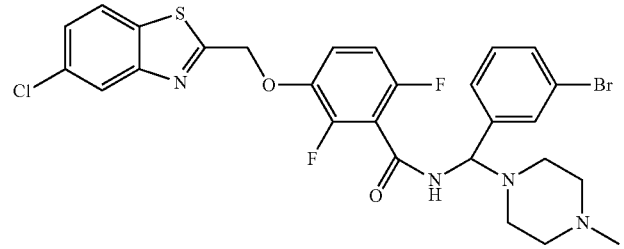 | 0.5 |
| 32 | 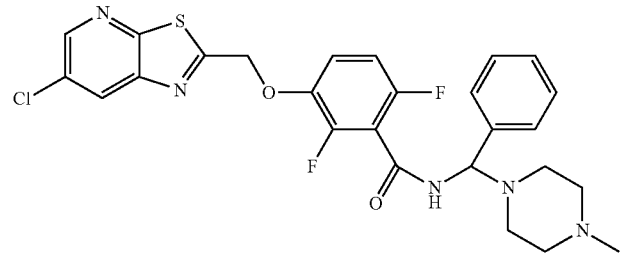 [SMILES: CN1CCN(C(NC(=O)c2c(F)ccc(OCc3nc4cc(Cl)cnc4s3)c2F)c2ccccc2)CC1] | 0.5 |
| 33 | 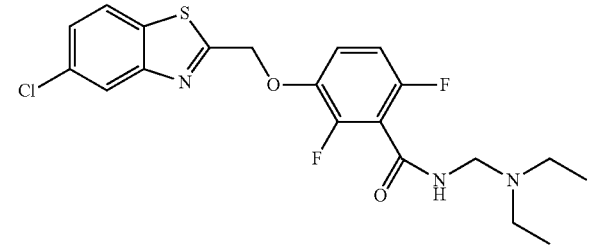 | 2.0 |
| 34 | 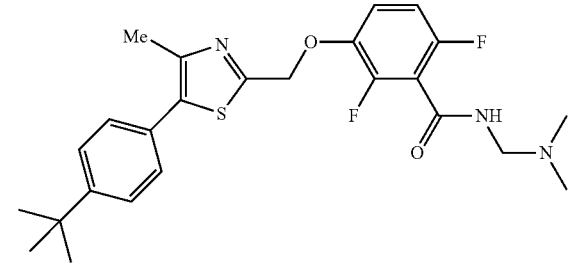 [SMILES: Cc1nc(COc2ccc(F)c(C(=O)NCN(C)C)c2F)sc1-c1ccc(C(C)(C)C)cc1] | 0.125 |
| 35 | 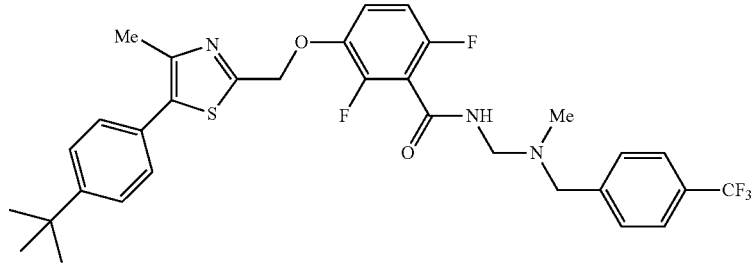 [SMILES: Cc1nc(COc2ccc(F)c(C(=O)NCN(C)Cc3ccc(C(F)(F)F)cc3)c2F)sc1-c1ccc(C(C)(C)C)cc1] | >64 |

TABLE 1-continued

Minimal Inhibitory Concentrations against MSSA for representative compounds of the Invention

| Example | Structure | MIC (µg/ml) |
|---|---|---|
| 36 | 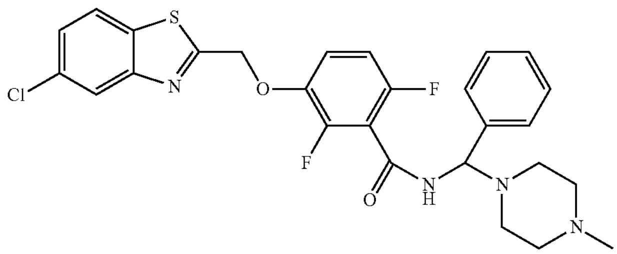 [SMILES: CN1CCN(C(NC(=O)c2c(F)ccc(OCc3nc4cc(Cl)ccc4s3)c2F)c2ccccc2)CC1] | 0.25 |
| 37 | 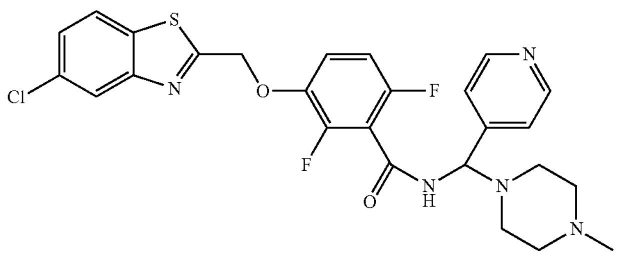 [SMILES: CN1CCN(C(NC(=O)c2c(F)ccc(OCc3nc4cc(Cl)ccc4s3)c2F)c2ccncc2)CC1] | 0.5 |
| 38 | 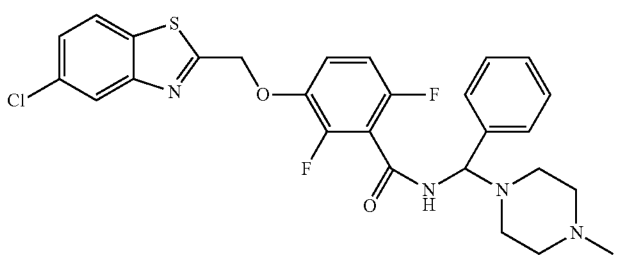 [SMILES: CN1CCN(C(NC(=O)c2c(F)ccc(OCc3nc4cc(Cl)ccc4s3)c2F)c2ccccc2)CC1] | 8.0 |
| 39 | 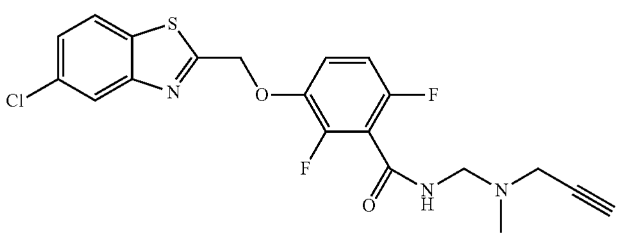 [SMILES: C#CCN(C)CNC(=O)c1c(F)ccc(OCc2nc3cc(Cl)ccc3s2)c1F] | 0.25 |
| 40 | 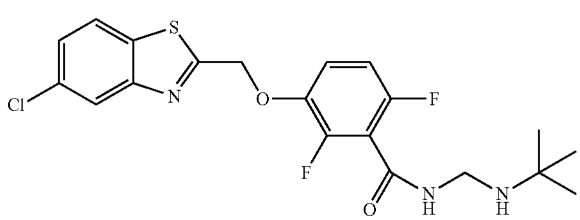 [SMILES: CC(C)(C)NCNC(=O)c1c(F)ccc(OCc2nc3cc(Cl)ccc3s2)c1F] | 0.5 |
| 41 | 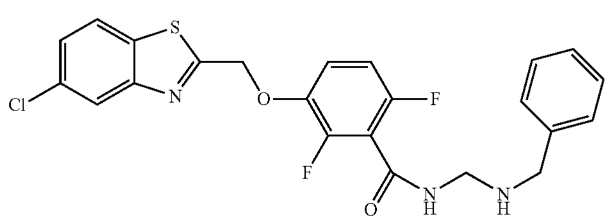 [SMILES: O=C(NCNCc1ccccc1)c1c(F)ccc(OCc2nc3cc(Cl)ccc3s2)c1F] | 0.5 |

TABLE 1-continued

Minimal Inhibitory Concentrations against MSSA for representative compounds of the Invention

| Example | Structure | MIC (μg/ml) |
|---|---|---|
| 42 | 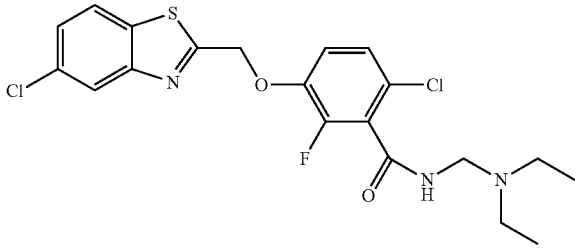 [SMILES: CCN(CC)CNC(=O)c1c(Cl)ccc(OCc2nc3cc(Cl)ccc3s2)c1F] | 2.0 |
| 43 | 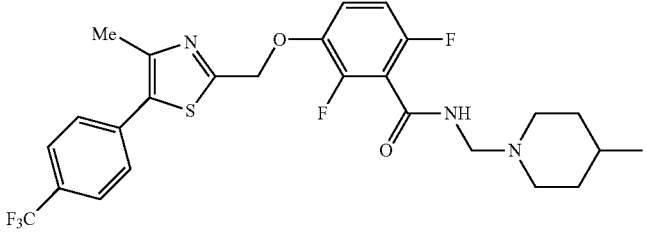 [SMILES: Cc1nc(COc2ccc(F)c(C(=O)NCN3CCC(C)CC3)c2F)sc1-c1ccc(C(F)(F)F)cc1] | 2.0 |
| 44 | 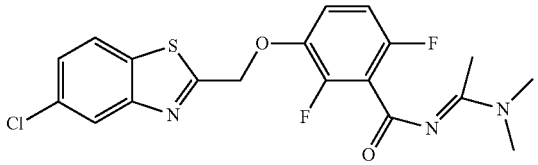 | 2.0 |
| 45 | 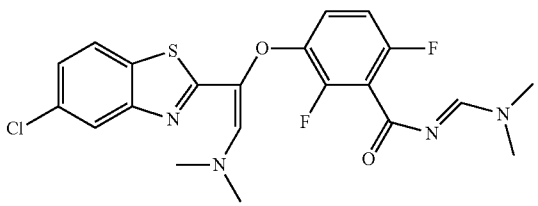 [SMILES: CN(C)/C=N/C(=O)c1c(F)ccc(O/C(=C/N(C)C)c2nc3cc(Cl)ccc3s2)c1F] | 32 |
| 46 | 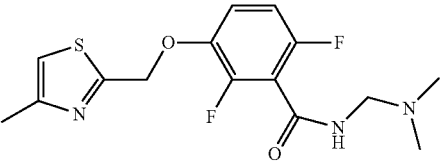 | 8.0 |

The impact of a compound of the invention on the dynamics of bacterial FtsZ polymerization can be determined using a method like Test B described below.

Test B. FtsZ Polymerization Assay.

Compound-induced alteration in the dynamics of FtsZ polymerization can be tested using a turbidity assay with purified FtsZ protein. Upon addition of GTP, FtsZ self-associates to form polymeric structures that scatter light at 340 nm to a greater extent than the monomeric protein. The impact of the compounds of the invention on the polymerization dynamics of FtsZ can be detected by an increase or decrease in the extent of GTP-induced light scattering (as determined by corresponding changes in optical density at 340 nm) relative to that observed in the absence of compound. Quantitation of the overall extent of light scattering as a function of compound concentration provides an indication of the potency of that compound at altering the dynamics of FtsZ polymerization.

The impact of a compound of the invention on FtsZ Z-ring formation in bacteria can be determined using a method like Test C described below.

Test C. FtsZ Z-Ring Assay.

The impact of a compound on FtsZ Z-ring formation can be determined using a strain of $Bacillus\ subtilis$ (FG347) that expresses a green fluorescent protein (GFP)-ZapA fusion protein upon induction with xylose. ZapA is known to associate with FtsZ Z-rings in $B.\ subtilis$ and, thus, serves as a marker for Z-ring formation. In this assay, log-phase FG347 bacteria are treated with differing concentrations of compound for time periods ranging from 1 to 6 hours. At each time point, aliquots are taken from each culture and then viewed with a fluorescence microscope. In the absence of compound, the bacteria exhibit green fluorescent foci (Z-rings) localized at mid-cell. By contrast, bacteria treated with a compound that disrupts Z-ring formation do not exhibit the green fluorescent Z-rings at mid-cell and are typically associated with an elongated, filamentous phenotype.

Summary of Results from Tests B and C—

Examples 4 and 6-8 were evaluated for their impact on the polymerization of *Staphylococcus aureus* FtsZ. At a concentration of 20 μg/mL, all the tested compounds were found to stimulate *S. aureus* FtsZ polymerization by ≥2.5-fold. In addition, Example 5 and 7 were also examined for their impact on FtsZ Z-ring formation in *Bacillus subtilis* FG347 bacteria. At a concentration of 3 μg/mL, both compounds were found to inhibit FtsZ Z-ring formation, while also inducing an elongated, filamentous morphology. These collective results highlight the compounds of the invention as FtsZ-targeting antibacterial agents.

Test D. Formulation of Test Compounds.

Efforts to formulate 5-chloro-2-(2,4-difluoro-3-aminocarbonylphenoxy)methylbenzthiazole (the benzamide related to Examples 3 and 4) and 5-chloro-2-(2,4-difluoro-3-aminocarbonylphenoxy)methylpyridylthiazole related to Examples 5, 6, 7 and 8 proved very problematic. The literature vehicle reported for formulation of 5-chloro-2-(2,4-difluoro-3-aminocarbonylphenoxy)methylpyridylthiazole for i.v. administration consists of 20% DMA, 40% polyethylene glycol and 40% saline. Attempts to inject this vehicle alone i.v. proved lethal at volumes greater than 150 μl. Mice that were treated 15 minutes later with a second injection consisting of 150 μl of this vehicle died. In addition, concentrations of 5-chloro-2-(2,4-difluoro-3-aminocarbonylphenoxy)methylpyridylthiazole at or above 2.2 mg/ml in this vehicle were not completely dissolved and existed as a suspension (in a 28 g mouse this would be 15.7 mg/kg). A number of other formulations with 5-chloro-2-(2,4-difluoro-3-aminocarbonylphenoxy)methyl benzothiazole were tried, such as 20% DMA, 40% proplyeneglycol in 8% Cremophor-EL. Mice treated with this formulation died within a few minutes from what appears to be an embolitic effect caused by drug precipitation. Because of the limited solubility and the absence of a suitable vehicle, the literature study where it was reported that a 30 mg/kg dose of 5-chloro-2-(2,4-difluoro-3-aminocarbonylphenoxy)methylpyridylthiazole was delivered to mice in a single injection could not be repeated. In mark contrast we found that Examples 4 and 6 could be readily formulated at concentration of 2.0 mg/ml in 10 mM solutions of citrate, methane sulfonate, p-toluene sulphonate, phosphoric acid, and tartaric acid. In some instances the addition of 10-30% propylene glycocol did allow for greater retention of solubility of the test compounds. Example 4 was also found to formulate well at a 2.0 mg/ml concentration in 10 mM malic acid with 20% propylene glycol and with 10 mM p-toluenesulphonate alone. Example 6 did formulate well in 10 mM citrate alone at a concentration of 2.0 mg/ml. Using 10 mM citrate, we found that we could administer 300 μl of this vehicle four times within a 45 minute time period. The ability of mice to tolerate this vehicle did allow for multiple dosing in the assessment of Example 6 in vivo and to actually deliver higher doses of the Example 6 because of the compatibility of a predominately aqueous vehicle.

Test E. In Vivo Efficacy in the Mouse Peritonitis or Mouse Septicemia Model.

Assessment of in vivo efficacy was performed using femal Swiss Webster mice (obtained from Taconic Farms, Germantown, Pa.) employing a murine septicemia model of staphylococcal infection. For bioassays examining efficacy against MSSA, each mouse was inoculated intraperitoneally with 500 μl of an inoculum containing $1.0 \times 10^8$ CFU per ml of *S. aureus*. All of the in vivo efficacy studies include a negative control group of infected mice treated intravenously either with vehicle alone (6 mice) or untreated (6 mice), as well as a positive control groups of infected mice treated with 200 ul of 1.0 of vancomycin administered intravenously (4 mice) and a second control group using 2.0 mg/ml of oxacillin (4 mice). After the mice were infected, groups of six mice are treated by tail vein injection with 300 ul of a solution containing 2.0 mg of Example 6 in 10 mM citrate. Mice received four doses Example 6 administered with a 15 minute interval. Control mice are treated with vancomycin qd, oxacillin b.i.d, or vehicle alone. One of the mice treated with Example 6 died during the course of treatment. Animals are given food and water ad libitum. Survival within each experimental group is monitored over a 24 hout time period. Monitoring of the mice began 4 hours after the start of experiment. All of the effective mice treated with Example 6 survived the infection (5/5, 100% survival). All of the oxacillin-treated (4/4) and vancomycin-treated mice (4/4) survived the infection. All of the vehicle controls died within 12 hours, with 0/6 or 0% survival. Among the infected mice that receive no treatment, only 1/6 survived (16.7% survival). These results clearly demonstrate the in vivo efficacy of Example 6 as an antibiotic.

The invention will now be illustrated by the following non-limiting examples.

EXAMPLES

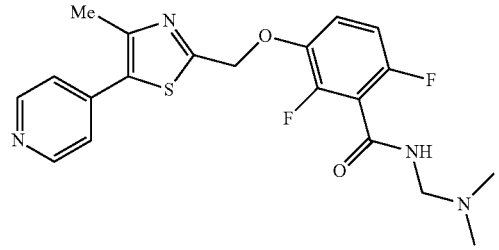 [SMILES: Cc1nc(COc2ccc(F)c(C(=O)NCN(C)C)c2F)sc1-c1ccncc1]

Example 1

In a sealed tube, mixture of benzamide 49C (8 mg, 0.022 mmol), formaldehyde (37%) (0.006 mL, 0.22 mmol), and amine (0.11 mL, 0.22 mmol) in H$_2$O:THF (2:1) was heated at 65° C. for 2 h. The reaction mixture was cooled to room temperature. Extraction with ethyl acetate (×3) afforded a brown solid which was then purified by column chromatography to furnish (5 mg, 56% Yield) of the pure product. $^1$H NMR (CD$_3$OD, 400 MHz) δ: 8.52-8.50 (m, 2H), 7.48-7.47 (m, 2H), 7.28-7.22 (m, 1H), 6.95-6.90 (m, 1H), 5.35 (s, 2H), 4.12 (s, 2H), 2.46 (s, 3H), 2.23 (s, 6H).

The requisite intermediates were prepared as follows a. Preparation of Compound

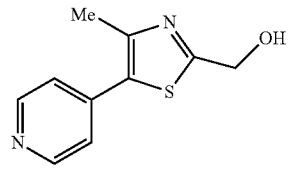 [SMILES: Cc1nc(CO)sc1-c1ccncc1]

A 25-mL round bottom flask equipped with a magnetic stirrer, a condenser and a nitrogen in/outlet adapter was charged with bromo compound 21b (50 mg, 0.24 mmol), 4-pyridylboronic acid (44 mg, 0.36 mmol), water/dioxane (1.5 mL/3 ml), K$_2$CO$_3$ (99 mg, 0.72 mmol). The resulting solution was degassed for 5 minutes, then Pd(OAc)$_2$ (5 mg, 0.024 mmol) and XPhos (23 mg, 0.048 mmol) was added. The reaction mixture was warmed to 100° C. and stirred overnight. After cooled to room temperature, the reaction mixture was diluted with EtOAc (75 mL) and washed with saturated NaHCO$_3$ (25 mL), dried over Na$_2$SO$_4$. The organic layer was concentrated under reduced pressure and purified on ISCO max gradient 2% MeOH/DCM to give (10 mg, 20% Yield) of the title compound. $^1$H NMR (CDCl$_3$, 400 MHz) δ: 8.50-8.49 (m, 2H), 7.46-7.45 (m, 2H), 4.72 (s, 2H), 2.43 (s, 3H).

b. Preparation of Compound

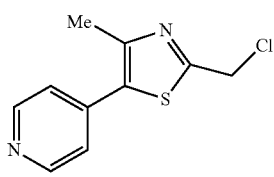 [SMILES: Cc1nc(CCl)sc1-c1ccncc1]

A 25-mL round bottom flask equipped with a magnetic stirrer under nitrogen was charged with alcohol 49a (17 mg, 0.083 mmol), CH$_2$Cl$_2$ (2 mL), and triethylamine (0.03 mL, 0.21 mmol). Methanesulfonyl chloride (0.013 mL, 0.166 mmol) was added via a syringe over 5 minutes. The resulting reaction mixture was stirred at room temperature overnight. The reaction mixture was diluted with CH$_2$Cl$_2$ (30 mL) and washed with saturated NaHCO$_3$ (15 ml), dried over Na$_2$SO$_4$, and concentrated under reduced pressure and purified on ISCO max gradient 30% EtOAc/hexane affording (11 mg, 79% Yield) of the title compound. $^1$H NMR (CD$_3$OD, 400 MHz) δ: 8.66-8.63 (m, 2H), 7.60-7.58 (m, 2H), 4.95 (s, 2H), 2.57 (s, 3H).

c. Preparation of Compound

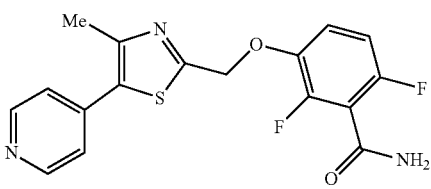 [SMILES: Cc1nc(COc2ccc(F)c(C(N)=O)c2F)sc1-c1ccncc1]

A 25-mL round bottom flask equipped with a magnetic stirrer, a condenser and a nitrogen in/outlet adapter was charged with chloro intermediate 49b (10 mg, 0.044 mmol), DMF (1.5 mL), K$_2$CO$_3$ (9 mg, 0.066 mmol), and phenol (8 mg, 0.044 mmol) The reaction mixture was stirred at RT overnight. The reaction mixture was diluted water (30 mL) and precipitate was filtered off and washed with additional water (3 mL) then dissolved in DCM and concentrated. Purification on ISCO max gradient 2% MeOH/DCM to give (10 mg, 63% Yield) of the title compound. $^1$H NMR (CD$_3$OD, 400 MHz) δ: 8.64-8.62 (m, 2H), 7.60-7.58 (m, 2H), 7.38-7.32 (m, 1H), 7.04-6.99 (m, 1H), 5.46 (s, 2H), 2.56 (s, 3H).

Example 2

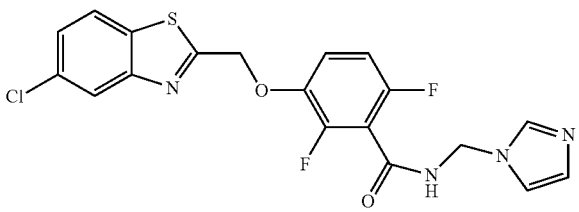 [SMILES: O=C(NCn1ccnc1)c1c(F)ccc(OCc2nc3cc(Cl)ccc3s2)c1F]

A 25-mL round bottom flask equipped with a magnetic stirrer under nitrogen was charged with the chloride 39b (50 mg, 0.12 mmol), CH$_2$Cl$_2$ (5 mL). After cooling to −30° C., imidazole (50 mg) was added. The reaction mixture was warmed to room temperature and stirred for 1 hour. The solvent was removed and the residue was purified by column chromatography to afford the pure product (12 mg, 20% Yield) as off white solid. $^1$H NMR (DMSO, 300 MHz) δ: 9.87 (bs, 1H), 8.20 (d, J=8.4 Hz, 1H), 8.13 (d, J=2.1 Hz, 1H), 7.75 (s, 1H), 7.56-7.43 (m, 2H), 7.20-7.14 (m, 2H), 6.96 (s, 1H), 5.78 (s, 2H), 5.73 (s, 2H).

Example 3

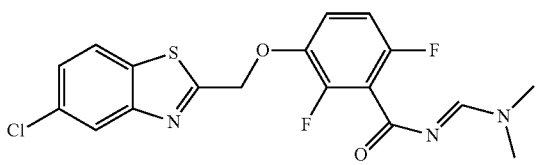 [SMILES: CN(C)/C=N/C(=O)c1c(F)ccc(OCc2nc3cc(Cl)ccc3s2)c1F]

A suspension of the substituted benzamide 3a (355 mg, 1 mmol) in 3.0 mL of dimethylformamide dimethyl acetal was stirred at 90° C. for 1 hour. The excess dimethylformamide dimethyl acetal was removed under reduced pressure and the resulting solid was triturated with diethyl ether to afford the pure product (150 mg, 36% yield). $^1$H NMR (CDCl$_3$, 300 MHz) δ: 8.62 (s, 1H), 8.00 (s, 1H), 7.82 (d, J=6.0 Hz, 1H), 7.39 (m, 1H), 7.07-6.97 (m, 1H), 6.84-6.79 (m, 1H), 5.49 (s, 2H), 3.21 (s, 3H), 3.16 (s, 3H).

The requisite intermediate was prepared as follows a. Preparation of Compound

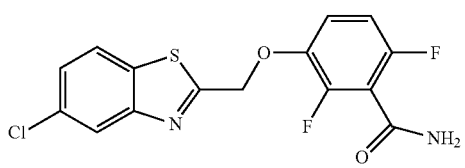

The compound was prepared using procedures similar to those described in *Science* 2008, 321, 1673-1675; and *J. Med. Chem.* 2010, 53, 3927-3936.

Example 4

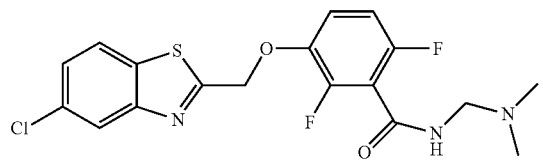

To a solution of above N-[(Dimethylamino)ethylidene] benzamide from example 3 (30 mg, 0.073 mmol) in EtOH (4.0 mL) was added NaBH$_4$ (6 mg, 0.14 mmol). The reaction mixture was stirred for 1 hour at room temperature after which, the excess NaBH$_4$ was destroyed by addition of acetone. The column chromatography of the crude product afforded the pure product as white solid (22 mg, 73% yield). $^1$H NMR (CDCl$_3$, 300 MHz) δ 8.01 (s, 1H), 7.83 (d, J=9.0 Hz, 1H), 7.41 (m, 1H), 7.11 (m, 1H), 6.87 (m, 1H), 6.50 (bs, 1H), 5.50 (s, 2H), 4.28 (d, J=6.0 Hz, 2H), 2.37 (s, 6H).

Example 5

A suspension of substituted benzamide 5a (20 mg, 0.056 mmol) in 0.5 mL of dimethylformamide dimethyl acetal was stirred at 90° C. for 1 hour. The excess dimethylformamide dimethyl acetal was removed under reduced pressure and the resulting solid was triturated with diethyl ether to afford the pure product (10 mg, 43% yield). $^1$H NMR (CDCl$_3$, 300 MHz) δ 8.63 (s, 1H), 8.57 (s, 1H), 8.24 (s, 1H), 7.08 (m, 1H), 6.84 (m, 1H), 5.47 (s, 2H), 3.21 (s, 3H), 3.16 (s, 3H).

The required intermediate was prepared as follows a. Preparation of Compound

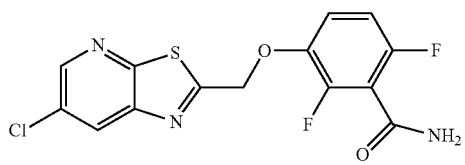 [SMILES: NC(=O)c1c(F)ccc(OCc2nc3cc(Cl)ccc3s2)c1F]

The compound was prepared using procedures similar to those described in *Science* 2008, 321, 1673-1675; and *J. Med. Chem.* 2010, 53, 3927-3936.

Example 6

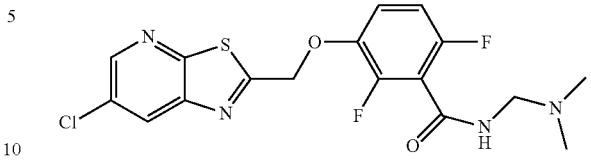

In a sealed tube, mixture of benzamide 5a (200 mg, 0.56 mmol), formaldehyde (37%, 0.3 mL, 3.7 mmol) and dimethylamine (2 M in THF, 1.9 mL, 3.70 mmol) in H$_2$O:THF (8 mL:4 mL) was heated at 65° C. for 2 hours. After cooling to room temperature, the reaction mixture was diluted with ethyl acetate, washed with brine, dried over Na$_2$SO$_4$, and concentrated to afford a brown solid, which was purified by column chromatography to afford the pure product as light brown solid (154 mg, 67% yield). $^1$H NMR (CDCl$_3$, 300 MHz) δ: 8.57 (d, J=2.1 Hz, 1H), 8.24 (d, J=2.1 Hz, 1H), 7.17-7.09 (m, 1H), 6.92-6.86 (m, 1H), 6.20 (bs, 1H), 5.48 (s, 2H), 4.30 (d, J=6.0 Hz, 2H), 2.37 (s, 6H).

Example 7

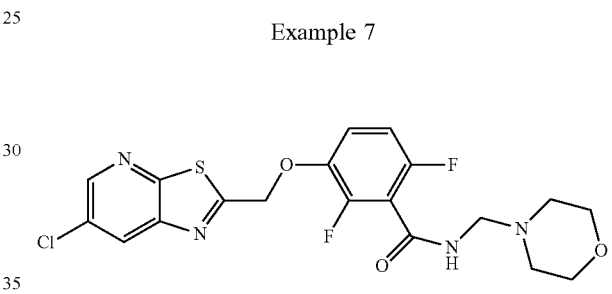

In a sealed tube, mixture of benzamide 5a (100 mg, 0.28 mmol), formaldehyde (37% in water, 0.11 mL) and morpholine (0.12 mL, 1.4 mmol) in H$_2$O:THF (2 mL:1 mL) was heated at 65° C. for 2 hours. After cooling to room temperature, the reaction mixture was diluted with ethyl acetate, washed with brine, dried over Na$_2$SO$_4$, and concentrated to afford a brown solid, which was purified by column chromatography to afford the pure product (60 mg, 47% yield). $^1$H NMR (CDCl$_3$, 300 MHz) δ: 8.58 (d, J=3.0 Hz, 1H), 8.25 (d, J=3.0 Hz, 1H), 7.19-7.11 (m, 1H), 6.92 (m, 1H), 6.29 (bs, 1H), 5.49 (s, 2H), 4.34 (d, J=6.0 Hz, 2H), 3.73 (t, J=6.0 Hz, 4H), 2.66 (t, J=6.0 Hz, 4H).

Example 8

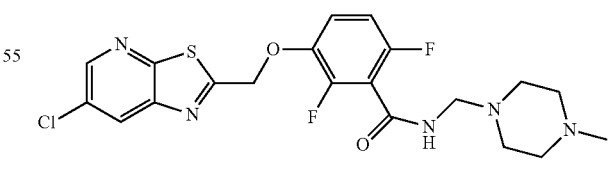

In a sealed tube, mixture of benzamide 5a (1 mmol), formaldehyde (37%) (10 mmol) and amine (10 mmol) in H$_2$O:THF (2:1) was heated at 65° C. for 2 hours. After cooling to room temperature, the reaction mixture was diluted with ethyl acetate, washed with brine, dried over Na$_2$SO$_4$, and concentrated to afford a brown solid, which was purified by column chromatography to afford the pure product (27 mg. 60% yield). $^1$H NMR (CDCl$_3$, 300 MHz) δ: 8.59 (d, J=3.0 Hz, 1H), 8.24 (d, J=3.0 Hz, 1H), 7.16-7.00 (m, 1H), 6.92-6.85 (m, 1H), 6.28 (bs, 1H), 5.49 (s, 2H), 4.37 (d, J=6.0 Hz, 2H), 2.70 (m, 4H), 2.47 (m, 4H), 2.30 (s, 3H).

as off white solid. $^1$H NMR (CDCl$_3$, 300 MHz) δ: 8.00 (d, J=1.8 Hz, 1H), 7.82 (d, J=8.7 Hz, 1H), 7.40 (dd, J=2.1, 8.7 Hz, 1H), 7.23 (d, J=8.7 Hz, 2H), 7.14-7.07 (m, 1H), 6.90-6.83 (m, 1H), 6.85 (d, J=7.8 Hz, 2H), 6.20 (bs, 1H), 5.50 (s, 2H), 4.39 (d, J=6.3 Hz, 2H), 3.79 (s, 3H), 3.60 (s, 2H), 2.33 (s, 3H).

Example 9

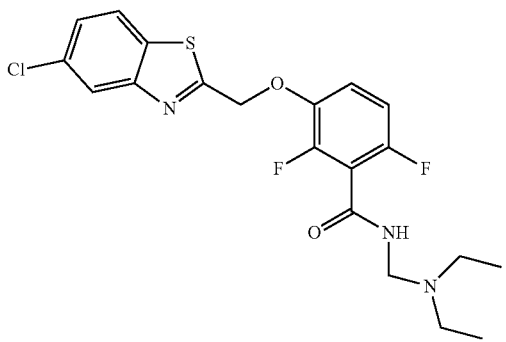 [SMILES: CCN(CC)CNC(=O)c1c(F)ccc(OCc2nc3cc(Cl)ccc3s2)c1F]

In a sealed tube, mixture of benzamide 3a (55 mg, 0.15 mmol), formaldehyde (37%, 0.063 mL, 0.77 mmol) and diethylamine (55 mg, 0.75 mmol) in H$_2$O:THF (1 mL: 0.5 mL) was heated at 65° C. for 2 hours. After cooling to room temperature, the reaction mixture was diluted with ethyl acetate, washed with brine, dried over Na$_2$SO$_4$, and concentrated to afford a brown solid, which was purified by column chromatography to furnish the pure product (38 mg, 56% yield) as white solid. $^1$H NMR (CDCl$_3$, 300 MHz) δ: 8.00 (d, J=1.8 Hz, 1H), 7.82 (d, J=8.7 Hz, 1H), 7.40 (dd, J=2.1, 8.7 Hz, 1H), 7.13-7.06 (m, 1H), 6.89-6.82 (m, 1H), 6.08 (bs, 1H), 5.49 (s, 2H), 4.47 (d, J=6.0 Hz, 2H), 2.63 (q, J=7.2 Hz, 4H), 1.12 (t, J=7.2 Hz, 6H).

Example 11

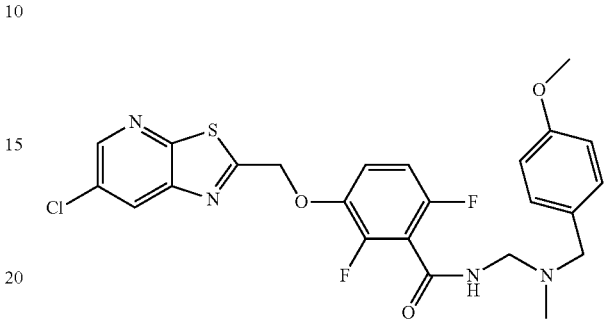

In a sealed tube, mixture of benzamide 5a (38 mg, 0.11 mmol), formaldehyde (37% in water, 0.043 mL, 0.55 mmol), 1-(4-methoxyphenyl)-N-methylmethanamine hydrochloride (102 mg, 0.55 mmol), and 1 N NaOH (0.5 mL) in H$_2$O:THF (1 mL:0.5 mL) was heated at 65° C. for 2 hours. After cooling to room temperature, the reaction mixture was diluted with ethyl acetate, washed with brine, dried over Na$_2$SO$_4$, and concentrated, then purified by column chromatography to afford the pure product (28 mg, 42% yield) as off white solid. $^1$H NMR (CDCl$_3$, 300 MHz) δ: 8.57 (d, J=2.1 Hz, 1H), 8.24 (d, J=3.0 Hz, 1H), 7.23 (d, J=8.7 Hz, 2H), 7.15-7.08 (m, 1H), 6.91-6.83 (m, 1H), 6.85 (d, J=7.8 Hz, 2H), 6.25 (bs, 1H), 5.48 (s, 2H), 4.39 (d, J=6.0 Hz, 2H), 3.79 (s, 3H), 3.60 (s, 2H), 2.33 (s, 3H).

Example 12

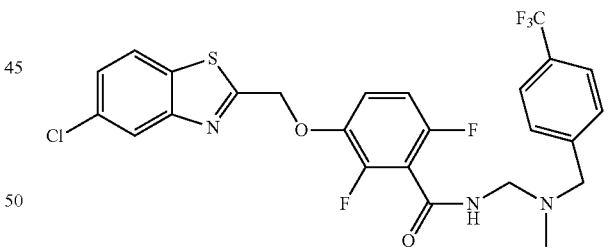

Example 10

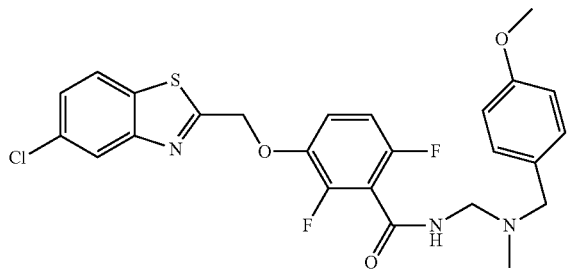 [SMILES: COc1ccc(CN(C)CNC(=O)c2c(F)ccc(OCc3nc4cc(Cl)ccc4s3)c2F)cc1]

In a sealed tube, mixture of benzamide 3a (38 mg, 0.11 mmol), formaldehyde (37% in water, 0.043 mL, 0.55 mmol), 1-(4-methoxyphenyl)-N-methylmethanamine hydrochloride (102 mg, 0.55 mmol), and 1 N NaOH (0.5 mL) in H$_2$O:THF (1 mL: 0.5 mL) was heated at 65° C. for 2 hours. After cooling to room temperature, the reaction mixture was diluted with ethyl acetate, washed with brine, dried over Na$_2$SO$_4$, and concentrated, then purified by column chromatography to afford the pure product (28 mg, 51% yield)

In a sealed tube, mixture of benzamide 3a (38 mg, 0.11 mmol), formaldehyde (37% in water, 0.043 mL, 0.55 mmol), and N-methyl-1-(4-(trifluoromethyl)phenyl)methanamine (104 mg, 0.55 mmol) in H$_2$O:THF (1 mL: 0.5 mL) was heated at 65° C. for 2 hours. After cooling to room temperature, the reaction mixture was diluted with ethyl acetate, washed with brine, dried over Na$_2$SO$_4$, and concentrated, then purified by column chromatography to afford the pure product (31 mg, 55% yield) as off white solid. $^1$H NMR (CDCl$_3$, 300 MHz) δ: 8.00 (d, J=2.1 Hz, 1H), 7.82 (d, J=8.7 Hz, 1H), 7.57 (d, J=7.8 Hz, 2H), 7.46 (d, J=8.1 Hz, 2H), 7.40 (dd, J=2.1, 8.7 Hz, 1H), 7.16-7.08 (m, 1H), 6.91-6.85 (m, 1H), 6.26 (bs, 1H), 5.50 (s, 2H), 4.42 (d, J=6.3 Hz, 2H), 3.73 (s, 2H), 2.33 (s, 3H).

Example 13

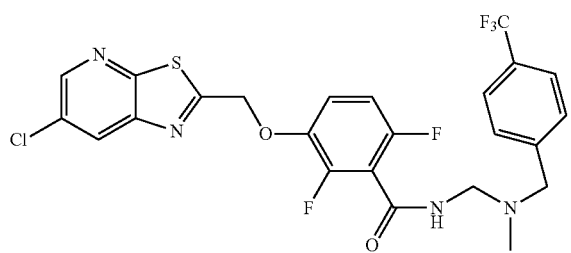 [SMILES: CN(CNC(=O)c1c(F)ccc(OCc2nc3cc(Cl)cnc3s2)c1F)Cc1ccc(C(F)(F)F)cc1]

In a sealed tube, mixture of benzamide 5a (38 mg, 0.11 mmol), formaldehyde (37% in water, 0.043 mL, 0.55 mmol), and N-methyl-1-(4-(trifluoromethyl)phenyl)methanamine (104 mg, 0.55 mmol) in H$_2$O:THF (1 mL: 0.5 mL) was heated at 65° C. for 2 hours. After cooling to room temperature, the reaction mixture was diluted with ethyl acetate, washed with brine, dried over Na$_2$SO$_4$, and concentrated, then purified by column chromatography to afford the pure product (27 mg, 45% yield) as off white solid. $^1$H NMR (CDCl$_3$, 300 MHz) δ: 8.58 (d, J=2.1 Hz, 1H), 8.24 (d, J=2.4 Hz, 1H), 7.58 (d, J=8.1 Hz, 2H), 7.46 (d, J=8.4 Hz, 2H), 7.17-7.09 (m, 1H), 6.93-6.86 (m, 1H), 6.25 (bs, 1H), 5.49 (s, 2H), 4.43 (d, J=6.0 Hz, 2H), 3.74 (s, 2H), 2.34 (s, 3H).

Example 14

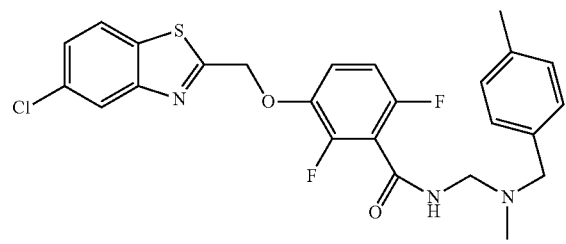 [SMILES: Cc1ccc(CN(C)CNC(=O)c2c(F)ccc(OCc3nc4cc(Cl)ccc4s3)c2F)cc1]

In a sealed tube, mixture of benzamide 3a (38 mg, 0.11 mmol), formaldehyde (37% in water, 0.027 mL, 0.33 mmol), and N-methyl-1-(p-tolyl)methanamine (45 mg, 0.33 mmol) in H$_2$O:THF (1 mL:0.5 mL) was heated at 65° C. for 2 hours. After cooling to room temperature, the reaction mixture was diluted with ethyl acetate, washed with brine, dried over Na$_2$SO$_4$, and concentrated, then purified by column chromatography to afford the pure product (31 mg, 52% yield) as off white solid. $^1$H NMR (CDCl$_3$, 300 MHz) δ: 8.00 (d, J=2.1 Hz, 1H), 7.82 (d, J=8.7 Hz, 1H), 7.40 (dd, J=2.1, 8.7 Hz, 1H), 7.21 (d, J=8.1 Hz, 2H), 7.12 (d, J=7.8 Hz, 2H), 7.15-7.07 (m, 1H), 6.90-6.84 (m, 1H), 6.17 (bs, 1H), 5.50 (s, 2H), 4.39 (d, J=6.3 Hz, 2H), 3.63 (s, 2H), 2.34 (s, 3H), 2.32 (s, 3H).

Example 15

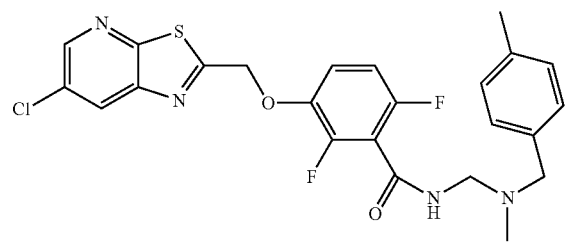 [SMILES: Cc1ccc(CN(C)CNC(=O)c2c(F)ccc(OCc3nc4cc(Cl)cnc4s3)c2F)cc1]

In a sealed tube, mixture of benzamide 5a (38 mg, 0.11 mmol), formaldehyde (37% in water, 0.027 mL, 0.33 mmol), and N-methyl-1-(p-tolyl)methanamine (45 mg, 0.33 mmol) in H$_2$O:THF (1 mL:0.5 mL) was heated at 65° C. for 2 hours. After cooling to room temperature, the reaction mixture was diluted with ethyl acetate, washed with brine, dried over Na$_2$SO$_4$, and concentrated, then purified by column chromatography to afford the pure product (31 mg, 35% yield) as off white solid. $^1$H NMR (CDCl$_3$, 300 MHz) δ: 8.58 (d, J=2.1 Hz, 1H), 8.24 (d, J=2.4 Hz, 1H), 7.21 (d, J=8.1 Hz, 2H), 7.12 (d, J=7.8 Hz, 2H), 7.16-7.08 (m, 1H), 6.92-6.86 (m, 1H), 6.17 (bs, 1H), 5.48 (s, 2H), 4.39 (d, J=6.3 Hz, 2H), 3.63 (s, 2H), 2.34 (s, 3H), 2.32 (s, 3H).

Example 16

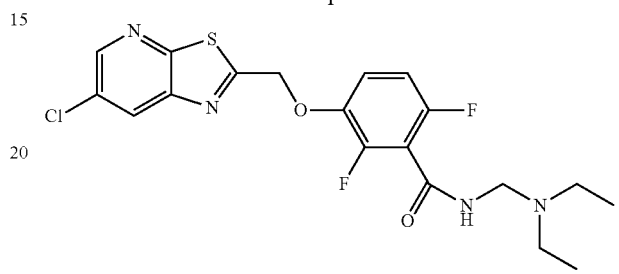

In a sealed tube, mixture of benzamide 5a (25 mg, 0.07 mmol), formaldehyde (37%, 0.028 mL, 0.35 mmol) and diethylamine (26 mg, 0.35 mmol) in H$_2$O:THF (1 mL: 0.5 mL) was heated at 65° C. for 2 hours. After cooling to room temperature, the reaction mixture was diluted with ethyl acetate, washed with brine, dried over Na$_2$SO$_4$, and concentrated to afford a brown solid, which was purified by column chromatography to furnish the pure product (12 mg, 39% yield) as white solid. $^1$H NMR (CDCl$_3$, 300 MHz) δ: 8.57 (d, J=2.4 Hz, 1H), 8.23 (d, J=2.4 Hz, 1H), 7.15-7.07 (m, 1H), 6.90-6.84 (m, 1H), 6.09 (bs, 1H), 5.48 (s, 2H), 4.47 (d, J=6.0 Hz, 2H), 2.63 (q, J=7.2 Hz, 4H), 2.12 (t, J=7.2 Hz, 6H).

Example 17

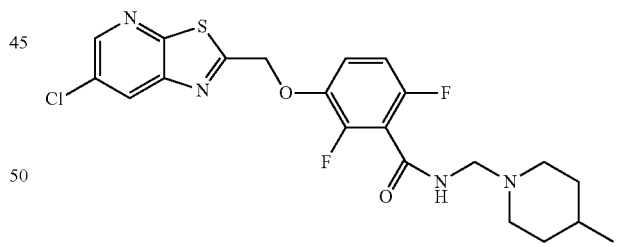

In a sealed tube, mixture of benzamide 5a (28 mg, 0.08 mmol), formaldehyde (37%, 0.032 mL, 0.40 mmol) and 4-methylpiperidine (40 mg, 0.40 mmol) in H$_2$O:THF (1 mL: 0.5 mL) was heated at 65° C. for 2 hours. After cooling to room temperature, the reaction mixture was diluted with ethyl acetate, washed with brine, dried over Na$_2$SO$_4$, concentrated, then purified by column chromatography to afford the pure product (13 mg, 35% yield) as white solid. $^1$H NMR (CDCl$_3$, 300 MHz) δ: 8.57 (d, J=2.4 Hz, 1H), 8.23 (d, J=2.4 Hz), 7.15-7.07 (m, 1H), 6.90-6.84 (m, 1H), 6.21 (bs, 1H), 5.48 (s, 2H), 4.34 (d, J=6.3 Hz, 2H), 1.93-1.81 (m, 2H), 1.34-1.26 (m, 2H), 1.70-1.61 (m, 2H), 1.41-1.15 (m, 3H), 0.92 (d, J=6.3 Hz, 3H).

Example 18

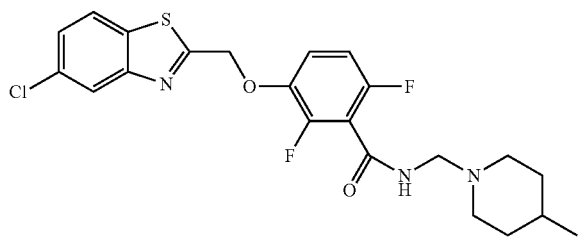 [SMILES: CC1CCN(CNC(=O)c2c(F)ccc(OCc3nc4cc(Cl)ccc4s3)c2F)CC1]

In a sealed tube, mixture of benzamide 3a (30 mg, 0.084 mmol), formaldehyde (37%) (0.010 mL) and amine (0.050 mL) in $H_2O$:THF (2:1) was heated at 65° C. for 2 hours. After cooling to room temperature, the reaction mixture was diluted with ethyl acetate, washed with brine, dried over $Na_2SO_4$, concentrated, then purified by column chromatography to afford the pure product (20 mg, 53% yield). $^1$H NMR ($CD_3OD$, 400 MHz) δ: 7.92-7.90 (m, 2H), 7.36 (dd, J=8.5 Hz, J=2.1 Hz, 1H), 7.28-7.22 (m, 1H), 6.93-6.88 (m, 1H), 5.50 (s, 2H), 4.17 (s, 2H), 2.78-2.75 (m, 2H), 2.31-2.25 (m, 2H), 1.59-1.56 (m, 2H), 1.25-1.22 (m, 1H), 1.19-1.11 (m, 2H), 0.84 (d, J=6.3 Hz, 3H).

Example 19

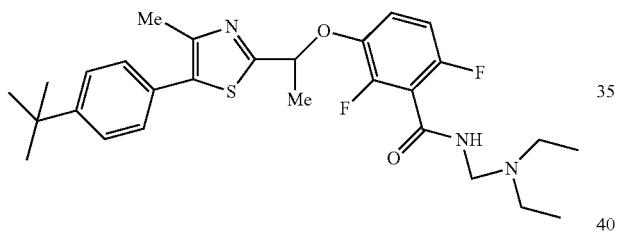

In a sealed tube, mixture of benzamide 19e (20 mg, 0.046 mmol), formaldehyde (37%) (0.030 mL) and diethyl amine (0.030 mL) in $H_2O$:THF (1.0 mL: 0.5 mL) was heated at 65° C. for 2 hours. After cooling to room temperature, the reaction mixture was diluted with ethyl acetate, washed with brine, dried over $Na_2SO_4$, concentrated, then purified by column chromatography to afford the pure product as colorless oil (15 mg, 62% yield). $^1$H NMR ($CDCl_3$, 300 MHz) δ 7.42 (d, J=8.7 Hz, 2H), 7.33 (d, J=8.7 Hz, 2H), 7.11-7.03 (m, 1H), 6.83-6.77 (m, 1H), 6.09 (bs, 1H), 5.50 (q, J=6.5 Hz, 1H), 4.46 (d, J=6.0 Hz, 2H), 2.62 (q, J=7.2 Hz, 4H), 2.27 (s, 3H), 1.80 (d, J=6.61 Hz, 3H), 1.33 (s, 9H), 1.11 (t, J=7.2 Hz, 6H).

The requisite intermediates were prepared as follows a. Preparation of Compound

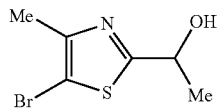

To a solution of 4-methylthiazole-2-aldehyde (1 g, 7.8 mmol) in anhdrous THF (17 mL) was added a THF solution of MeMgBr (5.2 mL, 15.6 mmol) drop-wise at −60° C. under $N_2$ and the mixture was warmed to room temperature and was stirred for another 2 hours. After the TLC shows completion of the reaction, the reaction was quenched by addition of saturated $NH_4Cl$ and was extracted with EtOAc. The combined organic layers were washed with brine, dried and concentrated. Purification of the crude product by ISCO gave the pure product as yellow oil (850 mg, 76% yield). $^1$H NMR ($CDCl_3$, 300 MHz) δ 6.85 (s, 1H), 5.14 (qt, J=6.0 Hz, 1H), 2.45 (s, 3H), 1.16 (d, J=6.0 Hz, 3H).

b. Preparation of Compound

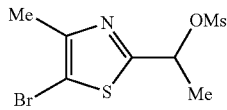 [SMILES: Cc1nc(C(C)OS(C)(=O)=O)sc1Br]

To a solution of 1-(4-methylthiazole-2-yl)ethanol 19a (750 mg, 5.25 mmol) in DMF (18 mL) was added NBS (1.02 g, 5.78 mmol) and the mixture was stirred at 50° C. for 2 hours. After the completion of the reaction, the mixture was diluted with water and was extracted with ethyl acetate. The combined organic extracts were washed with brine, dried over $Na_2SO_4$ and concentrated under reduced pressure to give a residue which was purified in ISCO to give the pure product as yellow oil (650 mg, 56% yield). $^1$H NMR ($CDCl_3$, 300 MHz) δ 5.00 (qt, J=6.6 Hz, 1H), 3.78 (bs, 1H), 2.33 (s, 3H), 1.56 (d, J=6.6 Hz, 3H).

c. Preparation of Compound

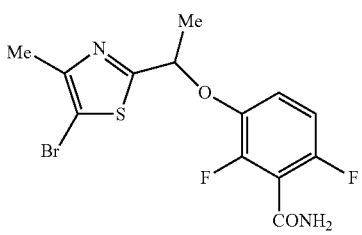 [SMILES: Cc1nc(C(C)Oc2ccc(F)c(C(N)=O)c2F)sc1Br]

A 25-mL round bottom flask equipped with a magnetic stirrer under nitrogen was charged with alcohol 19b (70 mg, 0.315 mmol), $CH_2Cl_2$ (3.0 mL), and triethylamine (0.09 ml, 0.630 mmol). Methanesulfonyl chloride (0.037 mL, 0.437 mmol) was added via a syringe over 1 minutes. The resulting reaction mixture was stirred at room temperature overnight. The reaction mixture was concentrated under reduced pressure to afford the crude product (52 mg, 55% yield), which was used without further purification.

d. Preparation of Compound

A 25-mL round bottom flask equipped with a magnetic stirrer, a condenser and a nitrogen in/outlet adapter was charged with mesylate 19c (50 mg, 0.166 mmol), DMF (3.0 mL), K₂CO₃ (55 mg, 0.4 mmol), and phenol (31 mg, 0.18 mmol) The reaction mixture was stirred at 50° C. for 12 hours. The reaction mixture was diluted with EtOAc (25 mL), washed with water (5 mL), 10% LiCl (5 mL), brine (5 mL), dried over Na₂SO₄, concentrated, and purified on silica gel. Elution with 70% EtOAc/hexanes afforded the title compound as colorless oil (62 mg, 99% yield). ¹H NMR (CDCl₃, 300 MHz) δ 7.11-7.03 (m, 1H), 6.85 (m, 1H), 6.03 (bs, 2H), 5.45 (qt, 1H), 2.28 (s, 3H), 1.76 (d, J=6.6 Hz, 3H).

e. Preparation of Compound

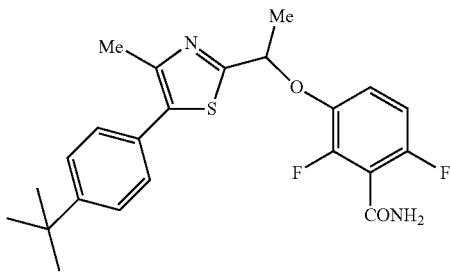 [SMILES: Cc1nc(C(C)Oc2ccc(F)c(C(N)=O)c2F)sc1-c1ccc(C(C)(C)C)cc1]

A 25-mL round bottom flask equipped with a magnetic stirrer, a condenser and a nitrogen in/outlet adapter was charged with bromo compound 19d (57 mg, 0.151 mmol), 4-tert-butylphenylboronic acid (77 m g, 0.43 mmol), water/dioxane (3.0 mL/1.0 mL), K₂CO₃ (70.0 mg, 0.5 mmol). The resulting solution was degassed for 5 minutes, then Pd(PPh₃)₄ (20 mg) was added. The reaction mixture was warmed to 100° C. and stirred for 30 minutes. After cooled to room temperature, the reaction mixture was diluted with EtOAc and washed with saturated NaHCO₃, brine, dried over Na₂SO₄. The organic layer was concentrated under reduced pressure and purified on silica gel. Elution with 1:1 EtOAc/hexanes solvent system afforded the desired compound as colorless solid (50 mg, 77% yield). ¹H NMR (CDCl₃, 300 MHz) δ 7.45 (d, J=9.0 Hz, 2H), 7.37 (d, J=9.0 Hz, 2H), 7.19-7.11 (m, 1H), 6.89-6.83 (m, 1H), 6.00 (bs, 2H), 5.55 (qt, 1H), 2.51 (s, 3H), 1.84 (d, J=6.6 Hz, 3H), 1.31 (s, 9H).

Example 20

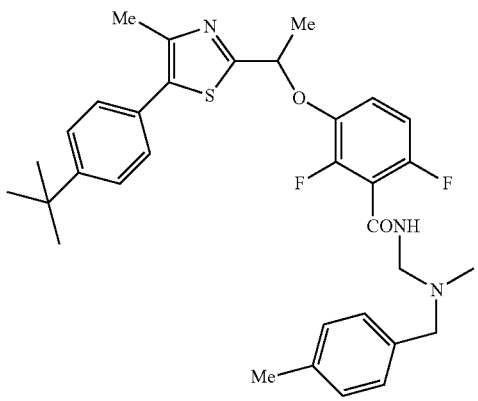

In a sealed tube, mixture of benzamide 19e (20 mg, 0.046 mmol), aldehyde (0.08 mL) and amine (0.08 mL) in H₂O:THF (1.0 mL: 0.5 mL) was heated at 65° C. for 2 hours. After cooling to room temperature, the reaction mixture was diluted with ethyl acetate, washed with brine, dried over Na₂SO₄, and concentrated, then purified by column chromatography to afford the pure product (12 mg, 44% yield) as white solid. ¹H NMR (CDCl₃, 300 MHz) δ ¹H NMR (CDCl₃, 300 MHz) δ: 7.42 (d, J=8.7 Hz, 2H), 7.34 (d, J=8.7 Hz, 2H), 7.20 (d, J=7.5 Hz, 2H), 7.13-7.05 (m, 3H), 6.85-6.78 (m, 1H), 6.17 (bs, 1H), 5.52 (q, J=6.6 Hz, 1H), 4.39 (d, J=6.3 Hz, 2H), 3.62 (s, 2H), 2.47 (s, 3H), 2.33 (s, 3H), 2.32 (s, 3H), 1.81 (d, J=6.60 Hz, 3H), 1.33 (s, 9H).

Example-21

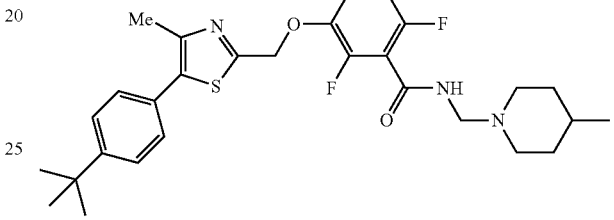

In a sealed tube, mixture of benzamide (30 mg, 0.07 mmol), formaldehyde (37%) (0.01 mL, 0.36 mmol), and amine (0.04 mL, 0.36 mmol) in H₂O:THF (2:1) was heated at 65° C. for 2 hours. The reaction mixture was cooled to room temperature. Extraction with ethyl acetate (×3) afforded a brown solid which was then purified by column chromatography to furnish 9 mg of the pure product. yield (minus recovered SM): 60%. ¹H NMR (CD₃OD, 400 MHz) δ: 7.30-7.26 (m, 4H), 7.24-7.21 (m, 1H), 6.93-6.88 (m, 1H), 5.30 (s, 2H), 4.17 (s, 2H), 2.78-2.75 (m, 2H), 2.36 (s, 3H), 2.32-2.26 (m, 2H), 1.59-1.56 (m, 2H), 1.25 (s, 9H), 1.18-1.09 (m, 3H), 0.83 (d, J=6.4 Hz, 3H).

The requisite intermediates were prepared as follows:

a. Preparation of Compound

A 50-mL round bottom flask equipped with a magnetic stirrer was charged commercially available thiazole aldehyde (382 mg, 2.94 mmol), ethanol (95%, 10 mL), NaBH₄ (112 mg, 2.94 mmol) was added in several portions. The reaction mixture was stirred at room temperature for 1 hour. Acetone (1 mL) was added to the reaction mixture. After 20 minutes, the reaction mixture was concentrated and the residue was partition between EtOAc (50 mL) and 1 N HCl (15 mL). The organic layer was washed with saturated NaHCO₃ (15 mL), brine (15 mL), dried over Na₂SO₄, concentrated under reduced pressure and purified on silica gel. Elution with 10% EtOAc/Hexanes afforded the reduced compound (350 mg, 92% yield). ¹H NMR (CDCl₃, 400 MHz) δ: 6.75 (s, 1H), 5.84 (bs, 1H), 4.79 (s, 2H), 2.31 (s, 3H).

b. Preparation of Compound

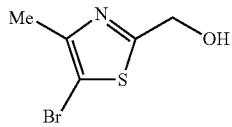

To a solution of thiazole 21a (720 mg, 5.58 mmol) in DMF (15 mL) was added NBS (1.1 g, 6.14 mmol) and the mixture was stirred at 50° C. for 2 hours. After the completion of the reaction, the mixture was diluted with water and was extracted with ethyl acetate. The combined organic extracts were washed with brine, dried over $Na_2SO_4$ and concentrated under reduced pressure to give a residue which was purified in ISCO max gradient 40% EtOAc/hexane to give the pure product (870 mg, 75% yield). $^1$H NMR (CDCl$_3$, 400 MHz) δ: 4.83 (s, 2H), 4.01 (bs, 1H), 2.36 (s, 3H).

c. Preparation of Compound

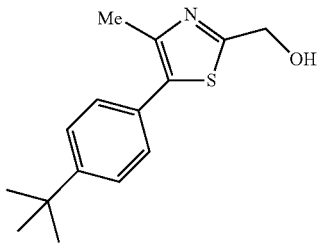 [SMILES: Cc1nc(CO)sc1-c1ccc(C(C)(C)C)cc1]

A 25-mL round bottom flask equipped with a magnetic stirrer, a condenser and a nitrogen in/outlet adapter was charged with bromo compound 21b (200 mg, 0.96 mmol), 4-tert-butylphenylboronic acid (205 mg, 1.15 mmol), water/dioxane (3 mL/6 ml), $K_2CO_3$ (398 mg, 2.9 mmol). The resulting solution was degassed for 5 minutes, then Pd(OAc)$_2$ (22 mg, 0.09 mmol) and XPhos (92 mg, 0.19 mmol) was added. The reaction mixture was warmed to 100° C. and stirred overnight. After cooled to room temperature, the reaction mixture was diluted with EtOAc (75 mL) and washed with saturated NaHCO$_3$ (25 mL), dried over Na$_2$SO$_4$. The organic layer was concentrated under reduced pressure and purified on an ISCO using a maximum gradient of 70% EtOAc/hexane to give the title compound (72 mg, 29% yield). $^1$H NMR (CDCl$_3$, 400 MHz) δ: 7.47-7.36 (m, 4H), 4.92 (s, 2H), 4.46 (bs, 1H), 2.51 (s, 3H), 1.37 (s, 9H).

d. Preparation of Compound

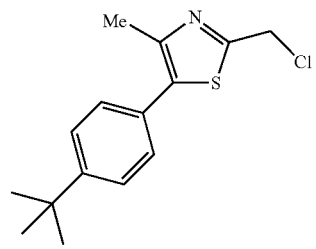 [SMILES: Cc1nc(CCl)sc1-c1ccc(C(C)(C)C)cc1]

A 25-mL round bottom flask equipped with a magnetic stirrer under nitrogen was charged with alcohol 21c (75 mg, 0.29 mmol), CH$_2$Cl$_2$ (3 mL), and triethylamine (0.1 mL, 0.72 mmol). Methanesulfonyl chloride (0.05 mL, 0.57 mmol) was added via a syringe over 5 minutes. The resulting reaction mixture was stirred at room temperature overnight. The reaction mixture was diluted with CH$_2$Cl$_2$ (30 mL) and washed with saturated NaHCO$_3$ (15 ml), dried over Na$_2$SO$_4$, and concentrated under reduced pressure and purified on an ISCO using a maximum gradient of 30% EtOAc/hexane affording title compound (72 mg, 89% yield). $^1$H NMR (CDCl$_3$, 400 MHz) δ: 7.49-7.38 (m, 4H), 4.83 (s, 2H), 2.52 (s, 3H), 1.38 (s, 9H).

e. Preparation of Compound

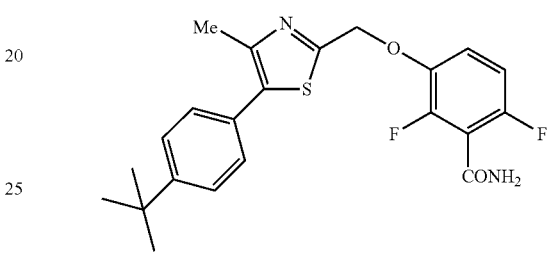

A 25-mL round bottom flask equipped with a magnetic stirrer, a condenser and a nitrogen in/outlet adapter was charged with chloro intermediate 21d (71 mg, 0.25 mmol), DMF (3 mL), K$_2$CO$_3$ (50 mg, 0.36 mmol), and phenol (42 mg, 0.24 mmol) The reaction mixture was stirred at room temperature overnight. The reaction mixture was diluted water (30 mL) and precipitate was filtered off and washed with additional water (3 mL) then dissolved in DCM and concentrated. Purification on an ISCO using a maximum gradient of 2% MeOH/DCM to give the title compound (103 mg, 99% yield). $^1$H NMR (CD$_3$OD, 400 MHz) δ: 7.50-7.37 (m, 4H), 7.34-7.28 (m, 1H), 6.99-6.96 (m, 1H), 5.38 (s, 2H), 2.45 (s, 3H), 1.35 (s, 9H).

Example 22

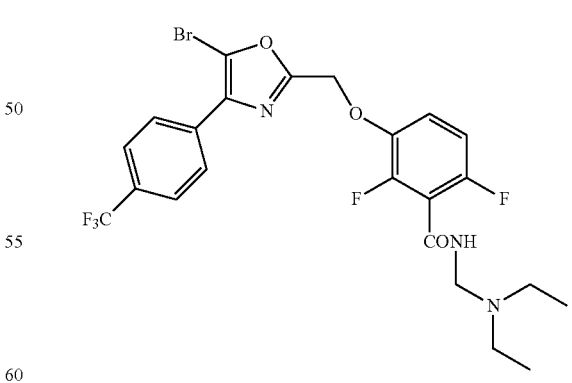

In a sealed tube, mixture of benzamide 22d (20 mg, 0.041 mmol), formaldehyde (37%) (0.030 mL) and diethyl amine (0.03 mL) in H$_2$O:THF (1.0 ml: 0.5 ml) was heated at 65° C. for 2 hours. After cooling to room temperature, the reaction mixture was diluted with ethyl acetate, washed with brine, dried over Na$_2$SO$_4$, and concentrated to afforded a brown solid, which was purified by column chromatography to afford the pure product as clear oil (13 mg, 56% yield). $^1$H NMR (CDCl$_3$, 300 MHz) δ 8.08 (d, J=8.4 Hz, 2H), 7.70 (d, J=8.4 Hz, 2H), 7.17 (m, 1H), 6.90 (m, 1H), 5.20 (s, 2H), 4.53 (d, 2H), 2.76 (qt, 4H), 1.22 (t, 6H).

The requisite intermediates were prepared as follows a. Preparation of Compound

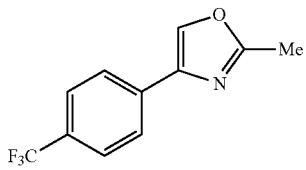

A mixture of 4-trifluoromethylphenacyl bromide (1.14 g, 4.28 mmol) and acetamide (550 mg, 8.56 mmol) was heated to 110° C. for 2 h. When the reaction was complete, water was added and the mixture was washed with ethyl acetate (3×100 mL). The combined organic layers were washed with water, dried with Na$_2$SO$_4$, filtered and concentrated. The crude mixture was purified by ISCO using 5% EtOAC/hexane to give an off white solid (700 mg, 59% yield). $^1$H NMR (CDCl$_3$, 300 MHz) δ 7.88 (s, 1H), 7.81 (d, J=8.1 Hz, 2H), 7.63 (d, J=8.4 Hz, 2H), 2.52 (s, 3H).

b. Preparation of Compound

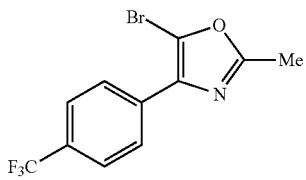 [SMILES: Cc1nc(-c2ccc(C(F)(F)F)cc2)c(Br)o1]

To a solution of oxazole 22a (294 mg, 1.3 mmol) in AcOH (5.0 mL) was added NBS (230 mg, 1.3 mmol) and the resulting mixture was stirred at room temperature for 3 hours. After the completion of the reaction the mixture was poured onto crushed ice and the product was extracted with ethyl acetate (3×). The combined organic layers were washed with saturated NAHCO$_3$ solution and brine, dried over Na$_2$SO$_4$, filtered and concentrated. The residue was purified by ISCO to give the product as a white solid (345 mg, 87% yield). $^1$H NMR (CDCl$_3$, 300 MHz) δ: 8.06 (d, J=9.0 Hz, 2H), 7.68 (d, J=9.0 Hz, 2H), 2.53 (s, 3H).

c. Preparation of Compound

To a solution of oxazole 22b (340 mg, 1.11 mmol) in CCl4 (8.0 mL) was added NBS (205 mg, 1.15 mmol) and AIBN (28 mg, 0.17 mmol). The resulting mixture was heated to 80° C. for 3 hours. The mixture was filtered, concentrated under reduced pressure and purified by ISCO to give the pure product (110 mg, 26% yield) along with dibromo product and recovered starting material. $^1$H NMR (CDCl$_3$, 300 MHz) δ 8.08 (d, J=8.4 Hz, 2H), 7.69 (d, J=8.4 Hz, 2H), 4.48 (s, 2H).

d. Preparation of Compound

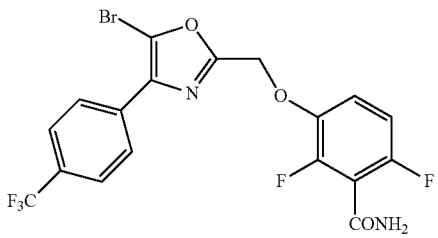 [SMILES: NC(=O)c1c(F)ccc(OCc2nc(-c3ccc(C(F)(F)F)cc3)c(Br)o2)c1F]

A 25-mL round bottom flask equipped with a magnetic stirrer, a condenser and a nitrogen in/outlet adapter was charged with bromomethyl intermediate 22c (70 mg, 0.181 mmol), DMF (2.5 mL), K$_2$CO$_3$ (50 mg, 0.36 mmol), and phenol (60 mg, 0.346 mmol). The reaction mixture was stirred at 50° C. for 4 hours. The reaction mixture was diluted with EtOAc, washed with water, 10% LiCl, brine, dried over Na$_2$SO$_4$, concentrated, and purified on silica gel. Elution with 70% EtOAc/hexanes afforded the title compound as white solid (50 mg, 58% yield). $^1$H NMR (CDCl$_3$, 300 MHz) δ 8.08 (d, J=8.4 Hz, 2H), 7.69 (d, J=8.4 Hz, 2H), 7.23 (m, 1H), 6.91 (m, 1H), 5.96 (bs, 2H), 5.21 (s, 2H).

Example 23

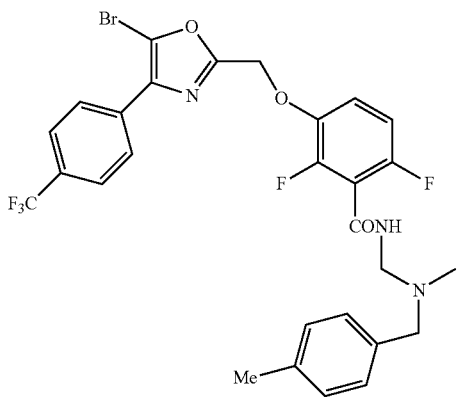

In a sealed tube, mixture of benzamide 22d (30 mg, 0.063 mmol), formaldehyde (37%) (0.040 ml) and N-methyl-1-(p-tolyl)methanamine (0.040 ml) in H$_2$O:THF (1.0 mL: 0.5 mL) was heated at 65° C. for 2 h. After cooling to room temperature, the reaction mixture was diluted with ethyl acetate, washed with brine, dried over Na$_2$SO$_4$, and concentrated to afford a brown solid, which was purified by column chromatography to afford the pure product as white solid (20 mg, 52% yield). $^1$H NMR (CDCl$_3$, 300 MHz) δ 8.08 (d, J=8.4 Hz, 2H), 7.70 (d, J=8.4 Hz, 2H), 7.26-7.12 (m, 5H), 6.94-6.88 (m, 1H), 5.21 (s, 2H), 4.42 (d, J=6.3 Hz, 2H), 3.67 (s, 2H), 2.33 (s, 3H).

Example 24

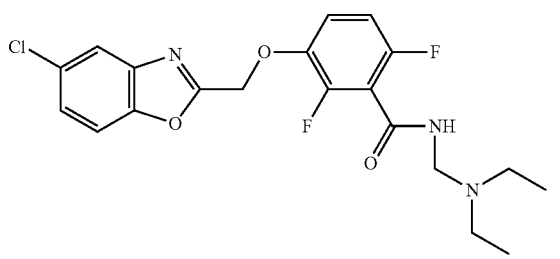 [SMILES: CCN(CC)CNC(=O)c1c(F)ccc(OCc2nc3cc(Cl)ccc3o2)c1F]

In a sealed tube, mixture of benzamide 24b (34 mg, 0.10 mmol), formaldehyde (37%, 41 µl, 0.50 mmol) and diethylamine (37 mg, 0.75 mmol) in H₂O:THF (1 mL:0.5 mL) was heated at 65° C. for 2 hours. After cooling to room temperature, the reaction mixture was diluted with ethyl acetate, washed with brine, dried over Na₂SO₄, and concentrated, and purified by column chromatography to furnish the pure product (38 mg, 64% yield) as light yellow solid. ¹H NMR (CDCl₃, 300 MHz) δ: 7.72 (d, J=2.1 Hz, 1H), 7.49 (d, J=8.7 Hz, 1H), 7.36 (dd, J=2.1, 8.7 Hz, 1H), 7.19-7.12 (m, 1H), 6.82-6.89 (m, 1H), 6.10 (bs, 1H), 5.33 (s, 2H), 4.46 (d, J=6.0 Hz, 2H), 2.61 (q, J=7.2 Hz, 4H), 1.11 (t, J=7.2 Hz, 6H).

The requisite intermediates were prepared as follows a. Preparation of Compound

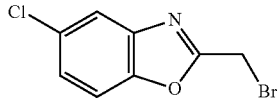 [SMILES: Clc1ccc2oc(CBr)nc2c1]

A mixture of commercially available 5-chloro-2-methylbenzo[d]oxazole (300 mg, 1.79 mmol), NBS (478 mg, 2.70 mmol) in carbon tetrachloride (6 mL) was heated under light for 4 hours. After cooling to room temperature, hexanes was added to the reaction mixture. The solids were filtered and the solvent was removed to give the crude product. Purification using 2% ethyl acetate in hexane afforded the product (124 mg, 28% yield). ¹H NMR (300 MHz, CDCl₃) δ ¹H NMR (CDCl₃, 300 MHz) δ: 7.71 (s, 1H), 7.46 (d, J=9.9 Hz, 1H), 7.36 (d, J=8.7 Hz, 1H), 4.56 (s, 2H).

b. Preparation of Compound

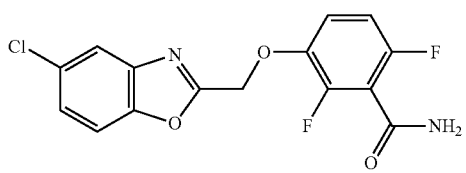 [SMILES: NC(=O)c1c(F)ccc(OCc2nc3cc(Cl)ccc3o2)c1F]

A 25-mL round bottom flask equipped with a magnetic stirrer was charged with 2-(bromomethyl)-5-chlorobenzo[d] oxazole 24a (100 mg, 0.41 mmol), DMF (1.0 mL), K₂CO₃ (104 mg, 0.75 mmol), and 2,6-difluoro-3-hydroxybenzamide (64 mg, 0.37 mmol). The reaction mixture was stirred at room temperature for 12 hours then water was added. The solid was collected by filtration and washed with water. After air drying, the solid was triturated with CH₂Cl₂. There was obtained the desired product (102 mg, 81% yield) as brown solid. ¹H NMR (DMSO, 300 MHz) δ: 8.18 (s, 1H), 7.95-7.83 (m, 3H), 7.51 (dd, J=2.4, 9.0 Hz, 1H), 7.44-7.36 (m, 1H), 7.15-7.08 (m, 1H), 5.60 (s, 2H).

Example 25

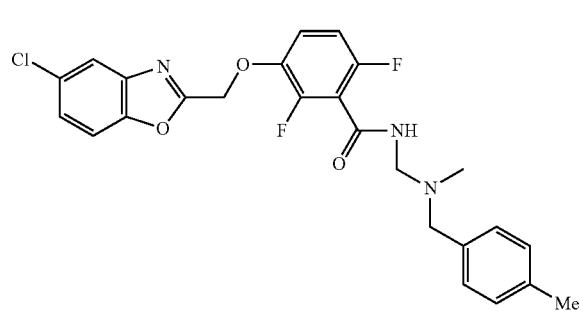 [SMILES: Cc1ccc(CN(C)CNC(=O)c2c(F)ccc(OCc3nc4cc(Cl)ccc4o3)c2F)cc1]

In a sealed tube, mixture of benzamide 24b (38 mg, 0.11 mmol), formaldehyde (37% in water, 0.027 mL, 0.33 mmol), and N-methyl-1-(p-tolyl)methanamine (45 mg, 0.33 mmol) in H₂O:THF (1 mL: 0.5 mL) was heated at 65° C. for 2 hours. After cooling to room temperature, the reaction mixture was diluted with ethyl acetate, washed with brine, dried over Na₂SO₄, and concentrated, then purified by column chromatography to afford the pure product (33 mg, 61% yield) as yellow solid. ¹H NMR (CDCl₃, 300 MHz) δ: ¹H NMR (CDCl₃, 300 MHz) δ: 7.73 (d, J=1.8 Hz, 1H), 7.49 (d, J=8.7 Hz, 1H), 7.36 (dd, J=1.8, 8.7 Hz, 1H), 7.20 (d, J=7.8 Hz, 2H), 7.20-7.13 (m, 1H), 7.12 (d, J=8.1 Hz, 2H), 6.90-6.84 (m, 1H), 6.16 (bs, 1H), 5.34 (s, 2H), 4.38 (d, J=6.3 Hz, 2H), 3.61 (s, 2H), 2.33 (s, 3H), 2.32 (s, 3H).

Example 26

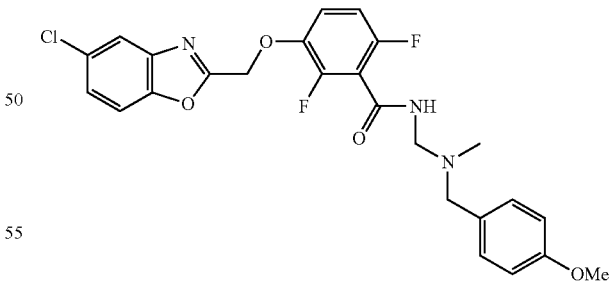

In a sealed tube, mixture of benzamide 24b (38 mg, 0.11 mmol), formaldehyde (37% in water, 0.043 mL, 0.55 mmol), 1-(4-methoxyphenyl)-N-methylmethanamine hydrochloride (102 mg, 0.55 mmol), and 1 N NaOH (0.5 mL) in H₂O:THF (1 mL:0.5 mL) was heated at 65° C. for 2 hours. After cooling to room temperature, the reaction mixture was diluted with ethyl acetate, washed with brine, dried over Na₂SO₄, and concentrated, then purified by column chromatography to afford the pure product (28 mg, 57% yield)

as off white solid. $^1$H NMR (CDCl$_3$, 300 MHz) δ: $^1$H NMR (CDCl$_3$, 300 MHz) δ: 7.73 (d, J=1.8 Hz, 1H), 7.49 (d, J=8.7 Hz, 1H), 7.36 (dd, J=1.8, 8.7 Hz, 1H), 7.23 (d, J=8.7 Hz, 2H), 7.20-7.13 (m, 1H), 6.91-6.84 (m, 1H), 6.85 (d, J=8.7 Hz, 2H), 6.17 (bs, 1H), 5.35 (s, 2H), 4.38 (d, J=6.3 Hz, 2H), 3.79 (s, 3H), 3.59 (s, 2H), 2.32 (s, 3H).

Example 27

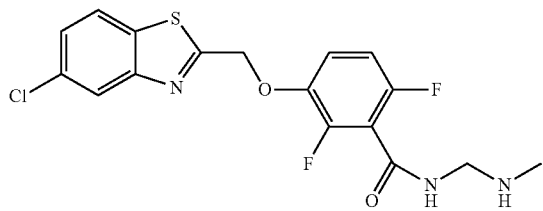 [SMILES: CNCNC(=O)c1c(F)ccc(OCc2nc3cc(Cl)ccc3s2)c1F]

A 25-mL round bottom flask equipped with a magnetic stirrer under nitrogen was charged with the chloride 39b (105 mg, 0.26 mmol), CH$_2$Cl$_2$ (5 mL). After cooling to −30° C., triethylamine (0.18 ml, 1.3 mmol) was added to the reaction mixture, followed by adding methylamine (2 M in THF, 1.5 mL, 3.0 mmol). The reaction mixture was warmed to room temperature and stirred for 1 hour. The solvent was removed and the residue was purified by column chromatography to afford the pure product (40 mg, 39% Yield) as off white solid. $^1$H NMR (CDCl$_3$, 300 MHz) δ: 7.99 (d, J=2.1 Hz, 1H), 7.80 (d, J=8.7 Hz, 1H), 7.38 (dd, J=2.1, 8.7 Hz, 1H), 7.13-7.05 (m, 1H), 6.88-6.81 (m, 1H), 6.36 (bs, 1H), 5.47 (s, 2H), 4.30 (s, 2H), 2.44 (s, 3H).

Example 28

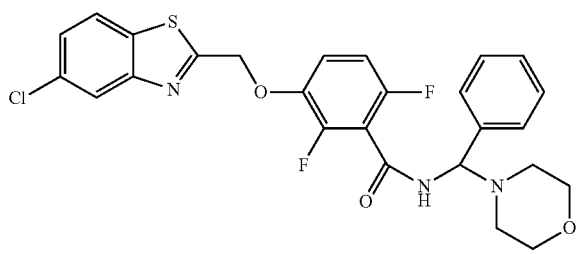 [SMILES: O=C(NC(c1ccccc1)N1CCOCC1)c1c(F)ccc(OCc2nc3cc(Cl)ccc3s2)c1F]

In a sealed tube, mixture of benzamide 3a (35 mg, 0.10 mmol), benzaldehyde (32 mg, 0.30 mmol) and morpholine (26 mg, 0.30 mmol) in EtOH (1.5 mL) was heated at 110° C. for 3 hours. The reaction mixture was cooled to room temperature and the solvent was removed. The residue was purified by column chromatography to afford the pure product (31 mg, 58% yield) as light yellow solid. $^1$H NMR (CDCl$_3$, 300 MHz) δ: 8.00 (d, J=2.1 Hz, 1H), 7.82 (d, J=8.7 Hz, 1H), 7.51 (d, J=7.2 Hz, 2H), 7.41-7.31 (m, 4H), 7.16-7.08 (m, 1H), 6.92-6.85 (m, 1H), 6.38 (d, J=9.9 Hz, 1H), 6.03 (d, J=9.6 Hz, 1H), 5.50 (s, 2H), 3.74-3.70 (m, 4H), 2.71-2.64 (m, 2H), 2.60-2.52 (m, 2H).

Example 29

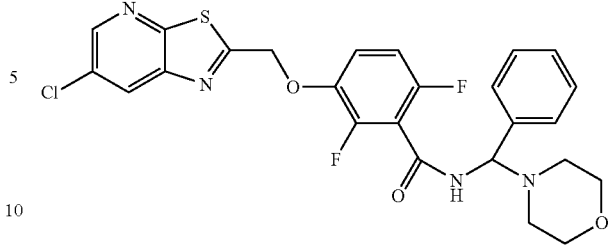

In a sealed tube, mixture of benzamide 5a (36 mg, 0.10 mmol), benzaldehyde (32 mg, 0.30 mmol) and morpholine (26 mg, 0.30 mmol) in EtOH (1.5 mL) was heated at 110° C. for 3 hours. The reaction mixture was cooled to room temperature and the solvent was removed. The residue was purified by column chromatography to afford the pure product (20 mg, 38% yield) as yellow solid. $^1$H NMR (CDCl$_3$, 300 MHz) δ: 8.57 (d, J=2.4 Hz, 1H), 8.23 (d, J=2.4 Hz, 1H), 7.51 (d, J=7.2 Hz, 2H), 7.40-7.28 (m, 3H), 7.17-7.09 (m, 1H), 6.93-6.87 (m, 1H), 6.41 (d, J=9.9 Hz, 1H), 6.03 (d, J=9.6 Hz, 1H), 5.48 (s, 2H), 3.74-3.70 (m, 4H), 2.71-2.64 (m, 2H), 2.60-2.52 (m, 2H).

Example 30

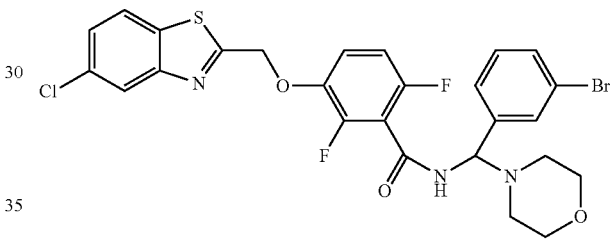

In a sealed tube, mixture of benzamide 3a (35 mg, 0.10 mmol), 3-bromobenzaldehyde (55 mg, 0.30 mmol) and morpholine (26 mg, 0.30 mmol) in EtOH (1.5 mL) was heated at 110° C. for 3 hours. The reaction mixture was cooled to room temperature and the solvent was removed. The residue was purified by column chromatography to afford the pure product (35 mg, 54% yield) as yellow solid. $^1$H NMR (CDCl$_3$, 300 MHz) δ: 8.00 (d, J=2.1 Hz, 1H), 7.82 (d, J=8.7 Hz, 1H), 7.69 (s, 1H), 7.47-7.38 (m, 3H), 7.27-7.22 (m, 1H), 7.18-7.10 (m, 1H), 6.94-6.89 (m, 1H), 6.36 (d, J=9.3 Hz, 1H), 6.02 (d, J=9.9 Hz, 1H), 5.51 (s, 2H), 3.78-3.70 (m, 4H), 2.71-2.64 (m, 2H), 2.60-2.52 (m, 2H).

Example 31

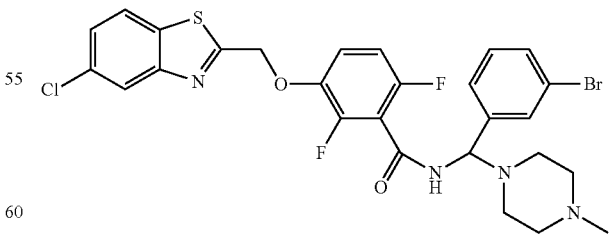

In a sealed tube, mixture of benzamide 3a (35 mg, 0.10 mmol), 3-bromobenzaldehyde (55 mg, 0.30 mmol) and 1-methylpiperazine (30 mg, 0.30 mmol) in EtOH (1.5 mL) was heated at 110° C. for 3 hours. The reaction mixture was cooled to room temperature and the solvent was removed.

The residue was purified by column chromatography to afford the pure product (38 mg, 61% yield) as white solid. ¹H NMR (CDCl₃, 300 MHz) δ 8.00 (d, J=2.1 Hz, 1H), 7.82 (d, J=8.4 Hz, 1H), 7.69 (s, 1H), 7.47-7.38 (m, 3H), 7.27-7.21 (m, 1H), 7.17-7.09 (m, 1H), 6.93-6.86 (m, 1H), 6.33 (d, J=9.6 Hz, 1H), 6.10 (d, J=9.6 Hz, 1H), 5.50 (s, 2H), 2.70-2.41 (m, 8H), 2.29 (s, 3H).

Example 32

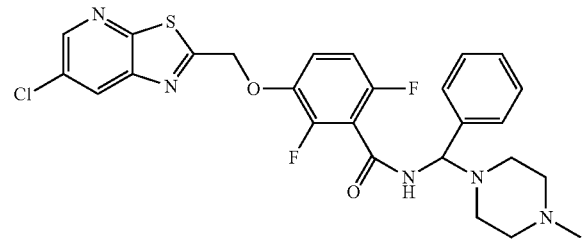 [SMILES: CN1CCN(C(NC(=O)c2c(F)ccc(OCc3nc4cc(Cl)cnc4s3)c2F)c2ccccc2)CC1]

In a sealed tube, mixture of benzamide 5a (36 mg, 0.10 mmol), benzaldehyde (32 mg, 0.30 mmol) and 1-methylpiperazine (30 mg, 0.30 mmol) in EtOH (1.5 mL) was heated at 110° C. for 3 hours. The reaction mixture was cooled to room temperature and the solvent was removed. The residue was purified by column chromatography to afford the pure product (26 mg, 47% yield) as light brown solid. NMR (CDCl₃, 300 MHz) δ:: 8.57 (d, J=2.4 Hz, 1H), 8.23 (d, J=2.4 Hz, 1H), 7.52 (d, J=7.5 Hz, 2H), 7.39-7.28 (m, 3H), 7.17-7.09 (m, 1H), 6.92-6.86 (m, 1H), 6.36 (d, J=9.0 Hz, 1H), 6.11 (d, J=9.3 Hz, 1H), 5.48 (s, 2H), 2.79-2.42 (m, 8H), 2.29 (s, 3H).

Example 33

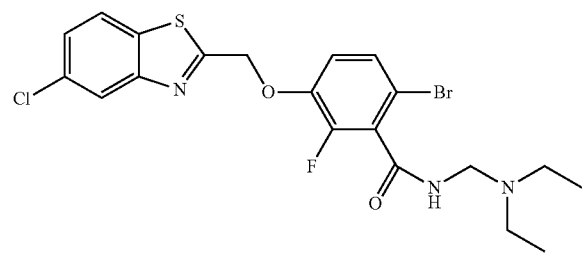 [SMILES: CCN(CC)CNC(=O)c1c(Br)ccc(OCc2nc3cc(Cl)ccc3s2)c1F]

In a sealed tube, mixture of benzamide 33a (42 mg, 0.10 mmol), formaldehyde (37%, 0.041 mL, 0.50 mmol) and diethylamine (37 mg, 0.75 mmol) in H₂O:THF (1 mL: 0.5 mL) was heated at 65° C. for 2 hours. After cooling to room temperature, the reaction mixture was diluted with ethyl acetate, washed with brine, dried over Na₂SO₄, and concentrated, and purified by column chromatography to afford the pure product (29 mg, 58% yield) as off white solid. ¹H NMR (CDCl₃, 300 MHz) δ: ¹H NMR (CDCl₃, 300 MHz) δ: 8.00 (d, J=2.1 Hz, 1H), 7.81 (d, J=8.7 Hz, 1H), 7.40 (dd, J=2.1, 8.7 Hz, 1H), 7.27 (dd, J=1.8, 8.7 Hz, 1H), 6.98 (t, J=8.7 Hz, 1H), 5.98 (bs, 1H), 5.51 (s, 2H), 4.48 (d, J=6.3 Hz, 2H), 2.66 (q, J=7.2 Hz, 4H), 2.13 (t, J=7.2 Hz, 6H).

The requisite intermediate was prepared as follows.

a. Preparation of Compound

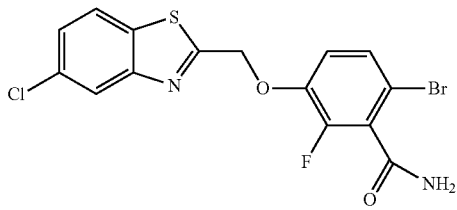 [SMILES: NC(=O)c1c(Br)ccc(OCc2nc3cc(Cl)ccc3s2)c1F]

The compound was prepared using procedures similar to those described in *J. Med. Chem.* 2010, 53, 3927-3936.

Example 34

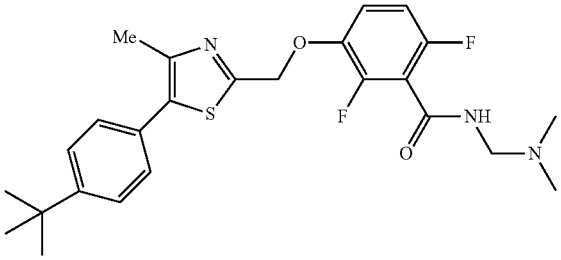 [SMILES: Cc1nc(COc2ccc(F)c(C(=O)NCN(C)C)c2F)sc1-c1ccc(C(C)(C)C)cc1]

In a sealed tube, mixture of benzamide 21e (26 mg, 0.063 mmol), formaldehyde (37%) (0.017 mL, 0.63 mmol) and amine (0.31 mL, 0.63 mmol) in H₂O:THF (2:1) was heated at 65° C. for 2 h. The reaction mixture was cooled to room temperature. Extraction with ethyl acetate (×3) afforded a brown solid which was then purified by column chromatography to furnish 7.8 mg of the pure product. yield (minus recovered SM): 49%. ¹H NMR (CD₃OD, 400 MHz) δ: 7.53-7.40 (m, 4H), 7.40-7.33 (m, 1H), 7.06-7.01 (m, 1H), 5.42 (s, 2H), 4.24 (s, 2H), 2.28 (s, 3H), 2.35 (s, 6H), 1.37 (s, 9H).

Example 35

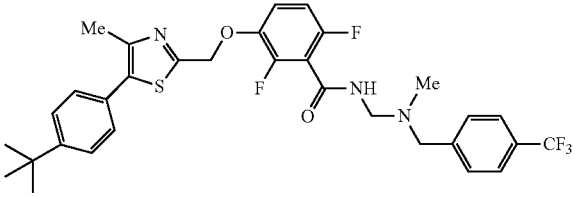 [SMILES: Cc1nc(COc2ccc(F)c(C(=O)NCN(C)Cc3ccc(C(F)(F)F)cc3)c2F)sc1-c1ccc(C(C)(C)C)cc1]

In a sealed tube, mixture of benzamide 21e (22 mg, 0.05 mmol), formaldehyde (37%) (0.015 mL, 0.5 mmol) and amine (0.09 mL, 0.5 mmol) in H₂O:THF (2:1) was heated at 65° C. for 2 h. After cooling to room temperature, the reaction mixture was diluted with ethyl acetate, washed with brine, dried over Na₂SO₄, and concentrated to afforded a brown solid, which was purified by column chromatography to furnish 8.3 mg of the pure product. yield (minus recovered SM): 44%. ¹H NMR (CD₃OD, 400 MHz) δ: 7.52-7.44 (m, 4H), 7.41-7.28 (m, 4H), 7.26-7.22 (m, 1H), 6.95-6.90 (m, 1H), 5.31 (s, 2H), 4.26 (s, 2H), 3.64 (s, 2H), 2.36 (s, 3H), 2.21 (s, 3H), 1.25 (s, 9H).

Example 36

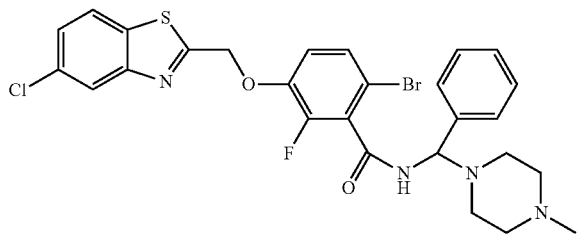 [SMILES: CN1CCN(C(NC(=O)c2c(Br)ccc(OCc3nc4cc(Cl)ccc4s3)c2F)c2ccccc2)CC1]

In a sealed tube, mixture of benzamide 33a (42 mg, 0.10 mmol), benzaldehyde (32 mg, 0.30 mmol) and 1-methylpiperazine (30 mg, 0.30 mmol) in EtOH (1.5 mL) was heated at 110° C. for 3 hours. The reaction mixture was cooled to room temperature and the solvent was removed. The residue was purified by column chromatography to afford the pure product (33 mg, 55% yield) as white solid. $^1$H NMR (CDCl$_3$, 300 MHz) δ: 8.01 (d, J=1.8 Hz, 1H), 7.82 (d, J=8.7 Hz, 1H), 7.56 (d, J=7.5 Hz, 2H), 7.42-7.28 (m, 5H), 7.00 (t, J=8.4 Hz, 1H), 6.23 (d, J=9.6 Hz, 1H), 6.10 (d, J=9.9 Hz, 1H), 5.52 (s, 2H), 2.82-2.39 (m, 8H), 2.29 (s, 3H).

Example 37

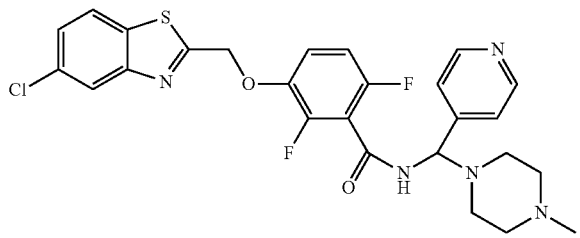 [SMILES: CN1CCN(C(NC(=O)c2c(F)ccc(OCc3nc4cc(Cl)ccc4s3)c2F)c2ccncc2)CC1]

In a sealed tube, mixture of benzamide 3a (35 mg, 0.10 mmol), isonicotinaldehyde (32 mg, 0.30 mmol) and 1-methylpiperazine (30 mg, 0.30 mmol) in EtOH (1.5 mL) was heated at 110° C. for 3 hours. The reaction mixture was cooled to room temperature and the solvent was removed. The residue was purified by column chromatography to afford the pure product (18 mg, 32% yield) as off white solid. $^1$H NMR (CDCl$_3$, 300 MHz) δ: 8.60 (d, J=5.7 Hz, 2H), 8.00 (d, J=2.1 Hz, 1H), 7.82 (d, J=8.4 Hz, 1H), 7.47 (d, J=6.0 Hz, 2H), 7.40 (dd, J=2.1, 8.7 Hz, 1H), 7.18-7.10 (m, 1H), 6.94-6.88 (m, 1H), 6.52 (d, J=9.3 Hz, 1H), 6.19 (d, J=9.6 Hz, 1H), 5.50 (s, 2H), 2.70-2.40 (m, 8H), 2.30 (s, 3H).

Example 38

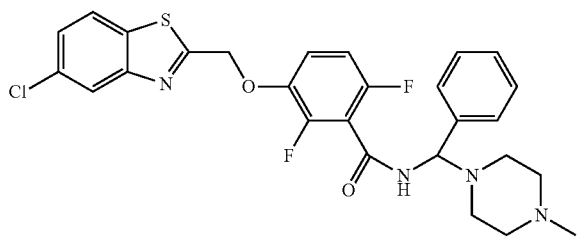 [SMILES: CN1CCN(C(NC(=O)c2c(F)ccc(OCc3nc4cc(Cl)ccc4s3)c2F)c2ccccc2)CC1]

In a sealed tube, mixture of benzamide 3a (35 mg, 0.10 mmol), benzaldehyde (32 mg, 0.30 mmol) and 1-methylpiperazine (30 mg, 0.30 mmol) in EtOH (1.5 mL) was heated at 110° C. for 3 hours. The reaction mixture was cooled to room temperature and the solvent was removed. The residue was purified by column chromatography to afford the pure product (29 mg, 54% yield) as off white solid. $^1$H NMR (CDCl$_3$, 300 MHz) δ: 8.01 (d, J=2.1 Hz, 1H), 7.82 (d, J=8.7 Hz, 1H), 7.52 (d, J=7.8 Hz, 2H), 7.42-7.30 (m, 4H), 7.16-7.08 (m, 1H), 6.92-6.85 (m, 1H), 6.33 (d, J=9.6 Hz, 1H), 6.12 (d, J=9.3 Hz, 1H), 5.52 (s, 2H), 2.75-2.42 (m, 8H), 2.29 (s, 3H).

Example 39

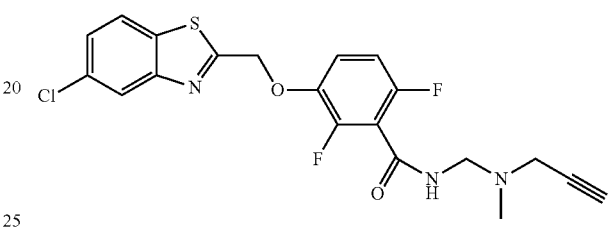

A 25-mL round bottom flask equipped with a magnetic stirrer under nitrogen was charged with the chloride 39b (25 mg, 0.06 mmol), CH$_2$Cl$_2$ (5 mL). After cooling to −30° C., triethylamine (42 ml, 0.3 mmol) was added to the reaction mixture, followed by adding N-methylprop-2-yn-1-amine (21 mg, 0.3 mmol). The reaction mixture was warmed to room temperature and stirred for 1 hour. The solvent was removed and the residue was purified by column chromatography to afford the pure product (6 mg, 23% yield) as white solid. $^1$H NMR (CDCl$_3$, 300 MHz) δ: 8.00 (d, J=2.1 Hz, 1H), 7.82 (d, J=8.4 Hz, 1H), 7.40 (dd, J=2.1, 8.7 Hz, 1H), 7.15-7.06 (m, 1H), 6.90-6.82 (m, 1H), 6.50 (bs, 1H), 5.50 (s, 2H), 4.45 (d, J=6.3 Hz, 2H), 3.48 (s, 2H), 2.50 (s, 3H), 2.31 (s, 1H).

The requisite intermediates were prepared as follows a. Preparation of Compound

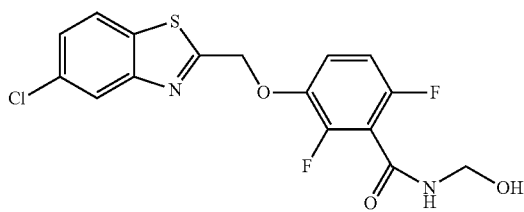 [SMILES: O=C(NCO)c1c(F)ccc(OCc2nc3cc(Cl)ccc3s2)c1F]

In a sealed tube, mixture of benzamide 3a (200 mg, 0.56 mmol), formaldehyde (37%, 1.5 mL, 0.5 mmol) and 5% K$_2$CO$_3$ in water (3 mL) in THF (1.5 mL) was heated at 65° C. for 12 hours. After cooling to room temperature, water was added to the reaction mixture. The solid was collected by filtration and washed with water. After drying, there was obtained the desired product (208 mg, 96% yield) as off white solid. $^1$H NMR (DMSO, 300 MHz) δ: 9.35 (t, J=2.1 Hz, 1H), 8.20 (d, J=8.7 Hz, 1H), 8.14 (d, J=1.5 Hz, 1H), 7.55 (dd, J=1.8, 8.7 Hz, 1H), 7.46-7.38 (m, 1H), 7.17-7.10 (m, 1H), 5.98 (t, J=6.9 Hz, 1H), 5.72 (s, 2H), 4.66 (t, J=6.6 Hz, 2H).

b. Preparation of Compound

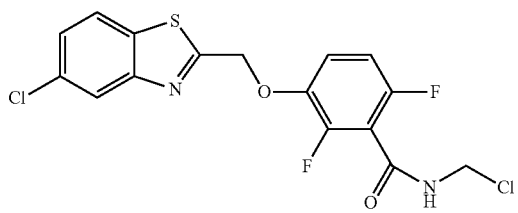 [SMILES: O=C(NCCl)c1c(F)ccc(OCc2nc3cc(Cl)ccc3s2)c1F]

A 50-mL round bottom flask equipped with a magnetic stirrer under nitrogen was charged with 39a (150 mg, 0.39 mmol), CH$_2$Cl$_2$ (10 mL). Thionyl chloride (0.28 mL, 3.9 mmol) was added via a syringe over 5 minutes. The resulting reaction mixture was stirred at room temperature for 1 hour. The solvent was removed to afford the desired product (170 mg). The crude product was used in next step without further purification. $^1$H NMR (DMSO, 300 MHz) δ: 10.09 (t, J=7.2 Hz, 1H), 8.22 (d, J=8.7 Hz, 1H), 8.14 (d, J=1.5 Hz, 1H), 7.55 (dd, J=2.1, 8.7 Hz, 1H), 7.54-7.46 (m, 1H), 7.23-7.17 (m, 1H), 5.74 (s, 2H), 5.33 (d, J=7.2 Hz, 2H).

Example 40

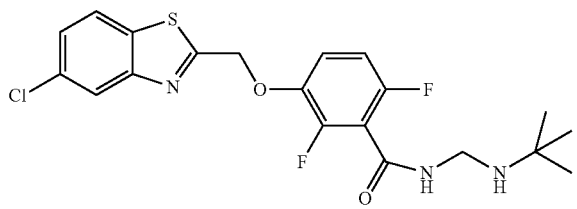 [SMILES: CC(C)(C)NCNC(=O)c1c(F)ccc(OCc2nc3cc(Cl)ccc3s2)c1F]

A 25-mL round bottom flask equipped with a magnetic stirrer under nitrogen was charged with the chloride 39b (25 mg, 0.06 mmol), CH$_2$Cl$_2$ (5 mL). After cooling to −30° C., triethylamine (42 ml, 0.3 mmol) was added to the reaction mixture, followed by adding 2-methylpropan-2-amine (22 mg, 0.3 mmol). The reaction mixture was warmed to room temperature and stirred for 1 hour. The solvent was removed and the residue was purified by column chromatography to afford the pure product (9 mg, 33% yield) as light yellow solid. $^1$H NMR (CDCl$_3$, 300 MHz) δ: 8.00 (d, J=2.1 Hz, 1H), 7.82 (d, J=8.4 Hz, 1H), 7.39 (dd, J=2.1, 8.7 Hz, 1H), 7.13-7.06 (m, 1H), 6.93 (bs, 1H), 6.87-6.80 (m, 1H), 5.48 (s, 2H), 4.56 (d, J=5.4 Hz, 2H), 1.27 (s, 9H).

Example 41

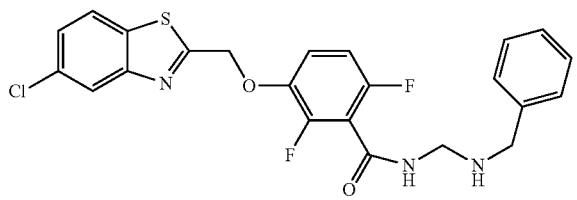 [SMILES: O=C(NCNCc1ccccc1)c1c(F)ccc(OCc2nc3cc(Cl)ccc3s2)c1F]

A 25-mL round bottom flask equipped with a magnetic stirrer under nitrogen was charged with the chloride 39b (25 mg, 0.06 mmol), CH$_2$Cl$_2$ (5 mL). After cooling to −30° C., triethylamine (42 ml, 0.3 mmol) was added to the reaction mixture, followed by adding phenylmethanamine (32 mg, 0.3 mmol). The reaction mixture was warmed to room temperature and stirred for 1 hour. The solvent was removed and the residue was purified by column chromatography to afford the pure product (9 mg, 28% yield) as light yellow. $^1$H NMR (CDCl$_3$, 300 MHz) δ: 8.00 (d, J=2.1 Hz, 1H), 7.82 (d, J=8.7 Hz, 1H), 7.40 (dd, J=2.1, 8.7 Hz, 1H), 7.37-7.21 (m, 5H), 7.15-7.08 (m, 1H), 6.90-6.84 (m, 1H), 6.36 (bs, 1H), 5.50 (s, 2H), 4.41 (d, J=5.7 Hz, 2H), 3.89 (s, 2H).

Example 42

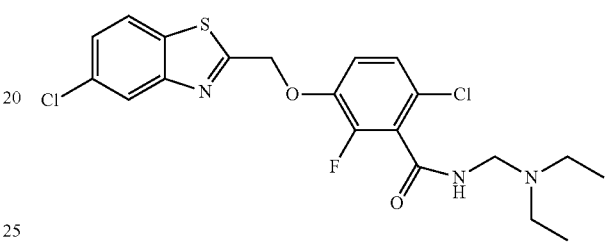

In a sealed tube, mixture of benzamide 42a (37 mg, 0.10 mmol), formaldehyde (37%, 0.041 mL, 0.50 mmol) and diethylamine (37 mg, 0.75 mmol) in H$_2$O:THF (1 mL: 0.5 mL) was heated at 65° C. for 2 hours. After cooling to room temperature, the reaction mixture was diluted with ethyl acetate, washed with brine, dried over Na$_2$SO$_4$, and concentrated, and purified by column chromatography to afford the pure product (29 mg, 61% yield) as white solid. $^1$H NMR (CDCl$_3$, 300 MHz) δ: 8.01 (d, J=1.5 Hz, 1H), 7.82 (d, J=8.4 Hz, 1H), 7.40 (dd, J=2.1, 8.7 Hz, 1H), 7.13-7.01 (m, 2H), 6.00 (bs, 1H), 4.48 (d, J=6.0 Hz, 2H), 2.65 (q, J=7.2 Hz, 4H), 1.13 (t, J=7.2 Hz, 6H).

The requisite intermediate was prepared as follows a. Preparation of Compound

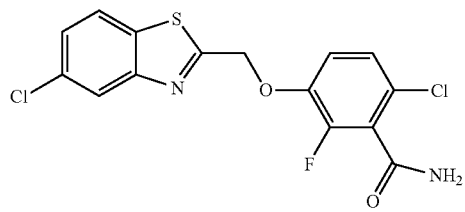 [SMILES: NC(=O)c1c(Cl)ccc(OCc2nc3cc(Cl)ccc3s2)c1F]

A 25-mL round bottom flask equipped with a magnetic stirrer was charged with 2-(bromomethyl)-5-chlorobenzo[d]thiazole (100 mg, 0.38 mmol), DMF (1 mL), K$_2$CO$_3$ (97 mg, 0.70 mmol), and 6-chloro-2-fluoro-3-hydroxybenzamide (66 mg, 0.35 mmol). The reaction mixture was stirred at room temperature for 12 hours then water was added. The solid was collected by filtration and washed with water. After air drying, the solid was triturated with CH$_2$Cl$_2$. There was obtained the desired product (93 mg) as brown solid with 72% yield. $^1$H NMR (DMSO, 300 MHz) δ: 8.21-8.14 (m, 3H), 7.90 (s, 1H), 7.55 (dd, J=2.1, 8.7 Hz, 1H), 7.41-7.30 (m, 2H), 5.76 (s, 2H).

Example 43

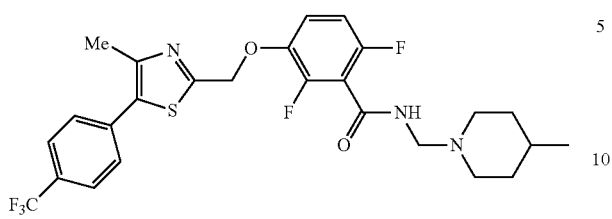

In a sealed tube, mixture of benzamide 43c (28 mg, 0.065 mmol), formaldehyde (37%) (0.03 mL, 0.65 mmol) and amine (0.08 mL, 0.65 mmol) in H$_2$O:THF (2:1) was heated at 65° C. for 2 hours. After cooling to room temperature, the reaction mixture was diluted with ethyl acetate, washed with brine, dried over Na$_2$SO$_4$, and concentrated to afford a brown solid, which was purified by column chromatography to furnish 8 mg of the pure product. Yield (minus recovered SM): 73%. $^1$H NMR (CD$_3$OD, 400 MHz) δ: 7.68-7.58 (m, 4H), 7.25-7.22 (m, 1H), 6.91-6.89 (m, 1H), 5.34 (s, 2H), 4.17 (s, 2H), 2.78-2.75 (m, 2H), 2.40 (s, 3H), 2.30-2.25 (m, 2H), 1.59-1.56 (m, 2H), 1.25-1.22 (m, 1H), 1.18-1.10 (m, 2H), 0.83 (d, J=6.3 Hz, 3H).

The requisite intermediates were prepared as follows:

a. Preparation of Compound

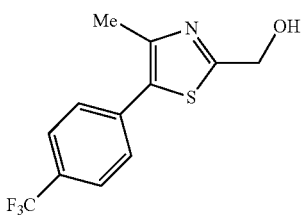 [SMILES: Cc1nc(CO)sc1-c1ccc(C(F)(F)F)cc1]

A 25-mL round bottom flask equipped with a magnetic stirrer, a condenser and a nitrogen in/outlet adapter was charged with bromo compound (100 mg, 0.48 mmol), 4-trifluoromethylphenylboronic acid (110 mg, 0.58 mmol), water/dioxane (2 mL/4 ml), K$_2$CO$_3$ (199 mg, 1.44 mmol). The resulting solution was degassed for 5 minutes, then Pd(OAc)$_2$ (11 mg, 0.05 mmol) and XPhos (46 mg, 0.09 mmol) was added. The reaction mixture was warmed to 100° C. and stirred overnight. After cooled to room temperature, the reaction mixture was diluted with EtOAc (75 mL) and washed with saturated NaHCO$_3$ (25 mL), dried over Na$_2$SO$_4$. The organic layer was concentrated under reduced pressure and purified on an ISCO using a maximum gradient of 70% EtOAc/hexane to give the title compound (60 mg, 46% yield). $^1$H NMR (CD$_3$OD, 400 MHz) δ: 7.77-7.66 (m, 4H), 4.84 (s, 2H), 2.47 (s, 3H).

b. Preparation of Compound

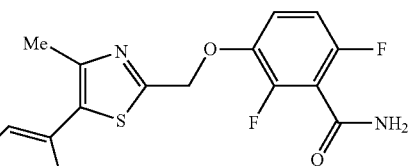

A 25-mL round bottom flask equipped with a magnetic stirrer under nitrogen was charged with alcohol 43a (60 mg, 0.22 mmol), CH$_2$Cl$_2$ (2.5 mL), and triethylamine (0.08 mL, 0.55 mmol). Methanesulfonyl chloride (0.034 mL, 0.44 mmol) was added via a syringe over 5 minutes. The resulting reaction mixture was stirred at room temperature overnight. The reaction mixture was diluted with CH$_2$Cl$_2$ (30 mL) and washed with saturated NaHCO$_3$ (15 ml), dried over Na$_2$SO$_4$, and concentrated under reduced pressure and purified on an ISCO using a maximum gradient of 30% EtOAc/hexane affording title compound (47 mg, 73% yield). $^1$H NMR (CD$_3$OD, 400 MHz) δ: 7.80-7.69 (m, 4H), 4.94 (s, 2H), 2.50 (s, 3H).

c. Preparation of Compound

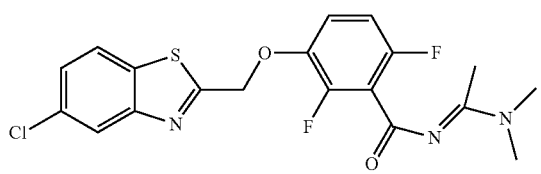

A 25-mL round bottom flask equipped with a magnetic stirrer, a condenser and a nitrogen in/outlet adapter was charged with chloro intermediate 43b (45 mg, 0.15 mmol), DMF (2 mL), K$_2$CO$_3$ (30 mg, 0.22 mmol), and phenol (25 mg, 0.15 mmol). The reaction mixture was stirred at room temperature overnight. The reaction mixture was diluted water (30 mL) and precipitate was filtered off and washed with additional water (3 mL) then dissolved in DCM and concentrated. Purification on an ISCO using a max gradient of 2% MeOH/DCM gave the title compound (51 mg, 79% yield). $^1$H NMR (CD$_3$OD, 400 MHz) δ: 7.80-7.69 (m, 4H), 7.38-7.32 (m, 1H), 7.03-6.99 (m, 1H), 5.44 (s, 2H), 2.51 (s, 3H).

Example 44

In a sealed vial, a suspension of substituted benzamide 3a (100 mg, 0.31 mmol) in 1.5 mL of dimethylacetamide dimethyl acetal was stirred at 120° C. for 30 minutes. The excess dimethylacetamide dimethyl acetal was removed under reduced pressure and the resulting solid was triturated with diethyl ether to afford the pure product (50 mg, 38% yield). $^1$H NMR (CDCl$_3$, 300 MHz) δ: 8.00 (d, J=2.4 Hz, 1H), 7.81 (d, J=8.7 Hz, 1H), 7.40 (dd, J=1.8, 8.4 Hz, 1H), 7.02-6.94 (m, 1H), 6.82-6.75 (m, 1H), 5.48 (s, 2H), 3.16 (s, 3H), 3.14 (s, 3H), 2.43 (s, 3H).

Example 45

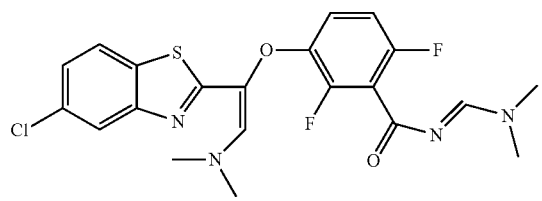 [SMILES: CN(C)/C=N/C(=O)c1c(F)ccc(O/C(=C/N(C)C)c2nc3cc(Cl)ccc3s2)c1F]

In a sealed vial, a suspension of substituted benzamide 3a (100 mg, 0.28 mmol) in 1.5 mL of dimethylformamide dimethyl acetal was stirred at 140° C. for 2 h. The excess dimethylformamide dimethyl acetal was removed under reduced pressure and the residue was purified by column chromatography to afford the pure product (42 mg, 32% in yield) as light brown oil. $^1$H NMR (CDCl$_3$, 300 MHz) δ: 8.64 (s, 1H), 7.69 (d, J=2.1 Hz, 1H), 7.55 (d, J=8.7 Hz, 1H), 7.37 (s, 1H), 7.10 (dd, J=2.4, 8.7 Hz, 1H), 7.05-6.97 (m, 1H), 6.77-6.70 (m, 1H), 3.22 (s, 3H), 3.18 (s, 3H), 3.03 (s, 6H).

Example 46

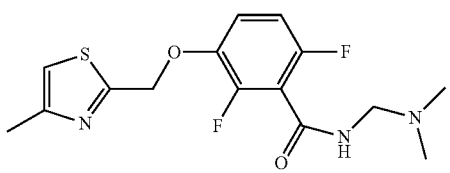

In a sealed tube, mixture of 46b (30 mg, 0.11 mmol), formaldehyde (37%, 0.044 mL, 0.55 mmol) and dimethylamine (0.27 ml, 0.55 mmol) in H$_2$O:THF (1 mL:0.5 mL) was heated at 65° C. for 2 hours. After cooling to room temperature, the reaction mixture was diluted with ethyl acetate, washed with brine, dried over Na$_2$SO$_4$, and concentrated to afford a brown solid, which was purified by column chromatography to furnish the pure product (20 mg) as white solid with 55% yield. $^1$H NMR (CDCl$_3$, 300 MHz) δ: 7.11-7.03 (m, 1H), 6.91 (s, 1H), 6.87-6.82 (m, 1H), 6.61 (bs, 1H), 5.34 (s, 2H), 4.24 (d, J=6.0 Hz, 2H), 2.45 (s, 3H), 2.30 (s, 6H).

The requisite intermediates were prepared as follows

Preparation of Compound

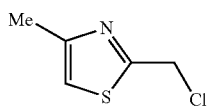

a. A 25-mL round bottom flask equipped with a magnetic stirrer under nitrogen was charged with alcohol 21a (210 mg, 1.67 mmol), CH$_2$Cl$_2$ (4 mL), and triethylamine (0.45 mL, 3.25 mmol). Methanesulfonyl chloride (0.25 mL, 3.2 mmol) was added via a syringe over 5 minutes. The resulting reaction mixture was stirred at room temperature overnight. The reaction mixture was diluted with CH$_2$Cl$_2$ (30 mL) and washed with saturated NaHCO$_3$ (15 ml), dried over Na$_2$SO$_4$, and concentrated under reduced pressure and purified on an ISCO using a maximum gradient of 5% MeOH/DCM affording desired compound (180 mg, 73% yield). $^1$H NMR (CDCl$_3$, 300 MHz) δ: 6.94 (s, 1H), 4.84 (s, 2H), 2.47 (s, 3H).

Preparation of Compound

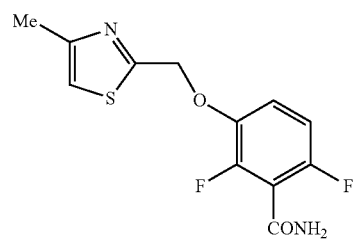 [SMILES: Cc1csc(COc2ccc(F)c(C(N)=O)c2F)n1]

b. A 25-mL round bottom flask equipped with a magnetic stirrer was charged with chloro compound 46a (160 mg, 1.1 mmol), DMF (2.0 mL), K$_2$CO$_3$ (400 mg, 3.0 mmol), and 2,6-difluoro-3-hydroxybenzamide (250 mg, 1.5 mmol). The reaction mixture was stirred at room temperature for 12 hours then water was added. The solid was collected by filtration and washed with water. After air drying, the solid was triturated with CH$_2$Cl$_2$. There was obtained the desired product (202 mg, 65% yield) as white solid. $^1$H NMR (CDCl$_3$, 300 MHz) δ: 7.18-7.11 (m, 1H), 6.97 (s, 1H), 6.94-6.87 (m, 1H), 5.4 (s, 2H), 2.44 (s, 3H).

Example 47

The following can illustrate representative pharmaceutical dosage forms, containing a compound of formula I ('Compound X') or a pharmaceutically acceptable salt thereof, for therapeutic or prophylactic use in humans. The tablets can optionally comprise an enteric coating.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
| --- | --- |
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| | mg/ml |
| --- | --- |
| (iv) Injection 1 (1 mg/mL) | |
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |
| (v) Injection 2 (10 mg/ml) | |
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

| (vi) Aerosol | mg/can |
| --- | --- |
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula (I):

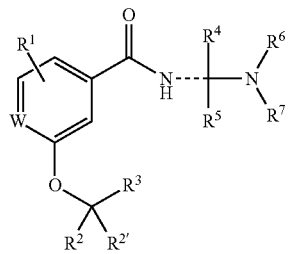

wherein:
$R^1$ is 1, 2 or 3 substituents independently selected from $(C_1$-$C_6)$alkyl, $(C_2$-$C_6)$alkenyl, $(C_2$-$C_6)$alkynyl, $(C_1$-$C_6)$alkoxy, hydroxyl, hydroxy$(C_1$-$C_6)$alkyl, mercapto, mercapto$(C_1$-$C_6)$alkyl, $(C_1$-$C_6)$alkylthio, halo, fully or partially fluorinated $(C_1$-$C_3)$alkyl, fully or partially fluorinated $(C_1$-$C_3)$alkoxy, fully or partially fluorinated $(C_1$-$C_3)$alkylthio, nitro, cyano, oxo, phenyl, phenoxy, monocyclic heteroaryl or heteroaryloxy with 5 or 6 ring atoms, —COOR$^A$—, —COR$^A$—, —OCOR$^A$—, —SO$_2$R$^A$—, —CONR$^A$R$^B$—, —SO$_2$NR$^A$NR$^B$—OCONR$^A$R$^B$—, —NR$^B$COR$^A$—, —NR$^B$COOR$^A$—, —NR$^B$—SO$_2$OR$^A$—, or —NR$^A$CONR$^A$R$^B$—, wherein $R^A$ and $R^B$ are independently hydrogen or an $(C_1$-$C_6)$ alkyl group or, in the case where $R^A$ and $R^B$ are linked to the same N atom, $R^A$ and $R^B$ taken together with that nitrogen may form a cyclic amino ring; where the substituent is phenyl, phenoxy or monocyclic heteroaryl or heteroaryloxy with 5 or 6 ring atoms, the phenyl or heteroaryl ring thereof may itself be substituted by any of the above substituents except phenyl phenoxy, heteroaryl or heteroaryloxy;

W is CR$^a$, or N;

R$^a$ is absent, hydrogen, or an optional substituent, $R^2$ is hydrogen, methyl, or fluoro, and $R^{2'}$ is hydrogen, $(C_1$-$C_6)$alkyl, $(C_2$-$C_6)$alkenyl, $(C_2$-$C_6)$alkynyl, $(C_3$-$C_8)$cycloalkyl, aryl, or 5-6 membered heterocyclyl, wherein each alkyl, alkenyl, alkynyl, cycloalkyl, aryl, or heterocyclyl may be optionally substituted with one or more R$^b$;

or R$^a$ and $R^2$ taken together are —CH$_2$—, —CH$_2$—CH$_2$—, —O—, —O—CH$_2$—, —CH$_2$O—, —O—CH$_2$—CH$_2$—, or —CH$_2$—CH$_2$—O—;

or R$^a$ is absent, hydrogen or an optional substituent, and $R^{2'}$ taken together with $R^2$ is cyclopropyl, cyclobutyl, azetidine, or =CH—N(R$^c$)$_2$; wherein the cyclopropyl, cyclobutyl, and azetidine can optionally be substituted with $(C_1$-$C_6)$alkyl;

$R^3$ is (Alk$^1$)$_m$—(Z)$_p$-(Alk$^2$)$_n$-Q;

Z is —O—, —S—, —S(O)—, —SO$_2$—, —NH—, —N(CH$_3$)—, —N(CH$_2$CH$_3$)—, —C(=O)—, —OC(=O)—, —C(=O)O—, or an optionally substituted divalent monocyclic carbocycle or heterocyclic radical having 3 to 6 ring atoms, or an optionally substituted divalent bicyclic heterocyclic radical having 5 to 10 ring atoms;

Alk$^1$ is optionally substituted, $(C_2$-$C_6)$alkenylene, or $(C_2$-$C_6)$alkynylene radical, which may optionally terminate with or be interrupted by —O—, —S—, —S(O)—, —SO$_2$—, —NH—, —N(CH$_3$)—, —N(CH$_2$CH$_3$)—;

Alk$^2$ is optionally substituted, $(C_2$-$C_6)$alkenylene, or $(C_2$-$C_6)$alkynylene radical, which may optionally terminate with or be interrupted by —O—, —S—, —S(O)—, —SO$_2$—, —NH—, —N(CH$_3$)—, —N(CH$_2$CH$_3$)—;

Q is hydrogen, halo, cyano, or hydroxyl, or an optionally substituted monocyclic carbocyclic or heterocyclic radical having 3 to 7 ring atoms, or an optionally substituted bicyclic heterocyclic radical having 5 to 10 ring atoms;

the bond represented by ---- is a double bond, R$^4$ is hydrogen or methyl, and R$^5$ and the hydrogen attached to the nitrogen are absent; or the bond represented by ---- is a single bond, R$^4$ is H, optionally substituted monocyclic carbocycle, or heterocyclic radical having 3 to 6 ring atoms, and R$^5$ is hydrogen; wherein each optionally substituted monocyclic carbocycle, or heterocyclic radical having 3 to 6 ring atoms of R$^4$ is optionally substituted with one or more substituents independently selected from $(C_1$-$C_6)$alkoxy, halo, hydroxy, cyano, nitro, amino, methylamino, dimethylamino, carboxy, $(C_1$-$C_6)$alkoxycarbonyl, aminocarbonyl, $(C_1$-$C_6)$alkanoylamino, or tetrazole;

R$^6$ and R$^7$ are each independently hydrogen, $(C_1$-$C_6)$alkyl, $(C_2$-$C_6)$alkenyl, $(C_2$-$C_6)$alkynyl, or a heterocyclic radical having 3 to 6 ring atoms, or R$^6$ and R$^7$ together with the nitrogen to which they are attached form a 5 or 6 membered heterocyclic ring, which ring is optionally substituted with one or more groups independently selected from $(C_1-C_6)$alkyl; wherein any $(C_1-C_6)$alkyl of $R^6$ and $R^7$ is optionally substituted with one or more substituents independently selected from $(C_1-C_6)$alkoxy, halo, hydroxy, cyano, nitro, amino, methylamino, dimethylamino, oxo (=O), carboxy, $(C_1-C_6)$alkoxycarbonyl, aminocarbonyl, $(C_1-C_6)$alkanoylamino, aryl, or tetrazole; and wherein any aryl or heterocyclic radical having 3 to 6 ring atoms of $R^6$ and $R^7$ is optionally substituted with one or more substituents independently selected from $(C_1-C_6)$alkyl, $(C_1-C_6)$alkoxy, halo, trifluoromethyl, trifluoromethoxy, hydroxy, cyano, nitro, tetrazole, carboxy, $(C_1-C_6)$alkoxycarbonyl, or a $(C_1-C_4)$alkyl that is optionally substituted with one or more substituents independently selected from $(C_1-C_6)$alkoxy, halo, hydroxy, cyano, nitro, tetrazole, carboxy, $(C_1-C_6)$alkoxycarbonyl, amino, methylamino, dimethylamino, or oxo (=O);

each $R^b$ is independently $R^f$, $OR^e$, —C(=O)$R^e$, —OC(=O)$R^e$, —C(=O)O$R^e$, —N($R^e$)$_2$, —N$R^e$C(=O)$R^d$, —C(=O)N($R^e$)$_2$, —OC(=O)N($R^e$)$_2$, —C(=O)N($R^e$)—N($R^e$)C(=O)$R^d$, —NHC(=O)NH$R^d$, —NHS(O)$_{0-2}R^d$, —S(O)$_{0-2}R^d$, —OS(O)$_{0-2}R^d$, —OP(=O)(O$R^e$)$_2$, or —P(=O)(O$R^e$)$_2$;

each $R^e$ is independently H or $(C_1-C_6)$alkyl;

each $R^d$ is optionally substituted and is independently selected from $(C_1-C_6)$alkyl, $(C_2-C_6)$alkenyl, $(C_2-C_6)$alkynyl, aryl, aryl$(C_1-C_6)$alkyl, 4-10 membered heterocyclyl and heterocyclyl$(C_1-C_6)$alkyl;

each $R^e$ is independently selected from H, $(C_1-C_6)$alkyl, $(C_2-C_6)$alkenyl, $(C_2-C_6)$alkynyl, aryl, aryl$(C_1-C_6)$alkyl, 4-10 membered heterocyclyl and heterocyclyl$(C_1-C_6)$alkyl, wherein each $(C_1-C_6)$alkyl, $(C_2-C_6)$alkenyl, $(C_2-C_6)$alkynyl, aryl, aryl$(C_1-C_6)$alkyl, 4-10 membered heterocyclyl and heterocyclyl$(C_1-C_6)$alkyl is optionally substituted;

each $R^f$ is optionally substituted and is independently selected from aryl and 4-10 membered heterocyclyl; and m, p, and n are each independently 0 or 1, provided that at least one of m, p, and n is 1; and optional substituents are independently selected from, $(C_1-C_6)$alkyl, $(C_2-C_6)$alkenyl, $(C_2-C_6)$alkynyl, $(C_1-C_6)$alkoxy, hydroxyl, hydroxy$(C_1-C_6)$alkyl, mercapto, mercapto$(C_1-C_6)$alkyl, $(C_1-C_6)$alkylthio, halo, fully or partially fluorinated $(C_1-C_3)$alkyl, fully or partially fluorinated $(C_1-C_3)$alkoxy, fully or partially fluorinated $(C_1-C_3)$alkylthio, nitro, cyano, oxo, phenyl, phenoxy, monocyclic heteroaryl or heteroaryloxy with 5 or 6 ring atoms, —COO$R^A$—, —CO$R^A$—, —OCO$R^A$— —SO$_2R^A$—, —CON$R^AR^B$—, —SO$_2$N$R^AR^B$—, —N$R^AR^B$—, —OCON$R^AR^B$—, —N$R^B$CO$R^A$—, —N$R^B$COO$R^A$—, —N$R^B$—SO$_2$O$R^A$—, or —N$R^A$-CON$R^AR^B$—, wherein $R^A$ and $R^B$ are independently hydrogen or a $(C_1-C_6)$alkyl group or, in the case where $R^A$ and $R^B$ are linked to the same N atom, $R^A$ and $R^B$ taken together with that nitrogen may form a cyclic amino ring; where the substituent is phenyl, phenoxy or monocyclic heteroaryl or heteroaryloxy with 5 or 6 ring atoms, the phenyl or heteroaryl ring thereof may itself be substituted by any of the above substituents except phenyl phenoxy, heteroaryl or heteroaryloxy;

or a salt thereof.

2. The compound of claim 1 which is a compound of formula (Ia):

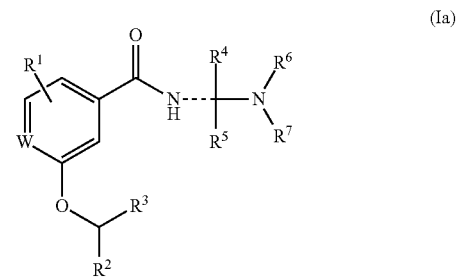

(Ia)

wherein:

$R^1$ is 1, 2 or 3 substituents independently selected from $(C_1-C_6)$alkyl, $(C_2-C_6)$alkenyl, $(C_2-C_6)$alkynyl, $(C_1-C_6)$alkoxy, hydroxyl, hydroxy$(C_1-C_6)$alkyl, mercapto, mercapto$(C_1-C_6)$alkyl, $(C_1-C_6)$alkylthio, halo, fully or partially fluorinated $(C_1-C_3)$alkyl, fully or partially fluorinated $(C_1-C_3)$alkoxy, fully or partially fluorinated $(C_1-C_3)$alkylthio, nitro, cyano, oxo, phenyl, phenoxy, monocyclic heteroaryl or heteroaryloxy with 5 or 6 ring atoms, —COO$R^A$—, —CO$R^A$—, —OCO$R^A$—, —SO$_2R^A$—, —CON$R^AR^B$—, —SO$_2$N$R^AR^B$—, —N$R^AR^B$—, —OCON$R^AR^B$—, —N$R^B$CO$R^A$—, —N$R^B$COO$R^A$—, —N$R^B$—SO$_2$O$R^A$—, or —N$R^A$-CON$R^AR^B$—, wherein $R^A$ and $R^B$ are independently hydrogen or an $(C_1-C_6)$alkyl group or, in the case where $R^A$ and $R^B$ are linked to the same N atom, $R^A$ and $R^B$ taken together with that nitrogen may form a cyclic amino ring; where the substituent is phenyl, phenoxy or monocyclic heteroaryl or heteroaryloxy with 5 or 6 ring atoms, the phenyl or heteroaryl ring thereof may itself be substituted by any of the above substituents except phenyl phenoxy, heteroaryl or heteroaryloxy;

W is $CR^a$, or N;

$R^a$ is absent, hydrogen, or an optional substituent, and $R^2$ is hydrogen, methyl, or fluoro; or $R^a$ and $R^2$ taken together are —CH$_2$—, —CH$_2$—CH$_2$—, —O—, —O—CH$_2$—, —CH$_2$O—, —O—CH$_2$—CH$_2$—, or —CH$_2$—CH$_2$—O—;

$R^3$ is -(Alk$^1$)$_m$—(Z)$_p$-(Alk$^2$)$_n$-Q;

Z is —O—, —S—, —S(O)—, —SO$_2$—, —NH—, —N(CH$_3$)—, —N(CH$_2$CH$_3$)—, —C(=O)—, —OC(=O)—, —C(=O)O—, or an optionally substituted divalent monocyclic carbocycle or heterocyclic radical having 3 to 6 ring atoms, or an optionally substituted divalent bicyclic heterocyclic radical having 5 to 10 ring atoms;

Alk$^1$ is optionally substituted, $(C_2-C_6)$alkenylene, or $(C_2-C_6)$alkynylene radical, which may optionally terminate with or be interrupted by —O—, —S—, —S(O)—, —SO$_2$—, —NH—, —N(CH$_3$)—, —N(CH$_2$CH$_3$)—;

Alk$^2$ is optionally substituted, $(C_2-C_6)$alkenylene, or $(C_2-C_6)$alkynylene radical, which may optionally terminate with or be interrupted by —O—, —S—, —S(O)—, —SO$_2$—, —NH—, —N(CH$_3$)—, —N(CH$_2$CH$_3$)—;

Q is hydrogen, halo, cyano, or hydroxyl, or an optionally substituted monocyclic carbocyclic or heterocyclic radical having 3 to 7 ring atoms, or an optionally substituted bicyclic heterocyclic radical having 5 to 10 ring atoms;

the bond represented by ---- is a double bond, $R^4$ is hydrogen, $R^5$ and the hydrogen attached to the nitrogen are absent; or the bond represented by ---- is a single bond and $R^4$ and $R^5$ are each hydrogen;

$R^6$ and $R^7$ are each independently hydrogen, $(C_1-C_6)$alkyl, or benzyl, or $R^6$ and $R^7$ together with the nitrogen to which they are attached form a aziridino, azetidino, morpholino, thiomorpholino, piperazino, pyrrolidino or piperidino ring, which ring is optionally substituted with one or more groups independently selected from $(C_1-C_6)$alkyl; wherein any $(C_1-C_6)$alkyl of $R^6$ and $R^7$ is optionally substituted with one or more substituents independently selected from $(C_1-C_6)$alkoxy, halo, hydroxy, cyano, nitro, amino, methylamino, dimethylamino, oxo (=O), carboxy, $(C_1-C_6)$alkoxycarbonyl, aminocarbonyl, $(C_1-C_6)$alkanoylamino, or tetrazole; and wherein any benzyl of $R^6$ and $R^7$ is optionally substituted with one or more substituents independently selected from $(C_1-C_6)$alkyl, $(C_1-C_6)$alkoxy, halo, trifluoromethyl, trifluoromethoxy, hydroxy, cyano, nitro, tetrazole, carboxy, $(C_1-C_6)$alkoxycarbonyl, or a $(C_1-C_4)$alkyl that is optionally substituted with one or more substituents independently selected from $(C_1-C_6)$alkoxy, halo, hydroxy, cyano, nitro, tetrazole, carboxy, $(C_1-C_6)$alkoxycarbonyl, amino, methylamino, dimethylamino, or oxo (=O); and m, p, and n are each independently 0 or 1, provided that at least one of m, p, and n is 1; and optional substituents are independently selected from, $(C_1-C_6)$alkyl, $(C_2-C_6)$alkenyl, $(C_2-C_6)$alkynyl, $(C_1-C_6)$alkoxy, hydroxyl, hydroxy$(C_1-C_6)$alkyl, mercapto, mercapto$(C_1-C_6)$alkyl, $(C_1-C_6)$alkylthio, halo, fully or partially fluorinated $(C_1-C_3)$alkyl, fully or partially fluorinated $(C_1-C_3)$alkoxy, fully or partially fluorinated $(C_1-C_3)$alkylthio, nitro, cyano, oxo, phenyl, phenoxy, monocyclic heteroaryl or heteroaryloxy with 5 or 6 ring atoms, $-COOR^A-$, $-COR^A-$, $-OCOR^A-$, $-SO_2R^A-$, $-CONR^AR^B-$, $-SO_2NR^AR^B-$, $-NR^AR^B-$, $-OCONR^AR^B-$, $-NR^BCOR^A-$, $-NR^BCOOR^A-$, $-NR^B-SO_2OR^A-$, or $-NR^A-CONR^AR^B-$, wherein $R^A$ and $R^B$ are independently hydrogen or a $(C_1-C_6)$alkyl group or, in the case where $R^A$ and $R^B$ are linked to the same N atom, $R^A$ and $R^B$ taken together with that nitrogen may form a cyclic amino ring; where the substituent is phenyl, phenoxy or monocyclic heteroaryl or heteroaryloxy with 5 or 6 ring atoms, the phenyl or heteroaryl ring thereof may itself be substituted by any of the above substituents except phenyl phenoxy, heteroaryl or heteroaryloxy;

or a salt thereof.

3. A compound of formula (Ib):

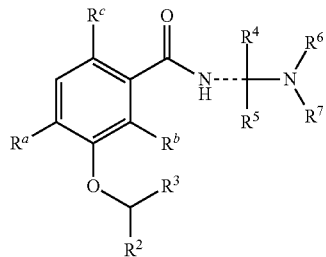

(Ib)

wherein:

$R^a$ is hydrogen, or an optional substituent, $R^2$ is hydrogen, methyl, or fluoro;

or $R^a$ and $R^2$ taken together are $-CH_2-$, $-CH_2-CH_2-$, $-O-$, $-O-CH_2-$, $-CH_2O-$, $-O-CH_2-CH_2-$, or $-CH_2-CH_2-O-$;

$R^3$ is $-(Alk^1)_m-(Z)_p-(Alk^2)_n-Q$;

Z is $-O-$, $-S-$, $-S(O)-$, $-SO_2-$, $-NH-$, $-N(CH_3)-$, $-N(CH_2CH_3)-$, $-C(=O)-$, $-OC(=O)-$, $-C(=O)O-$, or an optionally substituted divalent monocyclic carbocycle or heterocyclic radical having 3 to 6 ring atoms, or an optionally substituted divalent bicyclic heterocyclic radical having 5 to 10 ring atoms;

$Alk^1$ is optionally substituted $(C_1-C_6)$alkylene, $(C_2-C_6)$alkenylene, or $(C_1-C_6)$alkynylene radical, which may optionally terminate with or be interrupted by $-O-$, $-S-$, $-S(O)-$, $-SO_2-$, $-NH-$, $-N(CH_3)-$, $-N(CH_2CH_3)-$;

$Alk^2$ is optionally substituted $(C_1-C_6)$alkylene, $(C_2-C_6)$alkenylene, or $(C_1-C_6)$alkynylene radical, which may optionally terminate with or be interrupted by $-O-$, $-S-$, $-S(O)-$, $-SO_2-$, $-NH-$, $-N(CH_3)-$, $-N(CH_2CH_3)-$;

Q is hydrogen, halo, cyano, or hydroxyl, or an optionally substituted monocyclic carbocyclic or heterocyclic radical having 3 to 7 ring atoms, or an optionally substituted bicyclic heterocyclic radical having 5 to 10 ring atoms;

the bond represented by ---- is a double bond, $R^4$ is hydrogen or methyl, and $R^5$ and the hydrogen attached to the nitrogen are absent; or the bond represented by ---- is a single bond, $R^4$ is H, optionally substituted monocyclic carbocycle, or heterocyclic radical having 3 to 6 ring atoms, and $R^5$ is hydrogen; wherein each optionally substituted monocyclic carbocycle, or heterocyclic radical having 3 to 6 ring atoms of $R^4$ is optionally substituted with one or more substituents independently selected from $(C_1-C_6)$alkoxy, halo, hydroxy, cyano, nitro, amino, methylamino, dimethylamino, carboxy, $(C_1-C_6)$alkoxycarbonyl, aminocarbonyl, $(C_1-C_6)$alkanoylamino, or tetrazole;

$R^6$ and $R^7$ are each independently hydrogen, $(C_1-C_6)$alkyl, $(C_2-C_6)$alkenyl, $(C_2-C_6)$alkynyl, or a heterocyclic radical having 3 to 6 ring atoms, or $R^6$ and $R^7$ together with the nitrogen to which they are attached form a 5 or 6 membered heterocyclic ring, which ring is optionally substituted with one or more groups independently selected from $(C_1-C_6)$alkyl; wherein any $(C_1-C_6)$alkyl of $R^6$ and $R^7$ is optionally substituted with one or more substituents independently selected from $(C_1-C_6)$alkoxy, halo, hydroxy, cyano, nitro, amino, methylamino, dimethylamino, oxo (=O), carboxy, $(C_1-C_6)$alkoxycarbonyl, aminocarbonyl, $(C_1-C_6)$alkanoylamino, aryl, or tetrazole; and wherein any aryl or heterocyclic radical having 3 to 6 ring atoms of $R^6$ and $R^7$ is optionally substituted with one or more substituents independently selected from $(C_1-C_6)$alkyl, $(C_1-C_6)$alkoxy, halo, trifluoromethyl, trifluoromethoxy, hydroxy, cyano, nitro, tetrazole, carboxy, $(C_1-C_6)$alkoxycarbonyl, or a $(C_1-C_4)$alkyl that is optionally substituted with one or more substituents independently selected from $(C_1-C_6)$alkoxy, halo, hydroxy, cyano, nitro, tetrazole, carboxy, $(C_1-C_6)$alkoxycarbonyl, amino, methylamino, dimethylamino, or oxo (=O);

$R^{1b}$ and $R^{1c}$ are independently fluoro or chloro, or one of $R^{1b}$ and $R^{1c}$ is hydrogen while the other is fluoro or chloro; and m, p, and n are each independently 0 or 1, provided that at least one of m, p, and n is 1;

optional substituents are independently selected from, $(C_1-C_6)$alkyl, $(C_2-C_6)$alkenyl, $(C_2-C_6)$alkynyl, $(C_1-C_6)$alkoxy, hydroxyl, hydroxy$(C_1-C_6)$alkyl, mercapto, mercapto$(C_1-C_6)$alkyl, $(C_1-C_6)$alkylthio, halo, fully or partially fluorinated $(C_1-C_3)$alkyl, fully or partially fluorinated $(C_1-C_3)$alkoxy, fully or partially fluorinated $(C_1-C_3)$alkylthio, nitro, cyano, oxo, phenyl, phenoxy, monocyclic heteroaryl or heteroaryloxy with 5 or 6 ring atoms, —COOR$^A$—, —COR$^A$—, —OCOR$^A$— —SO$_2$R$^A$—, —CONR$^A$R$^B$—, —NR$^A$R$^B$—, —OCON-R$^A$R$^B$—, —NR$^B$COR$^A$—, —NR$^B$COOR$^A$—, —NR$^B$—SO$_2$OR$^A$—, or —NR$^A$CONR$^A$R$^B$—, wherein R$^A$ and R$^B$ are independently hydrogen or a $(C_1-C_6)$ alkyl group or, in the case where R$^A$ and R$^B$ are linked to the same N atom, R$^A$ and R$^B$ taken together with that nitrogen may form a cyclic amino ring; where the substituent is phenyl, phenoxy or monocyclic heteroaryl or heteroaryloxy with 5 or 6 ring atoms, the phenyl or heteroaryl ring thereof may itself be substituted by any of the above substituents except phenyl phenoxy, heteroaryl or heteroaryloxy;

or a salt thereof.

4. A compound of formula (Ic):

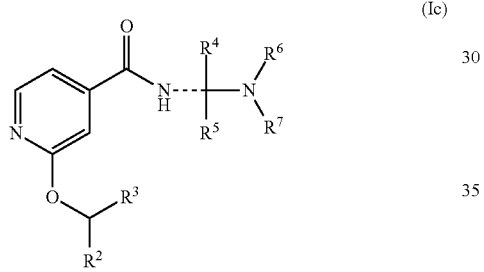

(Ic)

wherein

R$^2$ is hydrogen, methyl, or fluoro;

R$^3$ is -(Alk$^1$)$_m$—(Z)$_p$-(Alk$^2$)$_n$-Q;

Z is —O—, —S—, —S(O)—, —SO$_2$—, —NH—, —N(CH$_3$)—, —N(CH$_2$CH$_3$)—, —C(=O)—, —OC(=O)—, —C(=O)O—, or an optionally substituted divalent monocyclic carbocyclic or heterocyclic radical having 3 to 6 ring atoms, or an optionally substituted divalent bicyclic heterocyclic radical having 5 to 10 ring atoms;

Alk$^1$ is optionally substituted $(C_1-C_6)$alkylene, $(C_2-C_6)$ alkenylene, or $(C_1-C_6)$alkynylene radical, which may optionally terminate with or be interrupted by —O—, —S—, —S(O)—, —SO$_2$—, —NH—, —N(CH$_3$)—, —N(CH$_2$CH$_3$)—;

Alk$^2$ is optionally substituted $(C_1-C_6)$alkylene, $(C_2-C_6)$ alkenylene, or $(C_1-C_6)$alkynylene radical, which may optionally terminate with or be interrupted by —O—, —S—, —S(O)—, —SO$_2$—, —NH—, —N(CH$_3$)—, —N(CH$_2$CH$_3$)—;

Q is hydrogen, halo, cyano, or hydroxyl, or an optionally substituted monocyclic carbocyclic or heterocyclic radical having 3 to 7 ring atoms, or an optionally substituted bicyclic heterocyclic radical having 5 to 10 ring atoms;

the bond represented by ---- is a double bond, R$^4$ is hydrogen or methyl, and R$^5$ and the hydrogen attached to the nitrogen are absent; or the bond represented by ---- is a single bond, R$^4$ is H, optionally substituted monocyclic carbocycle, or heterocyclic radical having 3 to 6 ring atoms, and R$^5$ is hydrogen; wherein each optionally substituted monocyclic carbocycle, or heterocyclic radical having 3 to 6 ring atoms of R$^4$ is optionally substituted with one or more substituents independently selected from $(C_1-C_6)$alkoxy, halo, hydroxy, cyano, nitro, amino, methylamino, dimethylamino, carboxy, $(C_1-C_6)$alkoxycarbonyl, aminocarbonyl, $(C_1-C_6)$alkanoylamino, or tetrazole;

R$^6$ and R$^7$ are each independently hydrogen, $(C_1-C_6)$alkyl, $(C_2-C_6)$alkenyl, $(C_2-C_6)$alkynyl, or a heterocyclic radical having 3 to 6 ring atoms, or R$^6$ and R$^7$ together with the nitrogen to which they are attached form a 5 or 6 membered heterocyclic ring, which ring is optionally substituted with one or more groups independently selected from $(C_1-C_6)$alkyl; wherein any $(C_1-C_6)$alkyl of R$^6$ and R$^7$ is optionally substituted with one or more substituents independently selected from $(C_1-C_6)$ alkoxy, halo, hydroxy, cyano, nitro, amino, methylamino, dimethylamino, oxo (=O), carboxy, $(C_1-C_6)$ alkoxycarbonyl, aminocarbonyl, $(C_1-C_6)$ alkanoylamino, aryl, or tetrazole; and wherein any aryl or heterocyclic radical having 3 to 6 ring atoms of R$^6$ and R$^7$ is optionally substituted with one or more substituents independently selected from $(C_1-C_6)$alkyl, $(C_1-C_6)$alkoxy, halo, trifluoromethyl, trifluoromethoxy, hydroxy, cyano, nitro, tetrazole, carboxy, $(C_1-C_6)$ alkoxycarbonyl, or a $(C_1-C_4)$alkyl that is optionally substituted with one or more substituents independently selected from $(C_1-C_6)$alkoxy, halo, hydroxy, cyano, nitro, tetrazole, carboxy, $(C_1-C_6)$alkoxycarbonyl, amino, methylamino, dimethylamino, or oxo (=O); and m, p, and n are each independently 0 or 1, provided that at least one of m, p, and n is 1;

optional substituents are independently selected from, $(C_1-C_6)$alkyl, $(C_2-C_6)$alkenyl, $(C_2-C_6)$alkynyl, $(C_1-C_6)$ alkoxy, hydroxyl, hydroxy$(C_1-C_6)$alkyl, mercapto, mercapto$(C_1-C_6)$alkyl, $(C_1-C_6)$alkylthio, halo, fully or partially fluorinated $(C_1-C_3)$alkyl, fully or partially fluorinated $(C_1-C_3)$alkoxy, fully or partially fluorinated $(C_1-C_3)$alkylthio, nitro, cyano, oxo, phenyl, phenoxy, monocyclic heteroaryl or heteroaryloxy with 5 or 6 ring atoms, —COOR$^A$—, —COR$^A$—, —OCOR$^A$— —SO$_2$R$^A$—, —CONR$^A$R$^B$—, —SO$_2$NR$^A$R$^B$—, —NR$^A$R$^B$—, —OCONR$^A$R$^B$—, —NR$^B$COR$^A$—, —NR$^B$COOR$^A$—, —NR$^B$—SO$_2$OR$^A$—, or —NR$^A$-CONR$^A$R$^B$—, wherein R$^A$ and R$^B$ are independently hydrogen or a $(C_1-C_6)$alkyl group or, in the case where R$^A$ and R$^B$ are linked to the same N atom, R$^A$ and R$^B$ taken together with that nitrogen may form a cyclic amino ring; where the substituent is phenyl, phenoxy or monocyclic heteroaryl or heteroaryloxy with 5 or 6 ring atoms, the phenyl or heteroaryl ring thereof may itself be substituted by any of the above substituents except phenyl phenoxy, heteroaryl or heteroaryloxy;

or a salt thereof.

5. The compound of claim 1 wherein R$^a$ and R$^2$ are hydrogen.

6. The compound of claim 1 wherein R$^a$ is hydrogen or an optional substituent, R$^2$ is hydrogen, methyl, or fluoro, and R$^{2'}$ is $(C_1-C_6)$alkyl, $(C_2-C_6)$alkenyl, $(C_2-C_6)$alkynyl, $(C_3-C_8)$ cycloalkyl, aryl, or 5-6 membered heterocyclyl, wherein each alkyl, alkenyl, alkynyl, cycloalkyl, aryl, or heterocyclyl may be optionally substituted with one or more R$^b$.

7. The compound of claim 1 wherein $R^a$ is hydrogen, $R^2$ is hydrogen, methyl, or fluoro, and $R^{2'}$ is $(C_1-C_6)$alkyl, $(C_2-C_6)$alkenyl, $(C_2-C_6)$alkynyl, $(C_3-C_8)$cycloalkyl, aryl, or 5-6 membered heterocyclyl, wherein each alkyl, alkenyl, alkynyl, cycloalkyl, aryl, or heterocyclyl may be optionally substituted with one or more $R^b$.

8. The compound of claim 1 wherein $R^a$ and $R^2$ taken together are —CH$_2$—, —CH$_2$—CH$_2$—, —O—, —O—CH$_2$—, —CH$_2$O—, —O—CH$_2$—CH$_2$—, or —CH$_2$—CH$_2$—O—.

9. The compound of claim 1 wherein $R^a$ is hydrogen or an optional substituent, and $R^{2'}$ taken together with $R^2$ is cyclopropyl, cyclobutyl, or =CH—N(R$^c$)$_2$.

10. The compound of claim 1 wherein $R^a$ is hydrogen, and $R^{2'}$ taken together with $R^2$ is cyclopropyl, cyclobutyl, or =CH—N(R$^c$)$_2$.

11. The compound of claim 1 wherein $R^a$ is hydrogen or an optional substituent, and $R^{2'}$ taken together with $R^2$ is =CH—N(R$^c$)$_2$.

12. The compound of claim 1 wherein $R^a$ is hydrogen, and $R^{2'}$ taken together with $R^2$ is =CH—N(R$^c$)$_2$.

13. The compound of claim 1 wherein Z is selected from:

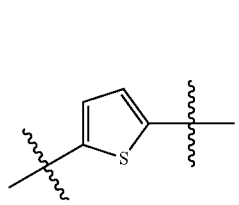 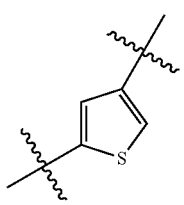

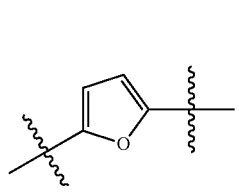 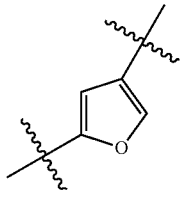

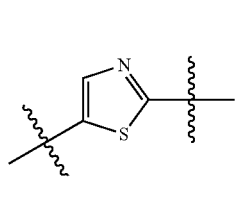 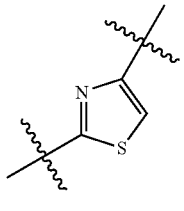

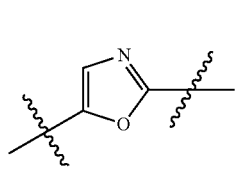 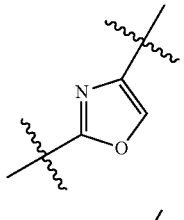

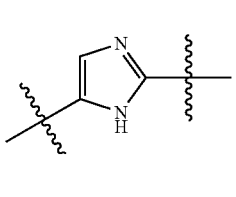 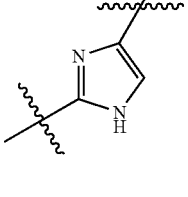

-continued

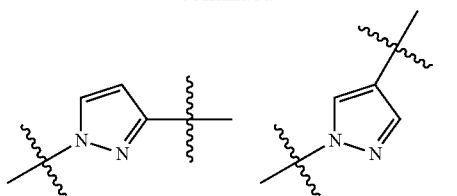

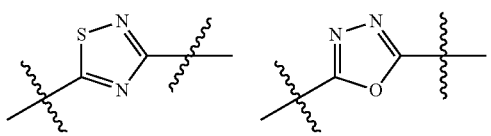

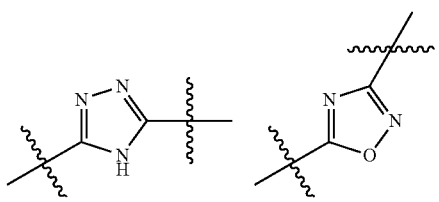

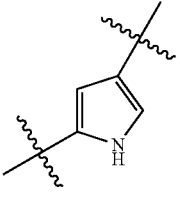 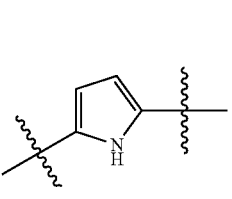

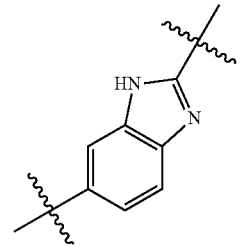 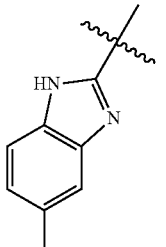

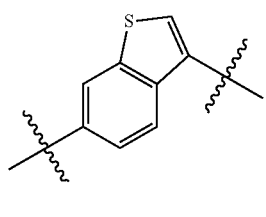 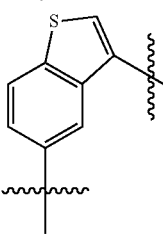

-continued

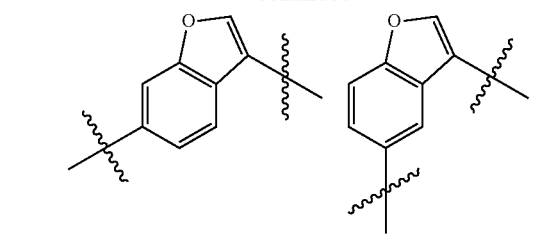
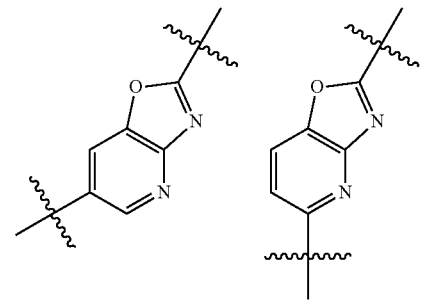
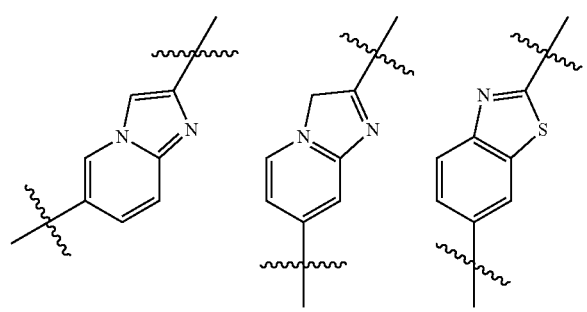
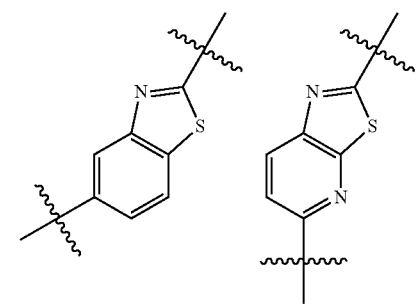
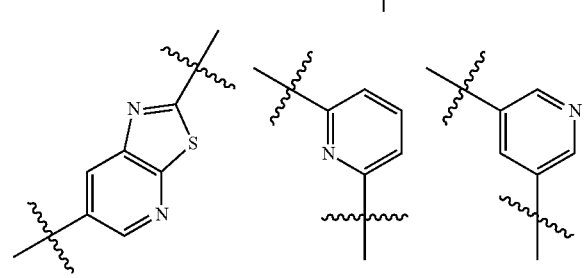
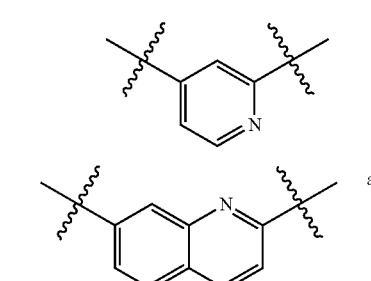
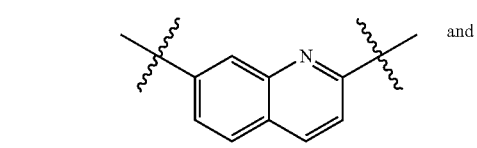
and -continued

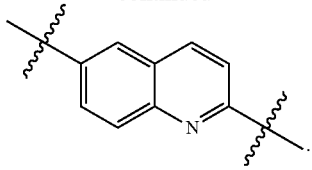

14. The compound of claim 1 wherein Z is selected from:

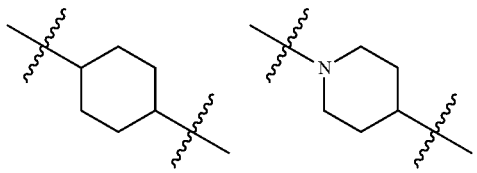
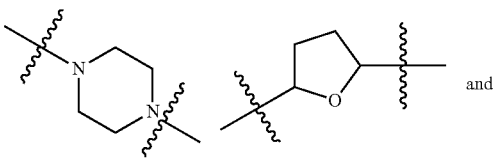
and
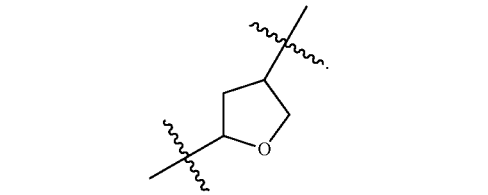

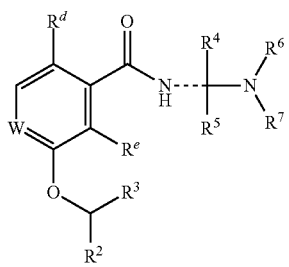

15. A compound of formula (Id):

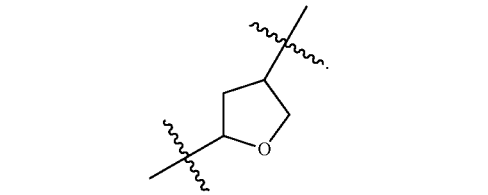

(Id)

wherein:
W is $CR^a$, or N;
$R^a$ is hydrogen, or an optional substituent, and $R^2$ is hydrogen, methyl, or fluoro; or $R^a$ and $R^2$ taken together are —$CH_2$—, —$CH_2$—$CH_2$—, —O—, —O—$CH_2$—, —$CH_2$O—, —O—$CH_2$—$CH_2$—, or —$CH_2$—$CH_2$—O—;
the bond represented by ---- is a double bond, $R^4$ is hydrogen or methyl, and $R^5$ and the hydrogen attached to the nitrogen are absent; or the bond represented by ---- is a single bond, $R^4$ is H, optionally substituted monocyclic carbocycle, or heterocyclic radical having 3 to 6 ring atoms, and $R^5$ is hydrogen; wherein each optionally substituted monocyclic carbocycle, or heterocyclic radical having 3 to 6 ring atoms of $R^4$ is optionally substituted with one or more substituents independently selected from $(C_1\text{-}C_6)$alkoxy, halo, hydroxy, cyano, nitro, amino, methylamino, dimethylamino, carboxy, $(C_1\text{-}C_6)$alkoxycarbonyl, aminocarbonyl, $C_6$)alkanoylamino, or tetrazole;

$R^6$ and $R^7$ are each independently hydrogen, $(C_1-C_6)$alkyl, $(C_2-C_6)$alkenyl, $(C_2-C_6)$alkynyl, or a heterocyclic radical having 3 to 6 ring atoms, or $R^6$ and $R^7$ together with the nitrogen to which they are attached form a 5 or 6 membered heterocyclic ring, which ring is optionally substituted with one or more groups independently selected from $(C_1-C_6)$alkyl; wherein any $(C_1-C_6)$alkyl of $R^6$ and $R^7$ is optionally substituted with one or more substituents independently selected from $(C_1-C_6)$ alkoxy, halo, hydroxy, cyano, nitro, amino, methylamino, dimethylamino, oxo (=O), carboxy, $(C_1-C_6)$ alkoxycarbonyl, aminocarbonyl, $(C_1-C_6)$ alkanoylamino, aryl, or tetrazole; and wherein any aryl or heterocyclic radical having 3 to 6 ring atoms of $R^6$ and $R^7$ is optionally substituted with one or more substituents independently selected from $(C_1-C_6)$alkyl, $(C_1-C_6)$alkoxy, halo, trifluoromethyl, trifluoromethoxy, hydroxy, cyano, nitro, tetrazole, carboxy, $(C_1-C_6)$ alkoxycarbonyl, or a $(C_1-C_4)$alkyl that is optionally substituted with one or more substituents independently selected from $(C_1-C_6)$alkoxy, halo, hydroxy, cyano, nitro, tetrazole, carboxy, $(C_1-C_6)$alkoxycarbonyl, amino, methylamino, dimethylamino, or oxo (=O);

$R^{1d}$ and $R^{1e}$ are independently fluoro or chloro, or one of $R^{1d}$ and $R^{1e}$ is hydrogen while the other is fluoro or chloro; and $R^3$ is a radical selected from:

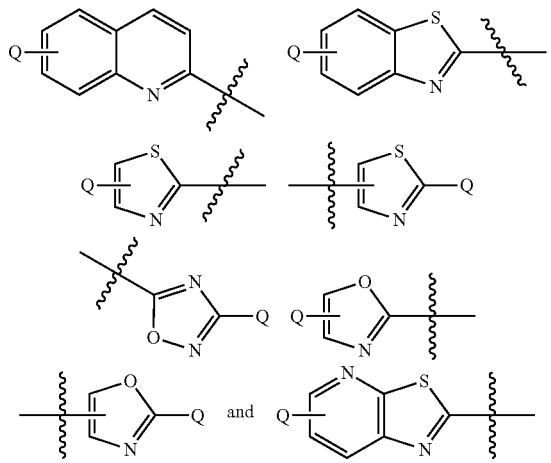

in which any vacant ring position is optionally substituted;

Q is hydrogen, halo, cyano, or hydroxyl, or an optionally substituted monocyclic carbocyclic or heterocyclic radical having 3 to 7 ring atoms, or an optionally substituted bicyclic heterocyclic radical having 5 to 10 ring atoms;

optional substituents are independently selected from, $(C_1-C_6)$alkyl, $(C_2-C_6)$alkenyl, $(C_2-C_6)$alkynyl, $(C_1-C_6)$ alkoxy, hydroxyl, hydroxy$(C_1-C_6)$alkyl, mercapto, mercapto$(C_1-C_6)$alkyl, $(C_1-C_6)$alkylthio, halo, fully or partially fluorinated $(C_1-C_3)$alkyl, fully or partially fluorinated $(C_1-C_3)$alkoxy, fully or partially fluorinated $(C_1-C_3)$alkylthio, nitro, cyano, oxo, phenyl, phenoxy, monocyclic heteroaryl or heteroaryloxy with 5 or 6 ring atoms, —COOR$^A$—, —COR$^A$—, —OCOR$^A$— —SO$_2$R$^A$—, —CONR$^A$R$^B$—, —SO$_2$NR$^A$R$^B$—, —NR$^A$R$^B$—, —OCONR$^A$R$^B$—, —NR$^B$COR$^A$—, —NR$^B$COOR$^A$—, —NR$^B$—SO$_2$OR$^A$—, or —NR$^A$-CONR$^A$R$^B$—, wherein R$^A$ and R$^B$ are independently hydrogen or a $(C_1-C_6)$alkyl group or, in the case where R$^A$ and R$^B$ are linked to the same N atom, R$^A$ and R$^B$ taken together with that nitrogen may form a cyclic amino ring; where the substituent is phenyl, phenoxy or monocyclic heteroaryl or heteroaryloxy with 5 or 6 ring atoms, the phenyl or heteroaryl ring thereof may itself be substituted by any of the above substituents except phenyl phenoxy, heteroaryl or heteroaryloxy;

or a salt thereof.

16. The compound of claim 15 wherein W is CH and $R^2$ is hydrogen.

17. The compound of claim 15 wherein Q is hydrogen or optionally substituted phenyl.

18. The compound of claim 15 wherein $R_3$ is optionally substituted quinolin-2-yl, benzothiazol-2-yl, thiazol-2-yl, thiazol-4-yl, thiazol-5-yl, oxadiazol-3-yl, oxadiazol-5-yl, oxazol-2-yl, oxazol-4-yl, oxazol-5-yl or thiazolopyridin-2-yl.

19. The compound of claim 18 wherein the optional substituents which may be present in $R_3$ are independently selected from methyl, —OCH$_3$, —CF$_3$, —OCF$_3$, ethyl, cyclopropyl, oxo, hydroxyl, fluoro, chloro, bromo, cyano, acetyl, amino, methylamino, dimethylamino, acetylamino, carbamate, —CONH$_2$, nitro, —COOH and —CH$_2$OH.

20. A compound of formula (Ie):

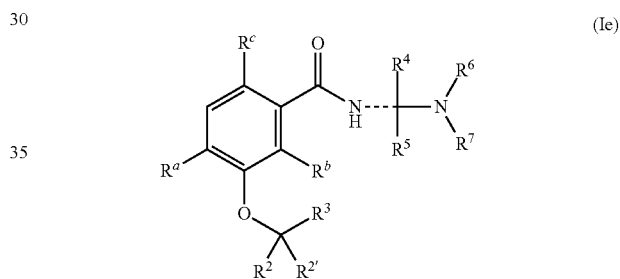

wherein:

$R^a$ is hydrogen, or an optional substituent, $R^2$ is hydrogen, methyl, or fluoro; and $R^2$ is hydrogen, $(C_1-C_6)$alkyl, $(C_2-C_6)$alkenyl, $(C_2-C_6)$alkynyl, $(C_3-C_8)$cycloalkyl, aryl, or 5-6 membered heterocyclyl, wherein each alkyl, alkenyl, alkynyl, cycloalkyl, aryl, or heterocyclyl may be optionally substituted with one or more $R^b$;

or $R^a$ and $R^2$ taken together are —CH$_2$—, —CH$_2$—CH$_2$—, —O—, —O—CH$_2$—, —CH$_2$O—, —O—CH$_2$—CH$_2$—, or —CH$_2$—CH$_2$—O—;

or $R^a$ is hydrogen or an optional substituent, and $R^2$ taken together with $R^{2'}$ is cyclopropyl, cyclobutyl, azetidine, or =CH—N(R$^c$)$_2$; wherein the cyclopropyl, cyclobutyl, and azetidine can optionally be substituted with $(C_1-C_6)$alkyl;

$R^3$ is -(Alk$^1$)$_m$—(Z)$_p$-(Alk$^2$)$_n$-Q;

Z is —O—, —S—, —S(O)—, —SO$_2$—, —NH—, —N(CH$_3$)—, —N(CH$_2$CH$_3$)—, —C(=O)—, —OC(=O)—, —C(=O)O—, or an optionally substituted divalent monocyclic carbocycle or heterocyclic radical having 3 to 6 ring atoms, or an optionally substituted divalent bicyclic heterocyclic radical having 5 to 10 ring atoms;

Alk$^1$ is optionally substituted $(C_1-C_6)$alkylene, $(C_2-C_6)$ alkenylene, or $(C_1-C_6)$alkynylene radical, which may optionally terminate with or be interrupted by —O—, —S—, —S(O)—, —SO$_2$—, —NH—, —N(CH$_3$)—, —N(CH$_2$CH$_3$)—;

Alk$^2$ is optionally substituted (C$_1$-C$_6$)alkylene, (C$_2$-C$_6$)alkenylene, or (C$_1$-C$_6$)alkynylene radical, which may optionally terminate with or be interrupted by —O—, —S—, —S(O)—, —SO$_2$—, —NH—, —N(CH$_3$)—, —N(CH$_2$CH$_3$)—;

Q is hydrogen, halo, cyano, or hydroxyl, or an optionally substituted monocyclic carbocyclic or heterocyclic radical having 3 to 7 ring atoms, or an optionally substituted bicyclic heterocyclic radical having 5 to 10 ring atoms;

the bond represented by ---- is a double bond, R$^4$ is hydrogen or methyl, and R$^5$ and the hydrogen attached to the nitrogen are absent; or the bond represented by ---- is a single bond, R$^4$ is H, optionally substituted monocyclic carbocycle, or heterocyclic radical having 3 to 6 ring atoms, and R$^5$ is hydrogen; wherein each optionally substituted monocyclic carbocycle, or heterocyclic radical having 3 to 6 ring atoms of R$^4$ is optionally substituted with one or more substituents independently selected from (C$_1$-C$_6$)alkoxy, halo, hydroxy, cyano, nitro, amino, methylamino, dimethylamino, carboxy, (C$_1$-C$_6$)alkoxycarbonyl, aminocarbonyl, (C$_1$-C$_6$)alkanoylamino, or tetrazole;

R$^6$ and R$^7$ are each independently hydrogen, (C$_1$-C$_6$)alkyl, (C$_2$-C$_6$)alkenyl, (C$_2$-C$_6$)alkynyl, or a heterocyclic radical having 3 to 6 ring atoms, or R$^6$ and R$^7$ together with the nitrogen to which they are attached form a 5 or 6 membered heterocyclic ring, which ring is optionally substituted with one or more groups independently selected from (C$_1$-C$_6$)alkyl; wherein any (C$_1$-C$_6$)alkyl of R$^6$ and R$^7$ is optionally substituted with one or more substituents independently selected from (C$_1$-C$_6$)alkoxy, halo, hydroxy, cyano, nitro, amino, methylamino, dimethylamino, oxo (=O), carboxy, (C$_1$-C$_6$)alkoxycarbonyl, aminocarbonyl, (C$_1$-C$_6$)alkanoylamino, aryl, or tetrazole; and wherein any aryl or heterocyclic radical having 3 to 6 ring atoms of R$^6$ and R$^7$ is optionally substituted with one or more substituents independently selected from (C$_1$-C$_6$)alkyl, (C$_1$-C$_6$)alkoxy, halo, trifluoromethyl, trifluoromethoxy, hydroxy, cyano, nitro, tetrazole, carboxy, (C$_1$-C$_6$)alkoxycarbonyl, or a (C$_1$-C$_4$)alkyl that is optionally substituted with one or more substituents independently selected from (C$_1$-C$_6$)alkoxy, halo, hydroxy, cyano, nitro, tetrazole, carboxy, (C$_1$-C$_6$)alkoxycarbonyl, amino, methylamino, dimethylamino, or oxo (=O);

each R$^b$ is independently R$^f$, OR$^e$, —C(=O)R$^e$, —OC(=O)R$^e$, —C(=O)OR$^e$, —N(R$^e$)$_2$, —NR$^e$C(=O)R$^d$, —C(=O)N(R$^e$)$_2$, —NR$^e$C(=O)OR$^d$, —OC(=O)N(R$^e$)$_2$, —C(=O)N(R$^e$)—N(R$^e$)C(=O)R$^d$, —NHC(=O)NHR$^d$, —NHS(O)$_{0-2}$R$^d$, —S(O)$_{0-2}$R$^d$, —OS(O)$_{0-2}$R$^d$, —OP(=O)(O1=e)$_2$, or —P(=O)(OR$^e$)$_2$;

each R$^e$ is independently H or (C$_1$-C$_6$)alkyl;

each R$^d$ is optionally substituted and is independently selected from (C$_1$-C$_6$)alkyl, (C$_2$-C$_6$)alkynyl, aryl, aryl(C$_1$-C$_6$)alkyl, 4-10 membered heterocyclyl and heterocyclyl(C$_1$-C$_6$)alkyl;

each R$^e$ is independently selected from H, (C$_1$-C$_6$)alkyl, (C$_2$-C$_6$)alkenyl, (C$_2$-C$_6$)alkynyl, aryl, aryl(C$_1$-C$_6$)alkyl, 4-10 membered heterocyclyl and heterocyclyl(C$_1$-C$_6$)alkyl, wherein each (C$_1$-C$_6$)alkyl, (C$_2$-C$_6$)alkenyl, (C$_2$-C$_6$)alkynyl, aryl, aryl(C$_1$-C$_6$)alkyl, 4-10 membered heterocyclyl and heterocyclyl(C$_1$-C$_6$)alkyl is optionally substituted;

each R$^f$ is optionally substituted and is independently selected from aryl and 4-10 membered heterocyclyl;

R$^{2c}$ is fluoro or chloro, and m, p, and n are each independently 0 or 1, provided that at least one of m, p, and n is 1;

optional substituents are independently selected from, (C$_1$-C$_6$)alkyl, (C$_2$-C$_6$)alkenyl, (C$_2$-C$_6$)alkynyl, (C$_1$-C$_6$)alkoxy, hydroxyl, hydroxy(C$_1$-C$_6$)alkyl, mercapto, mercapto(C$_1$-C$_6$)alkyl, (C$_1$-C$_6$)alkylthio, halo, fully or partially fluorinated (C$_1$-C$_3$)alkyl, fully or partially fluorinated (C$_1$-C$_3$)alkoxy, fully or partially fluorinated (C$_1$-C$_3$)alkylthio, nitro, cyano, oxo, phenyl, phenoxy, monocyclic heteroaryl or heteroaryloxy with 5 or 6 ring atoms, —COOR$^A$—, —COR$^A$—, —OCOR$^A$— —SO$_2$R$^A$—, —CONR$^A$R$^B$—, —SO$_2$NR$^A$R$^B$—, —NR$^A$R$^B$—, —OCONR$^A$R$^B$—, —NR$^B$COR$^A$—, —NR$^B$COOR$^A$—, —NR$^B$—SO$_2$OR$^A$—, or —NR$^A$-CONR$^A$R$^B$—, wherein R$^A$ and R$^B$ are independently hydrogen or a (C$_1$-C$_6$)alkyl group or, in the case where R$^A$ and R$^B$ are linked to the same N atom, R$^A$ and R$^B$ taken together with that nitrogen may form a cyclic amino ring; where the substituent is phenyl, phenoxy or monocyclic heteroaryl or heteroaryloxy with 5 or 6 ring atoms, the phenyl or heteroaryl ring thereof may itself be substituted by any of the above substituents except phenyl phenoxy, heteroaryl or heteroaryloxy;

or a salt thereof.

21. A compound of formula (If):

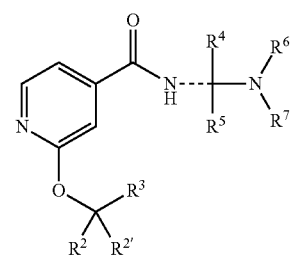

(If)

wherein:

R$^2$ is hydrogen, methyl, or fluoro, and R$^{2'}$ is hydrogen, (C$_1$-C$_6$)alkyl, (C$_2$-C$_6$)alkenyl, (C$_2$-C$_6$)alkynyl, (C$_3$-C$_8$)cycloalkyl, aryl, or 5-6 membered heterocyclyl, wherein each alkyl, alkenyl, alkynyl, cycloalkyl, aryl, or heterocyclyl may be optionally substituted with one or more R$^b$;

or R$^{2'}$ taken together with R$^2$ is cyclopropyl, cyclobutyl, azetidine, or =CH—N(R$^c$)$_2$; wherein the cyclopropyl, cyclobutyl, and azetidine can optionally be substituted with (C$_1$-C$_6$)alkyl;

R$^3$ is -(Alk$^1$)$_m$-(Z)$_p$-(Alk$^2$)$_n$-Q;

Z is —O—, —S—, —S(O)—, —SO$_2$—, —NH—, —N(CH$_3$)—, —N(CH$_2$CH$_3$)—, —C(=O)—, —OC(=O)—, —C(=O)O—, or an optionally substituted divalent monocyclic carbocycle or heterocyclic radical having 3 to 6 ring atoms, or an optionally substituted divalent bicyclic heterocyclic radical having 5 to 10 ring atoms;

Alk$^1$ is optionally substituted (C$_1$-C$_6$)alkylene, (C$_2$-C$_6$)alkenylene, or (C$_1$-C$_6$)alkynylene radical, which may optionally terminate with or be interrupted by —O—, —S—, —S(O)—, —SO$_2$—, —NH—, —N(CH$_3$)—, —N(CH$_2$CH$_3$)—;

Alk$^2$ is optionally substituted (C$_1$-C$_6$)alkylene, (C$_2$-C$_6$)alkenylene, or (C$_1$-C$_6$)alkynylene radical, which may optionally terminate with or be interrupted by —O—, —S—, —S(O)—, —SO$_2$—, —NH—, —N(CH$_3$)—, —N(CH$_2$CH$_3$)—;

Q is hydrogen, halo, cyano, or hydroxyl, or an optionally substituted monocyclic carbocyclic or heterocyclic radical having 3 to 7 ring atoms, or an optionally substituted bicyclic heterocyclic radical having 5 to 10 ring atoms;

the bond represented by ---- is a double bond, R$^4$ is hydrogen or methyl, and R$^5$ and the hydrogen attached to the nitrogen are absent; or the bond represented by ---- is a single bond, R$^4$ is H, optionally substituted monocyclic carbocycle, or heterocyclic radical having 3 to 6 ring atoms, and R$^5$ is hydrogen; wherein each optionally substituted monocyclic carbocycle, or heterocyclic radical having 3 to 6 ring atoms of R$^4$ is optionally substituted with one or more substituents independently selected from (C$_1$-C$_6$)alkoxy, halo, hydroxy, cyano, nitro, amino, methylamino, dimethylamino, carboxy, (C$_1$-C$_6$)alkoxycarbonyl, aminocarbonyl, (C$_1$-C$_6$)alkanoylamino, or tetrazole;

R$^6$ and R$^7$ are each independently hydrogen, (C$_1$-C$_6$)alkyl, (C$_2$-C$_6$)alkenyl, (C$_2$-C$_6$)alkynyl, or a heterocyclic radical having 3 to 6 ring atoms, or R$^6$ and R$^7$ together with the nitrogen to which they are attached form a 5 or 6 membered heterocyclic ring, which ring is optionally substituted with one or more groups independently selected from (C$_1$-C$_6$)alkyl; wherein any (C$_1$-C$_6$)alkyl of R$^6$ and R$^7$ is optionally substituted with one or more substituents independently selected from (C$_1$-C$_6$)alkoxy, halo, hydroxy, cyano, nitro, amino, methylamino, dimethylamino, oxo carboxy, (C$_1$-C$_6$)alkoxycarbonyl, aminocarbonyl, (C$_1$-C$_6$)alkanoylamino, aryl, or tetrazole; and wherein any aryl or heterocyclic radical having 3 to 6 ring atoms of R$^6$ and R$^7$ is optionally substituted with one or more substituents independently selected from (C$_1$-C$_6$)alkyl, (C$_1$-C$_6$)alkoxy, halo, trifluoromethyl, trifluoromethoxy, hydroxy, cyano, nitro, tetrazole, carboxy, (C$_1$-C$_6$)alkoxycarbonyl, or a (C$_1$-C$_4$)alkyl that is optionally substituted with one or more substituents independently selected from (C$_1$-C$_6$)alkoxy, halo, hydroxy, cyano, nitro, tetrazole, carboxy, (C$_1$-C$_6$)alkoxycarbonyl, amino, methylamino, dimethylamino, or oxo (=O);

each R$^b$ is independently R$^f$, OR$^e$, —C(=O)R$^e$, —OC(=O)R$^e$, —C(=O)OR$^e$, —N(R$^e$)$_2$, —NR$^e$C(=O)R$^d$, —C(=O)N(R$^e$)$_2$, —NR$^e$C(=O)OR$^d$, —OC(=O)N(R$^e$)$_2$, —C(=O)N(R$^e$)—N(R$^e$)C(=O)R$^d$, —NHC(=O)NHR$^d$, —NHS(O)$_{0-2}$R$^d$, —S(O)$_{0-2}$R$^d$, —OS(O)$_{0-2}$R$^d$, —OP(=O)(OR$^e$)$_2$, or —P(=O)(OR$^e$)$_2$;

each R$^c$ is independently H or (C$_1$-C$_6$)alkyl;

each R$^d$ is optionally substituted and is independently selected from (C$_1$-C$_6$)alkyl, (C$_2$-C$_6$)alkenyl, (C$_2$-C$_6$)alkynyl, aryl, aryl(C$_1$-C$_6$)alkyl, 4-10 membered heterocyclyl and heterocyclyl(C$_1$-C$_6$)alkyl;

each R$^e$ is independently selected from H, (C$_1$-C$_6$)alkyl, (C$_2$-C$_6$)alkenyl, (C$_2$-C$_6$)alkynyl, aryl, aryl(C$_1$-C$_6$)alkyl, 4-10 membered heterocyclyl and heterocyclyl(C$_1$-C$_6$)alkyl, wherein each (C$_1$-C$_6$)alkyl, (C$_2$-C$_6$)alkenyl, (C$_2$-C$_6$)alkynyl, aryl, aryl(C$_1$-C$_6$)alkyl, 4-10 membered heterocyclyl and heterocyclyl(C$_1$-C$_6$)alkyl is optionally substituted;

each R$^f$ is optionally substituted and is independently selected from aryl and 4-10 membered heterocyclyl; and m, p, and n are each independently 0 or 1, provided that at least one of m, p, and n is 1;

optional substituents are independently selected from, (C$_1$-C$_6$)alkyl, (C$_2$-C$_6$)alkenyl, (C$_2$-C$_6$)alkynyl, (C$_1$-C$_6$)alkoxy, hydroxyl, hydroxy(C$_1$-C$_6$)alkyl, mercapto, mercapto(C$_1$-C$_6$)alkyl, (C$_1$-C$_6$)alkylthio, halo, fully or partially fluorinated (C$_1$-C$_3$)alkyl, fully or partially fluorinated (C$_1$-C$_3$)alkoxy, fully or partially fluorinated (C$_1$-C$_3$)alkylthio, nitro, cyano, oxo, phenyl, phenoxy, monocyclic heteroaryl or heteroaryloxy with 5 or 6 ring atoms, —COOR$^A$—, —COR$^A$—, —OCOR$^A$— —SO$_2$R$^A$—, —CONR$^A$R$^B$—, —SO$_2$NR$^A$R$^B$—, —NR$^A$R$^B$—, —OCONR$^A$R$^B$—, —NR$^B$COR$^A$—, —NR$^B$COOR$^A$—, —NR$^B$—SO$_2$OR$^A$—, or —NR$^A$-CONR$^A$R$^B$—, wherein R$^A$ and R$^B$ are independently hydrogen or a (C$_1$-C$_6$)alkyl group or, in the case where R$^A$ and R$^B$ are linked to the same N atom, R$^A$ and R$^B$ taken together with that nitrogen may form a cyclic amino ring; where the substituent is phenyl, phenoxy or monocyclic heteroaryl or heteroaryloxy with 5 or 6 ring atoms, the phenyl or heteroaryl ring thereof may itself be substituted by any of the above substituents except phenyl phenoxy, heteroaryl or heteroaryloxy;

or a salt thereof.

22. A compound of formula (Ig):

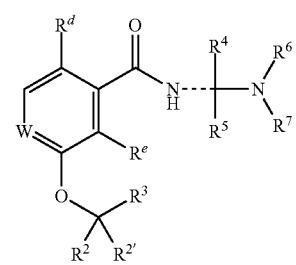

(Ig)

wherein:

W is CR$^a$, or N;

R$^a$ is hydrogen, or an optional substituent, R$^2$ is hydrogen, methyl, or fluoro, and R$^{2'}$ is hydrogen, (C$_1$-C$_6$)alkyl, (C$_2$-C$_6$)alkenyl, (C$_2$-C$_6$)alkynyl, (C$_3$-C$_8$)cycloalkyl, aryl, or 5-6 membered heterocyclyl, wherein each alkyl, alkenyl, alkynyl, cycloalkyl, aryl, or heterocyclyl may be optionally substituted with one or more R$^b$;

or R$^a$ and R$^2$ taken together are —CH$_2$—, —CH$_2$—CH$_2$—, —O—, —O—CH$_2$—, —CH$_2$O—, —O—CH$_2$—CH$_2$—, or —CH$_2$—CH$_2$—O—;

or R$^a$ is hydrogen or an optional substituent, and R$^{2'}$ taken together with R$^2$ is cyclopropyl, cyclobutyl, azetidine, or =CH—N(R$^c$)$_2$; wherein the cyclopropyl, cyclobutyl, and azetidine can optionally be substituted with (C$_1$-C$_6$)alkyl;

each R$^b$ is independently R$^f$, OR$^e$, —C(=O)R$^e$, —OC(=O)R$^e$, —C(=O)OR$^e$, —N(R$^e$)$_2$, —NR$^e$C(=O)R$^d$, —C(=O)N(R$^e$)$_2$, —NR$^e$C(=O)OR$^d$, —OC(=O)N(R$^e$)$_2$, —C(=O)N(R$^e$)—N(R$^e$)C(=O)R$^d$, —NHC (=O)NHR$^d$, —NHS(O)$_{0-2}$R$^d$, —S(O)$_{0-2}$R$^d$, —OS(O)$_{0-2}$R$^d$, —OP(=O)(OR$^e$)$_2$, or —P(=O)(OR$^e$)$_2$;

each R$^c$ is independently H or (C$_1$-C$_6$)alkyl;

each R$^d$ is optionally substituted and is independently selected from (C$_1$-C$_6$)alkyl, (C$_2$-C$_6$)alkenyl, (C$_2$-C$_6$)alkynyl, aryl, aryl(C$_1$-C$_6$)alkyl, 4-10 membered heterocyclyl and heterocyclyl(C$_1$-C$_6$)alkyl;

each R$^e$ is independently selected from H, (C$_1$-C$_6$)alkyl, (C$_2$-C$_6$)alkenyl, (C$_2$-C$_6$)alkynyl, aryl, aryl(C$_1$-C$_6$)alkyl, 4-10 membered heterocyclyl and heterocyclyl(C$_1$-C$_6$)alkyl, wherein each (C$_1$-C$_6$)alkyl, (C$_2$-C$_6$)alkenyl, (C$_2$-C$_6$)alkynyl, aryl, aryl(C$_1$-C$_6$)alkyl, 4-10 membered heterocyclyl and heterocyclyl(C$_1$-C$_6$)alkyl is optionally substituted;

each R$^f$ is optionally substituted and is independently selected from aryl and 4-10 membered heterocyclyl; or R$^{2e}$ is fluoro or chloro, or one of R$^{2d}$ and R$^{2e}$ is hydrogen while the other is fluoro or chloro; and R$^3$ is a radical selected from:

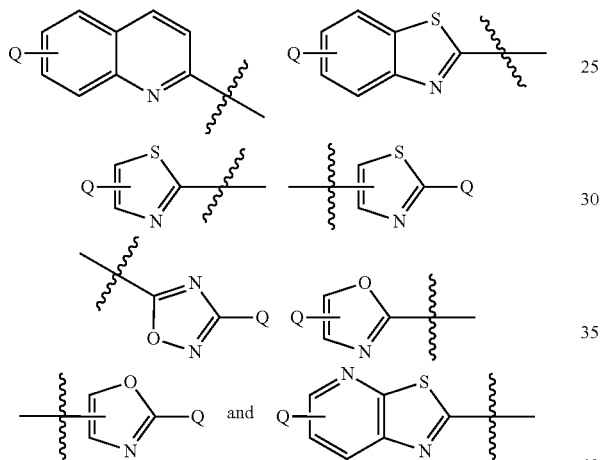

in which any vacant ring position is optionally substituted;

Q is hydrogen, halo, cyano, or hydroxyl, or an optionally substituted monocyclic carbocyclic or heterocyclic radical having 3 to 7 ring atoms, or an optionally substituted bicyclic heterocyclic radical having 5 to 10 ring atoms;

the bond represented by ---- is a double bond, R$^4$ is hydrogen or methyl, and R$^5$ and the hydrogen attached to the nitrogen are absent; or the bond represented by ---- is a single bond, R$^4$ is H, optionally substituted monocyclic carbocycle, or heterocyclic radical having 3 to 6 ring atoms, and R$^5$ is hydrogen; wherein each optionally substituted monocyclic carbocycle, or heterocyclic radical having 3 to 6 ring atoms of R$^4$ is optionally substituted with one or more substituents independently selected from (C$_1$-C$_6$)alkoxy, halo, hydroxy, cyano, nitro, amino, methylamino, dimethylamino, carboxy, (C$_1$-C$_6$)alkoxycarbonyl, aminocarbonyl, (C$_1$-C$_6$)alkanoylamino, or tetrazole;

R$^6$ and R$^7$ are each independently hydrogen, (C$_1$-C$_6$)alkyl, (C$_2$-C$_6$)alkenyl, (C$_2$-C$_6$)alkynyl, or a heterocyclic radical having 3 to 6 ring atoms, or R$^6$ and R$^7$ together with the nitrogen to which they are attached form a 5 or 6 membered heterocyclic ring, which ring is optionally substituted with one or more groups independently selected from (C$_1$-C$_6$)alkyl; wherein any (C$_1$-C$_6$)alkyl of R$^6$ and R$^7$ is optionally substituted with one or more substituents independently selected from (C$_1$-C$_6$)alkoxy, halo, hydroxy, cyano, nitro, amino, methylamino, dimethylamino, oxo (=O), carboxy, (C$_1$-C$_6$)alkoxycarbonyl, aminocarbonyl, (C$_1$-C$_6$)alkanoylamino, aryl, or tetrazole; and wherein any aryl or heterocyclic radical having 3 to 6 ring atoms of R$^6$ and R$^7$ is optionally substituted with one or more substituents independently selected from (C$_1$-C$_6$)alkyl, (C$_1$-C$_6$)alkoxy, halo, trifluoromethyl, trifluoromethoxy, hydroxy, cyano, nitro, tetrazole, carboxy, (C$_1$-C$_6$)alkoxycarbonyl, or a (C$_1$-C$_4$)alkyl that is optionally substituted with one or more substituents independently selected from (C$_1$-C$_6$)alkoxy, halo, hydroxy, cyano, nitro, tetrazole, carboxy, (C$_1$-C$_6$)alkoxycarbonyl, amino, methylamino, dimethylamino, or oxo (=O);

optional substituents are independently selected from, (C$_1$-C$_6$)alkyl, (C$_2$-C$_6$)alkenyl, (C$_2$-C$_6$)alkynyl, (C$_1$-C$_6$)alkoxy, hydroxyl, hydroxy(C$_1$-C$_6$)alkyl, mercapto, mercapto(C$_1$-C$_6$)alkyl, (C$_1$-C$_6$)alkylthio, halo, fully or partially fluorinated (C$_1$-C$_3$)alkyl, fully or partially fluorinated (C$_1$-C$_3$)alkoxy, fully or partially fluorinated (C$_1$-C$_3$)alkylthio, nitro, cyano, oxo, phenyl, phenoxy, monocyclic heteroaryl or heteroaryloxy with 5 or 6 ring atoms, —COOR$^A$—, —COR$^A$—, —OCOR$^A$—, —SO$_2$R$^A$—, —CONR$^A$R$^B$—, —SO$_2$NR$^A$R$^B$—, —NR$^A$R$^B$—, —OCONR$^A$R$^B$—, —NR$^B$COR$^A$—, —NR$^B$COOR$^A$—, —NR$^B$—SO$_2$OR$^A$—, or —NR$^A$-CONR$^A$R$^B$—, wherein R$^A$ and R$^B$ are independently hydrogen or a (C$_1$-C$_6$)alkyl group or, in the case where R$^A$ and R$^B$ are linked to the same N atom, R$^A$ and R$^B$ taken together with that nitrogen may form a cyclic amino ring; where the substituent is phenyl, phenoxy or monocyclic heteroaryl or heteroaryloxy with 5 or 6 ring atoms, the phenyl or heteroaryl ring thereof may itself be substituted by any of the above substituents except phenyl phenoxy, heteroaryl or heteroaryloxy;

or a salt thereof.

23. The compound of claim 20 wherein R$^2$ is hydrogen, methyl, or fluoro, and R$^{2'}$ is (C$_1$-C$_6$)alkyl, (C$_2$-C$_6$)alkenyl, (C$_2$-C$_6$)alkynyl, (C$_3$-C$_8$)cycloalkyl, aryl, or 5-6 membered heterocyclyl, wherein each alkyl, alkenyl, alkynyl, cycloalkyl, aryl, or heterocyclyl may be optionally substituted with one or more R$^b$.

24. The compound of claim 20 wherein R$^a$ and R$^2$ taken together are —CH$_2$—, —CH$_2$—CH$_2$—, —O—, —O—CH$_2$—, —CH$_2$O—, —O—CH$_2$—CH$_2$—, or —CH$_2$—CH$_2$—O—.

25. The compound of claim 20 wherein R$^{2'}$ taken together with R$^2$ is cyclopropyl, cyclobutyl, azetidine, or =CH—N(R$^c$)$_2$; wherein the cyclopropyl, cyclobutyl, and azetidine can optionally be substituted with (C$_1$-C$_6$)alkyl.

26. The compound of claim 1 wherein:

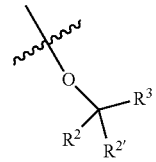

is selected from:
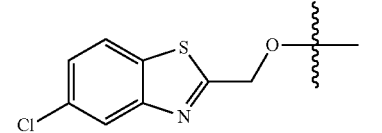
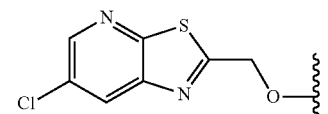
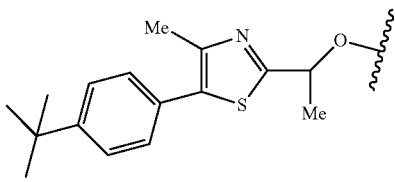
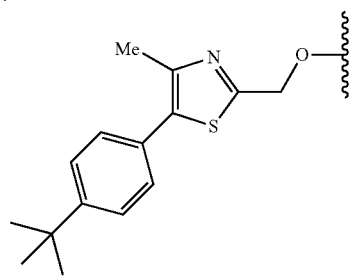
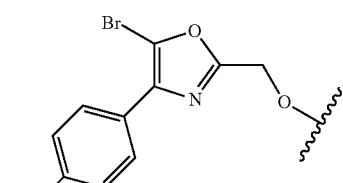
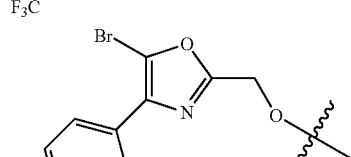
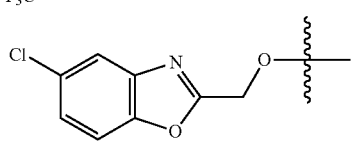
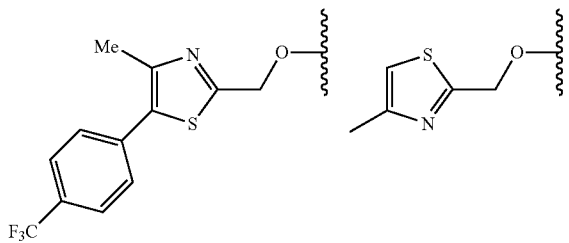
-continued
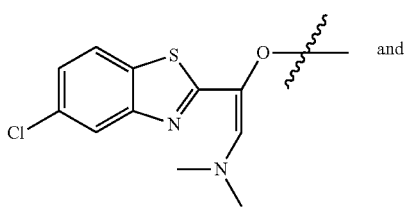
and
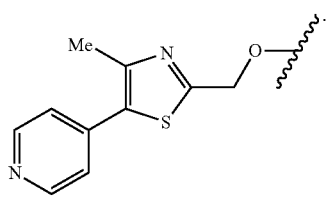
27. The compound of claim 1 wherein:
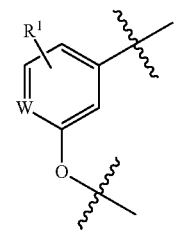
is selected from:
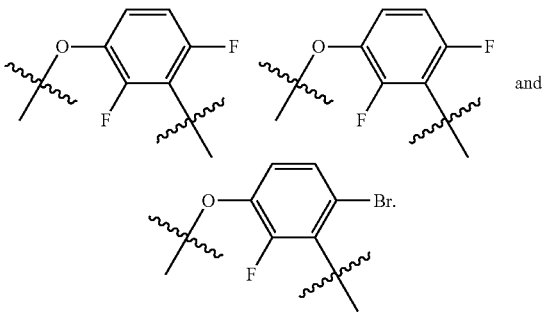
and
28. The compound of claim 1 wherein:
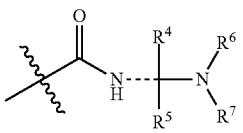
is selected from:
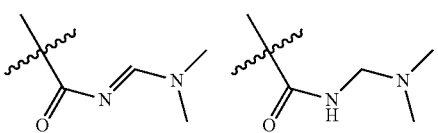

-continued
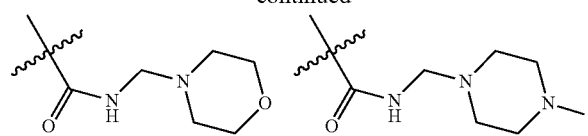
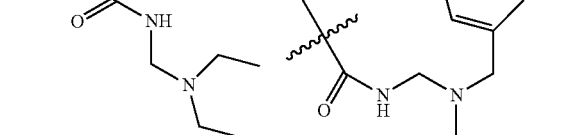
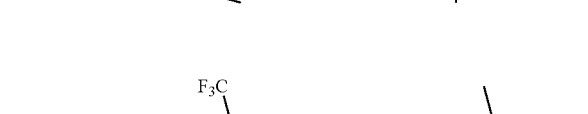
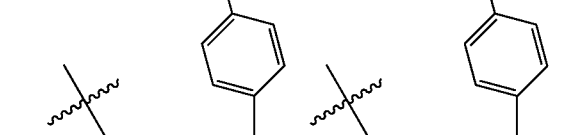
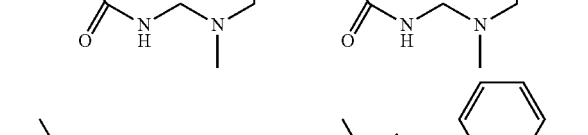
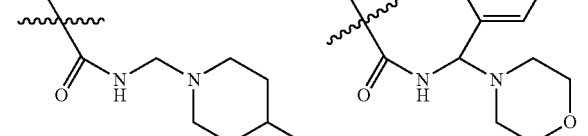
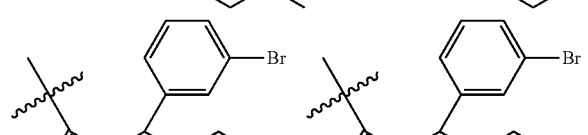
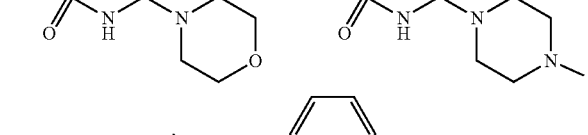
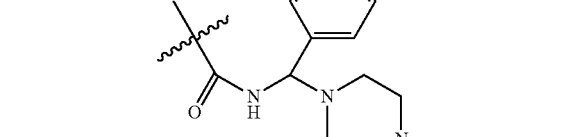
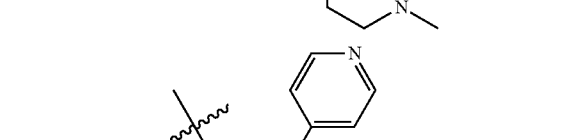
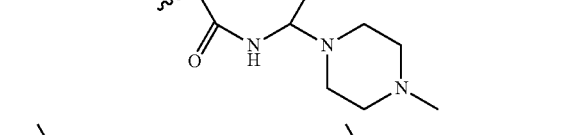
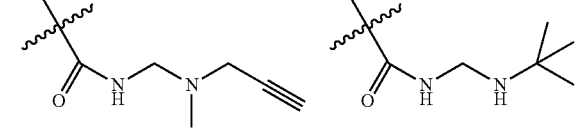
-continued
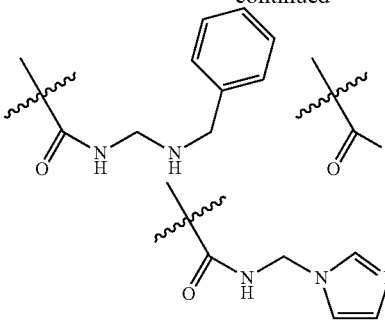
29. A compound selected from:
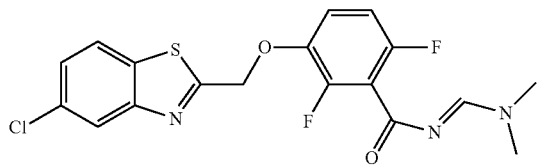
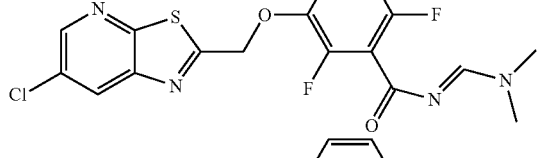
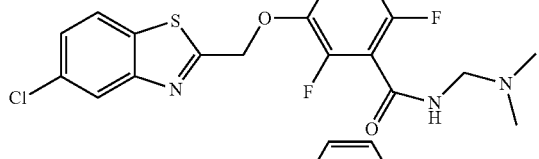
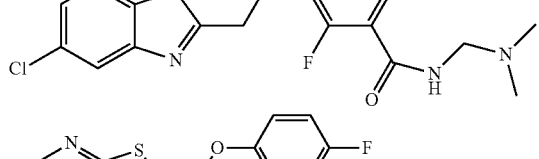
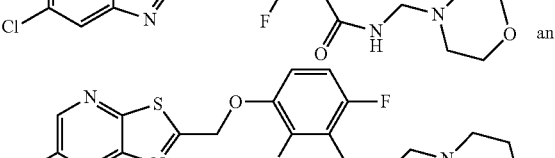
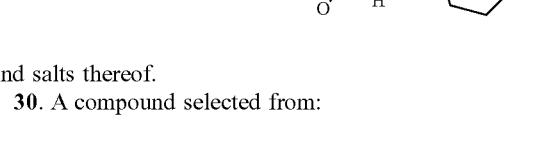
and salts thereof.
30. A compound selected from:
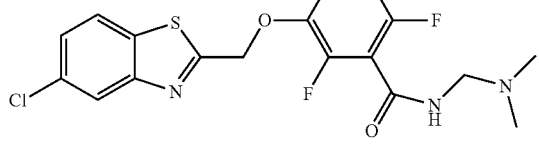
and salts thereof.

31. A compound selected from:
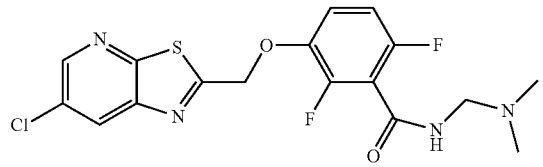
and salts thereof.
32. A compound selected from:
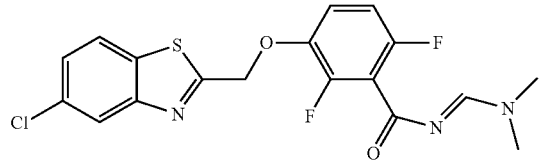
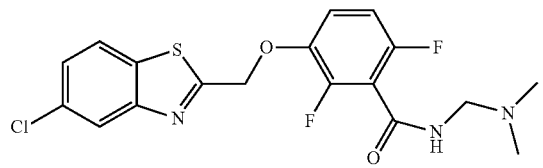 [SMILES: CN(C)CNC(=O)c1c(F)ccc(OCc2nc3cc(Cl)ccc3s2)c1F]
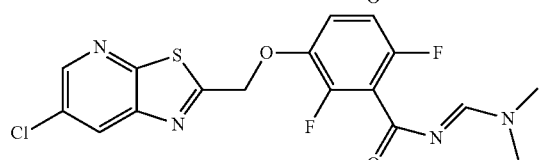
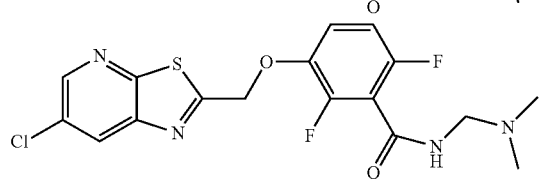
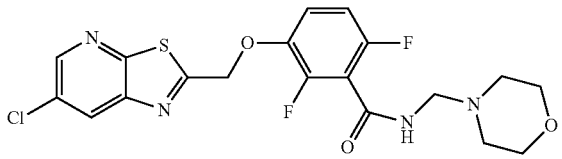
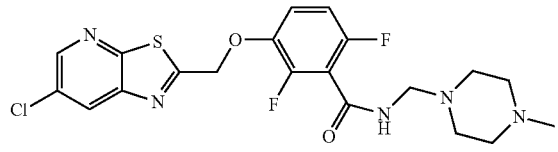
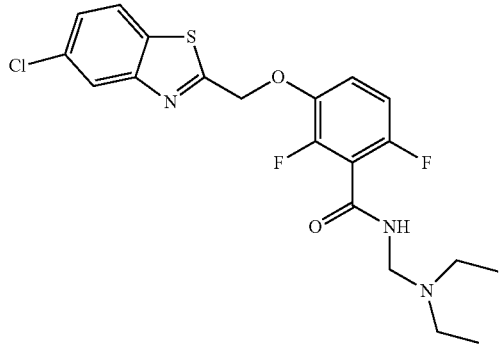
-continued
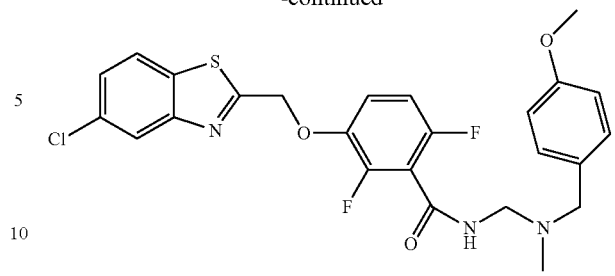
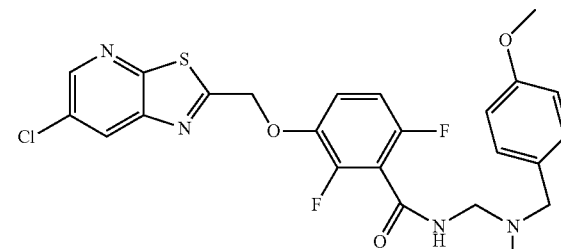
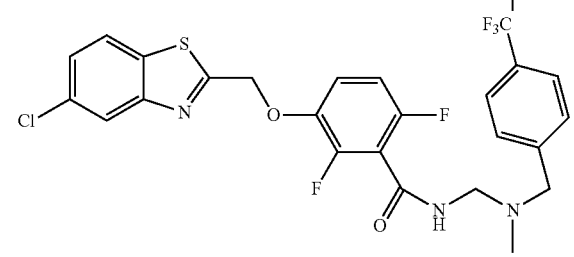
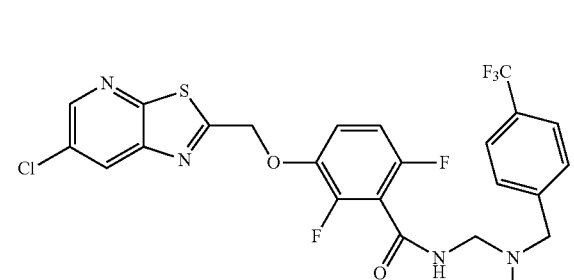
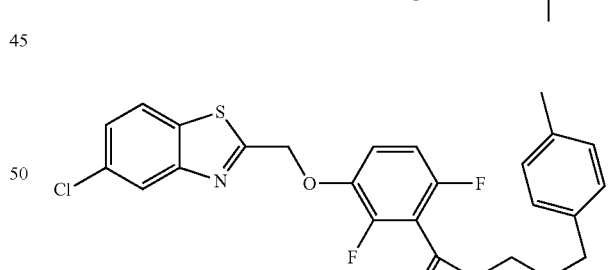
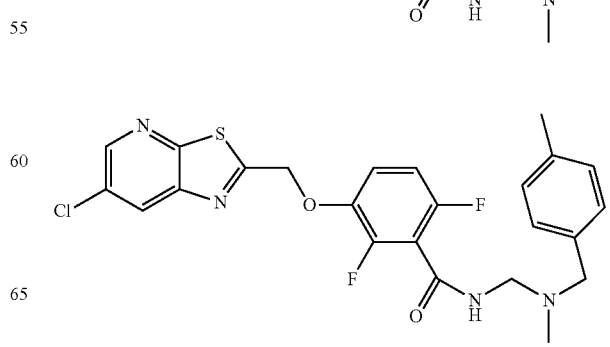

103
-continued
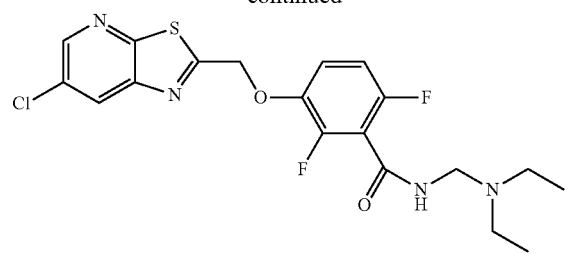
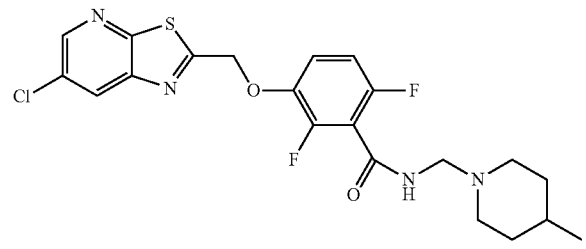
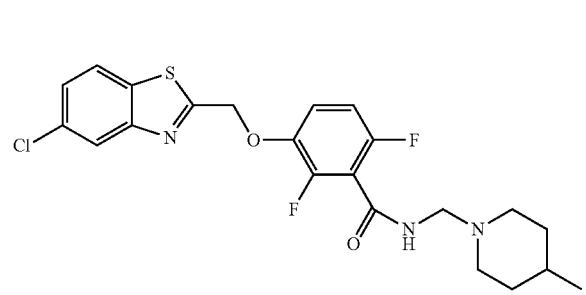
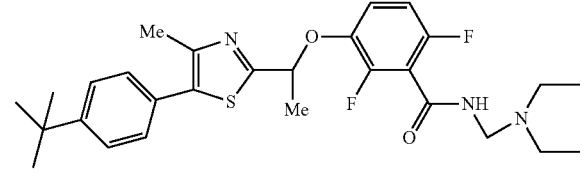
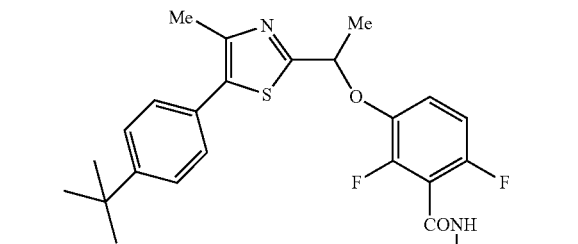
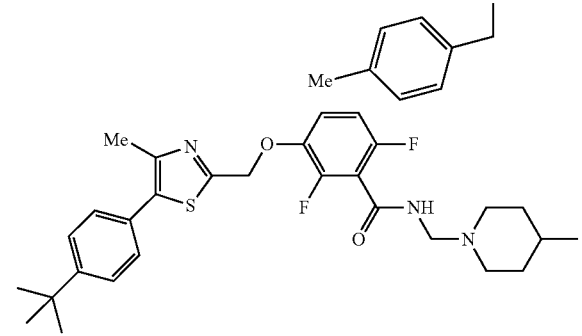
104
-continued
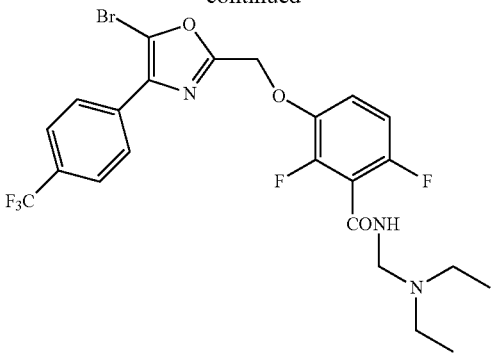
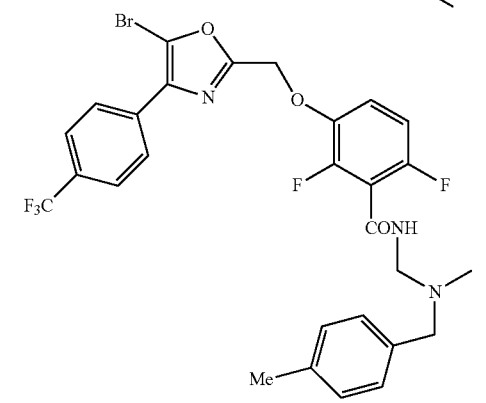
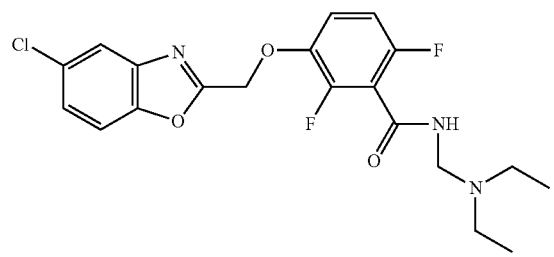
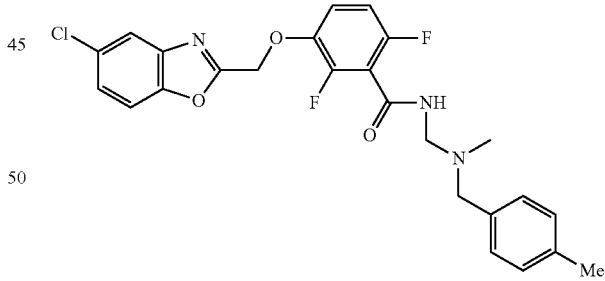
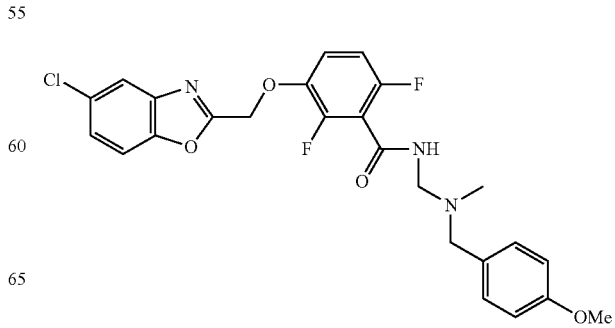

105
-continued
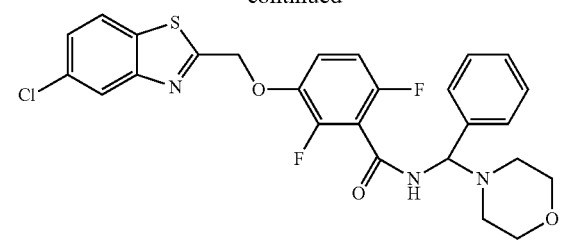
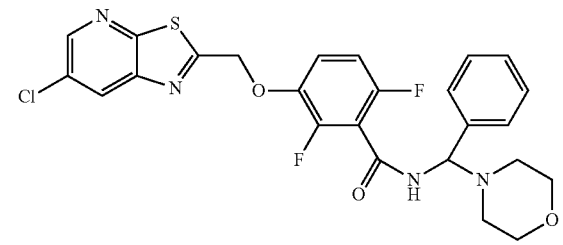
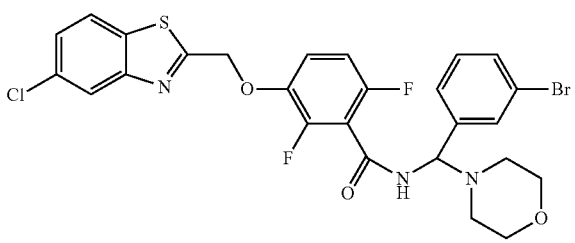
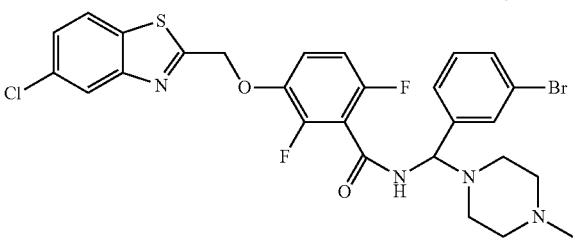
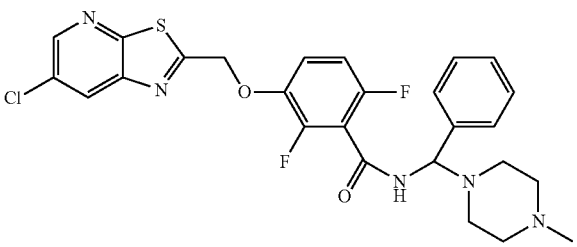
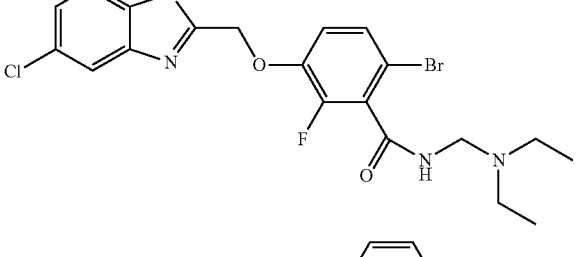
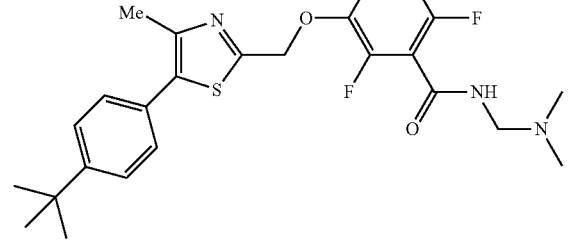
106
-continued
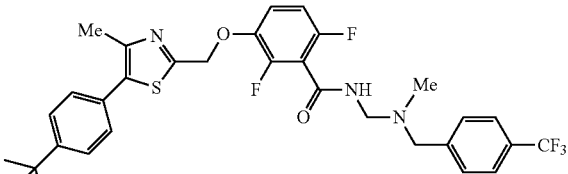
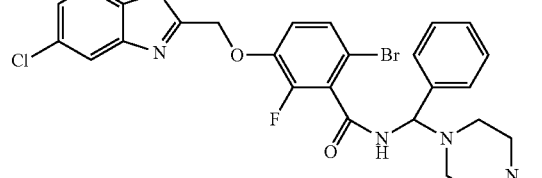
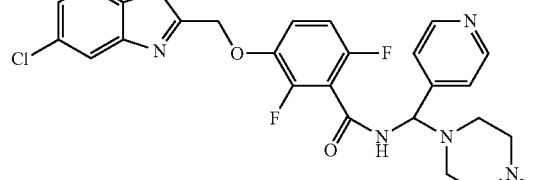
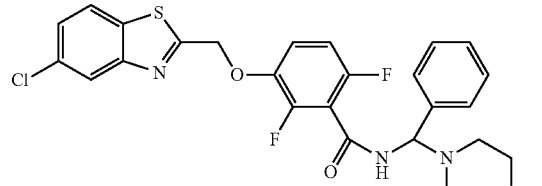
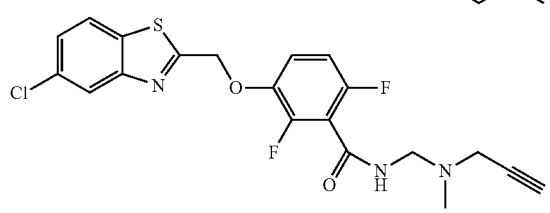
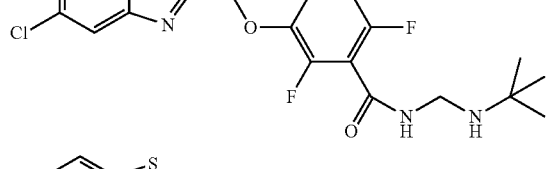
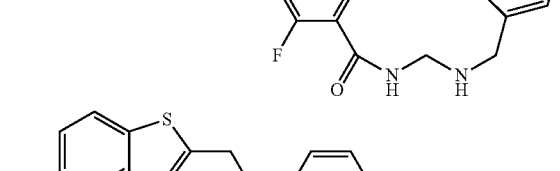
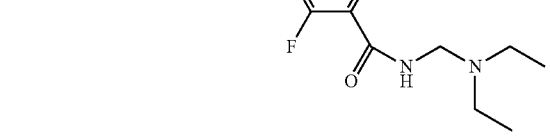

-continued

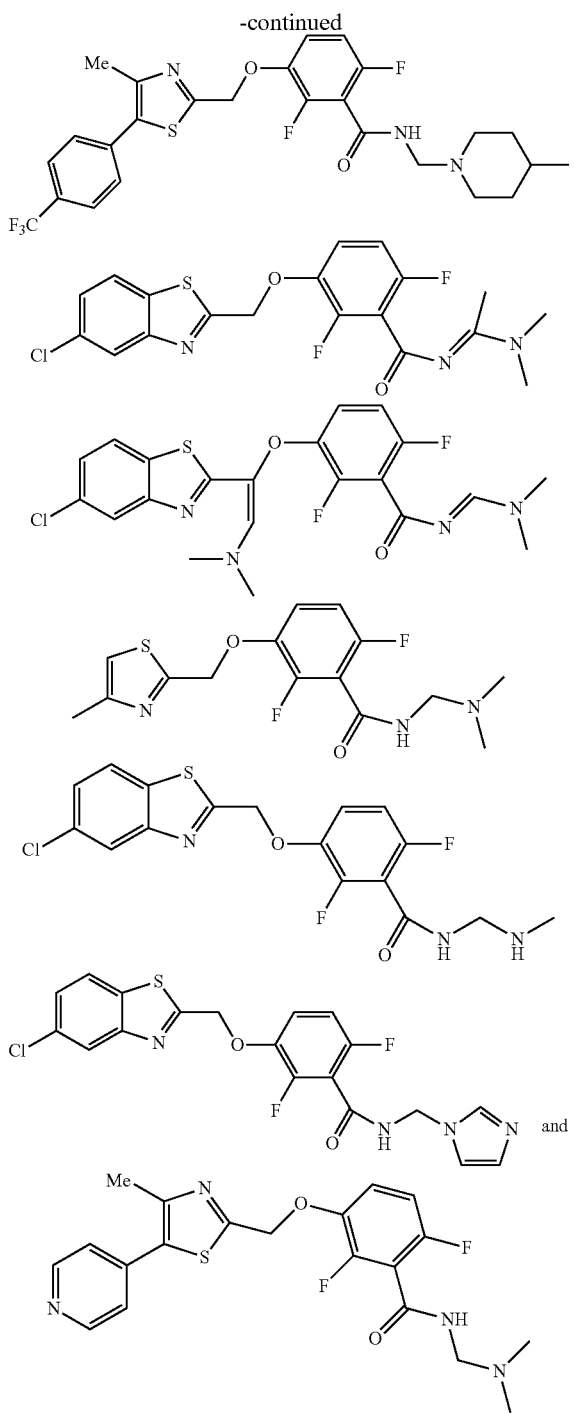

and salts thereof.

33. A method for treating a bacterial infection in a mammal comprising administering to the mammal an effective amount of a compound as described in claim 1, or a pharmaceutically acceptable salt thereof.

34. The method of claim 33 wherein the bacterial infection is a Gram-negative bacterial strain infection.

35. The method of claim 34 wherein the Gram-negative bacterial strain is selected from the group consisting of *Escherchia coli, Caulobacter crescentus, Pseudomonas aeruginosa, Agrobacterium tumefaciens, Branhamella catarrhalis, Citrobacter diversus, Enterobacter aerogenes, Enterobacter cloacae, Enterobacter sakazakii, Enterobacter asburiae, Pantoea agglomerans, Klebsiella pneumoniae, Klebsiella oxytoca, Klebsiella rhinoscleromatis, Proteus mirabilis, Salmonella typhimurium, Salmonella enteriditis, Serratia marcescens, Shigella sonnei, Neisseria gonorrhoeae, Acinetobacter baumannii, Acinetobacter calcoaceticus, Acinetobacter lwoffi, Salmonella enteriditis, Fusobacterium nucleatum, Veillonella parvula, Bacteroides forsythus, Actinobacillus actinomycetemcomitans, Aggregatibacter actinomycetemcomitans, Porphyromonas gingivalis, Helicobacter pylori, Francisella tularensis, Yersinia pestis, Borrelia burgdorferi, Neisseria meningitidis* and *Haemophilus influenzae*.

36. The method of claim 33 wherein the bacterial infection is a Gram-positive bacterial strain infection.

37. The method of claim 36 wherein the Gram-positive bacterial strain is selected from the group consisting of *Staphylococcus aureus, Staphylococcus epidermidis, Staphylococcus saprophyticus, Streptococcus pyogenes, Streptococcus faecalis, Enterococcus faecalis, Enterococcus faecium, Bacillus subtilis, Micrococcus luteus, Mycobacterium tuberculosis, Bacillus anthracia, Bacillus cereus, Clostridium difficile, Propionibacterium acnes, Streptococcus mutans, Actinomyces viscosus, Actinomyces naeslundii, Streptococcus sanguis, Streptococcus pneumoniae* and *Streptococcus salivarius*.

38. The method of claim 33 wherein the bacterial infection is a multiple drug-resistant bacterial strain infection.

39. The method of claim 38 wherein the multiple drug-resistance bacterial strain is selected from the group consisting of methicillin-resistant *Staphylococcus aureus*, vancomycin-resistant *Enterococcus*, multiple drug-resistant tuberculosis and multidrug-resistant *Clostridium difficile*.

40. A pharmaceutical composition comprising a compound of formula I as described in claim 1 or a pharmaceutically acceptable salt thereof, and a pharmaceutically acceptable vehicle.

41. A compound of formula (I):

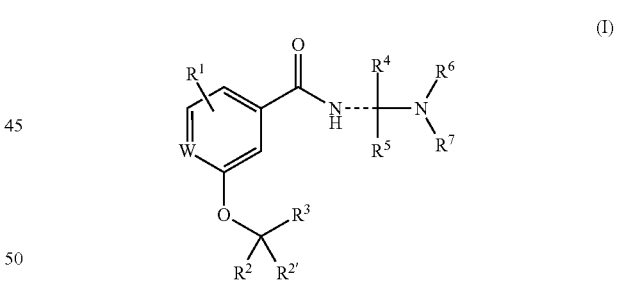

wherein:

$R^1$ is 1, 2 or 3 substituents independently selected from $(C_1-C_6)$alkyl, $(C_2-C_6)$alkenyl, $(C_2-C_6)$alkynyl, $(C_1-C_6)$alkoxy, hydroxyl, hydroxy$(C_1-C_6)$alkyl, mercapto, mercapto$(C_1-C_6)$alkyl, $(C_1-C_6)$alkylthio, halo, fully or partially fluorinated $(C_1-C_3)$alkyl, fully or partially fluorinated $(C_1-C_3)$alkoxy, fully or partially fluorinated $(C_1-C_3)$alkylthio, nitro, cyano, oxo, phenyl, phenoxy, monocyclic heteroaryl or heteroaryloxy with 5 or 6 ring atoms, —COOR$^A$—, —COR$^A$—, —OCOR$^A$—, —SO$_2$R$^A$, —CONR$^A$R$^B$—, —SO$_2$NR$^A$R$^B$—, —NR$^A$R$^B$—, —OCONR$^A$NR$^B$, —NR$^B$COR$^A$—, —NR$^B$COOR$^A$—, —NR$^B$—SO$_2$OR$^A$—, or —NR$^A$-CONR$^A$R$^B$—, wherein R$^A$ and R$^B$ are independently hydrogen or an $(C_1-C_6)$alkyl group or, in the case where $R^A$ and $R^B$ are linked to the same N atom, $R^A$ and $R^B$ taken together with that nitrogen may form a cyclic amino ring; where the substituent is phenyl, phenoxy or monocyclic heteroaryl or heteroaryloxy with 5 or 6 ring atoms, the phenyl or heteroaryl ring thereof may itself be substituted by any of the above substituents except phenyl phenoxy, heteroaryl or heteroaryloxy;

W is $CR^a$, or N;

$R^a$ is absent, hydrogen, or an optional substituent, $R^2$ is hydrogen, methyl, or fluoro, and $R^{2'}$ is hydrogen, $(C_1-C_6)$alkyl, $(C_2-C_6)$alkenyl, $(C_2-C_6)$alkynyl, $(C_3-C_8)$cycloalkyl, aryl, or 5-6 membered heterocyclyl, wherein each alkyl, alkenyl, alkynyl, cycloalkyl, aryl, or heterocyclyl may be optionally substituted with one or more $R^b$;

or $R^a$ and $R^2$ taken together are —CH$_2$—, —CH$_2$—CH$_2$—, —O—, —O—CH$_2$—, —CH$_2$O—, —O—CH$_2$—CH$_2$—, or —CH$_2$—CH$_2$—O—;

or $R^a$ is absent, hydrogen or an optional substituent, and $R^{2'}$ taken together with $R^2$ is cyclopropyl, cyclobutyl, azetidine, or =CH—N($R^c$)$_2$; wherein the cyclopropyl, cyclobutyl, and azetidine can optionally be substituted with $(C_1-C_6)$alkyl;

$R^3$ is -(Alk$^1$)$_m$-(Z)$_p$-(Alk$^2$)$_n$-Q;

Z is —O—, —S—, —S(O)—, —SO$_2$—, —NH—, —N(CH$_3$)—, —N(CH$_2$CH$_3$)—, —C(=O)—, —OC(=O)—, —C(=O)O—, or an optionally substituted divalent monocyclic carbocycle or heterocyclic radical having 3 to 6 ring atoms, or an optionally substituted divalent bicyclic heterocyclic radical having 5 to 10 ring atoms;

Alk$^1$ is optionally substituted $(C_1-C_6)$alkylene, $(C_2-C_6)$alkenylene, or $(C_2-C_6)$alkynylene radical, which may optionally terminate with or be interrupted by —O—, —S—, —S(O)—, —SO$_2$—, —NH—, —N(CH$_3$)—, —N(CH$_2$CH$_3$)—;

Alk$^2$ is optionally substituted $(C_1-C_6)$alkylene, $(C_2-C_6)$alkenylene, or $(C_2-C_6)$alkynylene radical, which may optionally terminate with or be interrupted by —O—, —S—, —S(O)—, —SO$_2$—, —NH—, —N(CH$_3$)—, —N(CH$_2$CH$_3$)—;

Q is an optionally substituted monocyclic carbocyclic or heterocyclic radical having 3 to 7 ring atoms, or an optionally substituted bicyclic heterocyclic radical having 5 to 10 ring atoms;

the bond represented by ---- is a double bond, $R^4$ is hydrogen or methyl, and $R^5$ and the hydrogen attached to the nitrogen are absent; or the bond represented by ---- is a single bond, $R^4$ is H, optionally substituted monocyclic carbocycle, or heterocyclic radical having 3 to 6 ring atoms, and $R^5$ is hydrogen; wherein each optionally substituted monocyclic carbocycle, or heterocyclic radical having 3 to 6 ring atoms of $R^4$ is optionally substituted with one or more substituents independently selected from $(C_1-C_6)$alkoxy, halo, hydroxy, cyano, nitro, amino, methylamino, dimethylamino, carboxy, $(C_1-C_6)$alkoxycarbonyl, aminocarbonyl, $(C_1-C_6)$alkanoylamino, or tetrazole;

$R^6$ and $R^7$ are each independently hydrogen, $(C_1-C_6)$alkyl, $(C_2-C_6)$alkenyl, $(C_2-C_6)$alkynyl, or a heterocyclic radical having 3 to 6 ring atoms, or $R^6$ and $R^7$ together with the nitrogen to which they are attached form a 5 or 6 membered heterocyclic ring, which ring is optionally substituted with one or more groups independently selected from $(C_1-C_6)$alkyl; wherein any $(C_1-C_6)$alkyl of $R^6$ and $R^7$ is optionally substituted with one or more substituents independently selected from $(C_1-C_6)$alkoxy, halo, hydroxy, cyano, nitro, amino, methylamino, dimethylamino, oxo (=O), carboxy, $(C_1-C_6)$alkoxycarbonyl, aminocarbonyl, $(C_1-C_6)$alkanoylamino, aryl, or tetrazole; and wherein any aryl or heterocyclic radical having 3 to 6 ring atoms of $R^6$ and $R^7$ is optionally substituted with one or more substituents independently selected from $(C_1-C_6)$alkyl, $(C_1-C_6)$alkoxy, halo, trifluoromethyl, trifluoromethoxy, hydroxy, cyano, nitro, tetrazole, carboxy, $(C_1-C_6)$alkoxycarbonyl, or a $(C_1-C_4)$alkyl that is optionally substituted with one or more substituents independently selected from $(C_1-C_6)$alkoxy, halo, hydroxy, cyano, nitro, tetrazole, carboxy, $(C_1-C_6)$alkoxycarbonyl, amino, methylamino, dimethylamino, or oxo (=O);

each $R^b$ is independently $R^f$, $OR^e$, —C(=O)$R^e$, —OC(=O)$R^e$, —C(=O)O$R^e$, —N($R^e$)$_2$, —NR$^e$C(=O)$R^d$, —C(=O)N($R^e$)$_2$, —NR$^e$C(=O)O$R^d$, —OC(=O)N($R^e$)$_2$, —C(=O)N($R^e$)—N($R^e$)C(=O)$R^d$, —NHC(=O)NH$R^d$, —NHS(O)$_{0-2}R^d$, —S(O)$_{0-2}R^d$, —OS(O)$_{0-2}$ $R^d$, —OP(=O)(OR$^e$)$_2$, or —P(=O)(OR$^e$)$_2$;

each $R^c$ is independently H or $(C_1-C_6)$alkyl;

each $R^d$ is optionally substituted and is independently selected from $(C_1-C_6)$alkyl, $(C_2-C_6)$alkenyl, $(C_2-C_6)$alkynyl, aryl, aryl$(C_1-C_6)$alkyl, 4-10 membered heterocyclyl and heterocyclyl$(C_1-C_6)$alkyl;

each $R^e$ is independently selected from H, $(C_1-C_6)$alkyl, $(C_2-C_6)$alkenyl, $(C_2-C_6)$alkynyl, aryl, aryl$(C_1-C_6)$alkyl, 4-10 membered heterocyclyl and heterocyclyl$(C_1-C_6)$alkyl, wherein each $(C_1-C_6)$alkyl, $(C_2-C_6)$alkenyl, $(C_2-C_6)$alkynyl, aryl, aryl$(C_1-C_6)$alkyl, 4-10 membered heterocyclyl and heterocyclyl$(C_1-C_6)$alkyl is optionally substituted;

each $R^f$ is optionally substituted and is independently selected from aryl and 4-10 membered heterocyclyl; and m, p, and n are each independently 0 or 1, provided that at least one of m, p, and n is 1; and optional substituents are independently selected from, $(C_1-C_6)$alkyl, $(C_2-C_6)$alkenyl, $(C_2-C_6)$alkynyl, $(C_1-C_6)$alkoxy, hydroxyl, hydroxy$(C_1-C_6)$alkyl, mercapto, mercapto$(C_1-C_6)$alkyl, $(C_1-C_6)$alkylthio, halo, fully or partially fluorinated $(C_1-C_3)$alkyl, fully or partially fluorinated $(C_1-C_3)$alkoxy, fully or partially fluorinated $(C_1-C_3)$alkylthio, nitro, cyano, oxo, phenyl, phenoxy, monocyclic heteroaryl or heteroaryloxy with 5 or 6 ring atoms, —COO$R^A$—, —CO$R^A$—, —OCO$R^A$—, —SO$_2R^A$—, —CONR$^A$R$^B$—, —SO$_2$NR$^A$R$^B$, —NR$^A$R$^B$—, —OCONR$^A$R$^B$—, —NR$^B$COR$^A$—, —NR$^B$COOR$^A$—, —NR$^B$—SO$_2$OR$^A$—, or —NR$^A$-CONR$^A$R$^B$—, wherein $R^A$ and $R^B$ are independently hydrogen or a $(C_1-C_6)$alkyl group or, in the case where $R^A$ and $R^B$ are linked to the same N atom, $R^A$ and $R^B$ taken together with that nitrogen may form a cyclic amino ring; where the substituent is phenyl, phenoxy or monocyclic heteroaryl or heteroaryloxy with 5 or 6 ring atoms, the phenyl or heteroaryl ring thereof may itself be substituted by any of the above substituents except phenyl phenoxy, heteroaryl or heteroaryloxy;

or a salt thereof.

* * * * *

UNITED STATES PATENT AND TRADEMARK OFFICE
CERTIFICATE OF CORRECTION

PATENT NO. : 9,475,783 B2
APPLICATION NO. : 14/386718
DATED : October 25, 2016
INVENTOR(S) : Edmond J. LaVoie et al.

It is certified that error appears in the above-identified patent and that said Letters Patent is hereby corrected as shown below:

In the Claims

Column 78, Line 3, Claim 1, delete "$SO_2NR^AR^B$ ," and insert -- $SO_2NR^AR^B$, $NR^AR^B$, --;

Column 78, Line 17, Claim 1, delete "$R^{2'}$" and insert -- $R^{2'}$ --;

Column 78, Line 31, Claim 1, delete "$(Alk')_m$" and insert -- $(Alk^1)_m$ --;

Column 78, Lines 39-40, Claim 1, delete "$(C_2-C_6)$alkynylene radical" and insert -- $(C-C_6)$alkynylene radical --;

Column 79, Line 29, Claim 1, delete "each $R^{e'}$" and insert -- each $R^c$ --;

Column 81, Lines 53-63, Claim 3, delete " 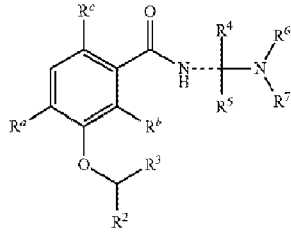 " and insert

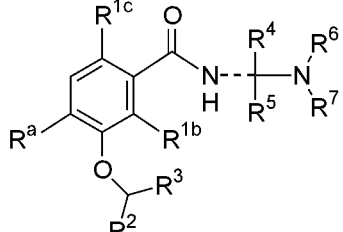

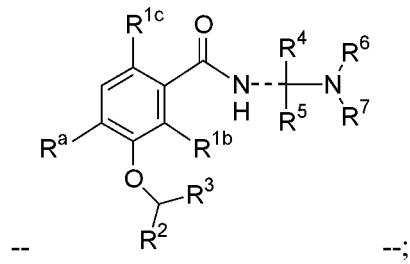

-- --;

Column 83, Line 12, Claim 3, delete "-$SO_2NR^AR^B$-,'" and insert -- -$SO_2NR^AR^B$-, -$CONR^AR^B$-, --;

Signed and Sealed this
First Day of August, 2017

Joseph Matal
Performing the Functions and Duties of the
Under Secretary of Commerce for Intellectual Property and
Director of the United States Patent and Trademark Office

CERTIFICATE OF CORRECTION (continued)
U.S. Pat. No. 9,475,783 B2

Column 85, Line 23, Claim 12, delete "$R^{2^{\prime\prime}}$" and insert -- $R^{2'}$ --;

Column 88, Line 67, Claim 15, delete "$C_6$)" and insert -- $(C_1 - C_6)$ --;

Column 90, Lines 30-40, Claim 20, delete " 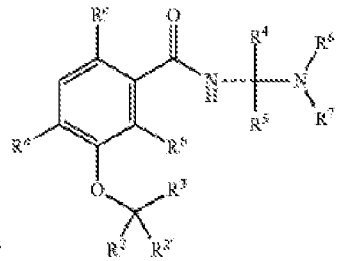 " and insert

-- 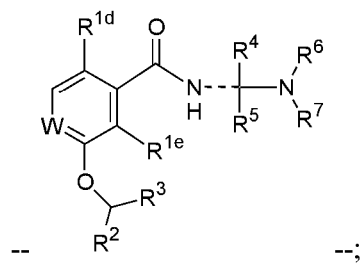 --;

Column 90, Line 44, Claim 20, delete "$R^{2^{\prime\prime}}$" and insert -- $R^{2'}$ --;

Column 90, Line 52, Claim 20, delete "$R^{2^{\prime\prime}}$" and insert -- $R^{2'}$ --;

Column 91, Line 57, Claim 20, delete "-OP(=O)(01=e)$_2$," and insert -- -OP(=O)(OR$^e$)$_2$, --;

Column 91, Line 59, Claim 20, delete "each R$^{e''}$" and insert -- each R$^c$ --;

Column 93, Line 38, Claim 21, delete "oxo carboxy," and insert -- oxo (=O), carboxy, --;

Column 94, Lines 35-45, Claim 22, delete " 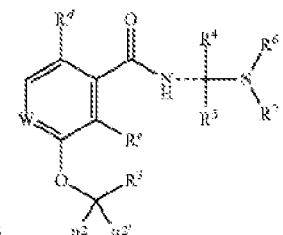 " and insert

-- 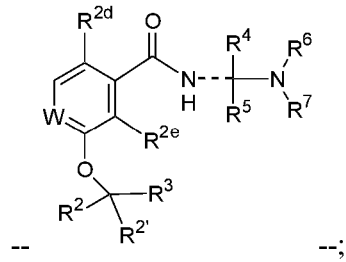 --;

CERTIFICATE OF CORRECTION (continued)
U.S. Pat. No. 9,475,783 B2

Column 94, Line 50, Claim 22, delete "$R^2$" and insert -- $R^{2'}$ --;

Column 108, Line 22, Claim 37, delete "anthracia" and insert -- anthracis --;

Column 108, Line 64, delete "-$OCONR^ANR^B$-" and insert -- -$OCONR^AR^B$- -- therefor.